(12) United States Patent
Siddiqi et al.

(10) Patent No.: US 8,114,973 B2
(45) Date of Patent: Feb. 14, 2012

(54) NUCLEOTIDE ANALOGS

(75) Inventors: Suhaib Siddiqi, Burlington, MA (US); Subramanian Marappan, Acton, MA (US); Judith Mitchell, Brighton, MA (US); Edyta Krzymanska-Olejnik, Brookline, MA (US); Atanu Roy, Woburn, MA (US); Xiaopeng Bai, Watertown, MA (US)

(73) Assignee: Helicos Biosciences Corporation, Cambridge, MA (US)

( * ) Notice: Subject to any disclaimer, the term of this patent is extended or adjusted under 35 U.S.C. 154(b) by 645 days.

(21) Appl. No.: 12/244,698

(22) Filed: Oct. 2, 2008

(65) Prior Publication Data

US 2009/0186351 A1    Jul. 23, 2009

Related U.S. Application Data

(63) Continuation-in-part of application No. 12/098,196, filed on Apr. 4, 2008, which is a continuation-in-part of application No. 11/929,084, filed on Oct. 30, 2007, now Pat. No. 7,994,304, which is a continuation of application No. 11/803,339, filed on May 14, 2007, now abandoned, which is a continuation-in-part of application No. 11/603,945, filed on Nov. 22, 2006, now abandoned, which is a continuation-in-part of application No. 11/295,406, filed on Dec. 5, 2005, now abandoned, which is a continuation-in-part of application No. 11/286,626, filed on Nov. 22, 2005, now abandoned, said application No. 11/803,339 is a continuation-in-part of application No. 11/295,155, filed on Dec. 6, 2005, now Pat. No. 7,476,734, which is a continuation-in-part of application No. 11/295,406, said application No. 11/803,339 is a continuation-in-part of application No. 11/496,262, filed on Jul. 31, 2006, now abandoned, which is a continuation-in-part of application No. 11/295,155, which is a continuation-in-part of application No. 11/295,406, said application No. 11/803,339 is a continuation-in-part of application No. 11/496,274, filed on Jul. 31, 2006, now abandoned, which is a continuation-in-part of application No. 11/496,262, said application No. 11/603,945 is a continuation-in-part of application No. 11/496,275, filed on Jul. 31, 2006, now abandoned, which is a continuation-in-part of application No. 11/496,274, application No. 12/244,698, which is a continuation-in-part of application No. 11/137,928, filed on May 25, 2005, now Pat. No. 7,635,562.

(60) Provisional application No. 60/574,389, filed on May 25, 2004.

(51) Int. Cl.
| | |
|---|---|
| *C07H 21/02* | (2006.01) |
| *C07H 21/04* | (2006.01) |
| *C07H 19/04* | (2006.01) |
| *C12Q 1/68* | (2006.01) |
| *C12P 19/34* | (2006.01) |

(52) U.S. Cl. ............ 536/23.1; 536/24.3; 536/26.6; 435/6.1; 435/91.1; 435/91.2

(58) Field of Classification Search .......... 435/6.1, 435/91.1, 91.2; 536/23.1, 24.3, 26.6
See application file for complete search history.

(56) References Cited

U.S. PATENT DOCUMENTS

| | | |
|---|---|---|
| 2005/0227231 A1 | 10/2005 | Tcherkassov |
| 2007/0128614 A1 | 6/2007 | Liu |
| 2009/0061437 A1 | 3/2009 | Efcavitch et al. |

FOREIGN PATENT DOCUMENTS

| | | |
|---|---|---|
| WO | WO 2005/044836 | 5/2005 |
| WO | WO 2007/062160 | 5/2007 |
| WO | WO 2008/137661 | 11/2008 |
| WO | WO 2008/144315 | 11/2008 |

OTHER PUBLICATIONS

International Search Report (ISR) and Written Opinion (WO) for PCT application No. PCT/US2009/039475, mailed Jul. 31, 2009, 14 pp.

*Primary Examiner* — Jezia Riley

(74) *Attorney, Agent, or Firm* — Brown Rudnick LLP; Thomas Meyers

(57) ABSTRACT

The invention provides for nucleotide analogs and methods of using the same, e.g., for sequencing nucleic acids.

20 Claims, No Drawings

NUCLEOTIDE ANALOGS

RELATED APPLICATIONS

This application is a continuation-in-part (CIP) of U.S. application Ser. No. 12/098,196 filed Apr. 4, 2008, which is a CIP of Ser. No. 11/929,084 filed Oct. 30, 2007, which is a continuation of Ser. No. 11/803,339 filed May 14, 2007, which is a CIP of Ser. No. 11/603,945 filed Nov. 22, 2006, which is a CIP of Ser. No. 11/295,406 filed Dec. 5, 2005, which is a CIP of Ser. No. 11/286,626 filed Nov. 22, 2005; Ser. No. 11/803,339 filed May 14, 2007 is a CIP of Ser. No. 11/295,155 filed Dec. 26, 2005, which is a CIP of Ser. No. 11/295,406 filed Dec. 5, 2005; Ser. No. 11/803,339 filed May 14, 2007 is a CIP of Ser. No. 11/496,262 filed Jul. 31, 2006, which is a CIP of Ser. No. 11/295,155 filed Dec. 26, 2005, which is a CIP of Ser. No. 11/295,406 filed Dec. 5, 2005; Ser. No. 11/803,339 filed May 14, 2007 is a CIP of Ser. No. 11/496,274 filed Jul. 31, 2006, which is a CIP of Ser. No. 11/496,262 filed Jul. 31, 2006; Ser. No. 11/603,945 filed Nov. 22, 2006 is a CIP of Ser. No. 11/496,275 filed Jul. 31, 2006, which is a CIP of Ser. No. 11/496,274 filed Jul. 31, 2006; this application is also a CIP of Ser. No. 11/137,928 filed May 25, 2005 which claims priority to 60/574,389 filed May 25, 2004, the entire contents of each of the above applications are expressly incorporated herein by reference for all purposes.

FIELD OF THE INVENTION

The invention relates to nucleotide analogs and methods for sequencing a nucleic acid using the nucleotide analogs.

BACKGROUND

Sequencing-by-synthesis involves the template-dependent addition of nucleotides to a template/primer duplex. Traditional sequencing-by-synthesis is performed using dye-labeled terminators and gel electrophoresis (so-called "Sanger sequencing"). See, e.g., Sanger, F. and Coulson, A. R., 1975, *J. Mol. Biol.* 94: 441-448; Sanger, F. et al., 1977, *Nature*. 265(5596): 687-695; and Sanger, F. et al., 1977, *Proc. Natl. Acad. Sci. U.S.A.* 75: 5463-5467. Recently, single molecule sequencing methods have been proposed that provide increased resolution, throughput, and speed at reduced cost. For example, a sequencing-by-synthesis method that results in sequence determination without consecutive base incorporation, has been proposed by Braslavsky, et al., *Proc. Nat'l Acad. Sci.*, 100: 3960-3964 (2003). These methods do not rely on the user of terminator nucleotides as in Sanger sequencing. Instead, template/primer duplex is anchored directly, or indirectly (e.g., via a polymerase enzyme) to a surface and labeled nucleotides are added in a template-dependent manner.

A challenge that has arisen in single molecule sequencing involves the ability to sequence through homopolymer regions (i.e., portions of the template that contain consecutive identical nucleotides). Often the number of bases present in a homopolymer region is important from the point of view of genetic function. Many polymerase enzymes used in sequencing-by-synthesis reactions are highly-processive and tend to add bases continuously in a homopolymer region. It is often difficult to resolve the number of nucleotides in a homopolymer due to the difficulty in distinguishing between the incorporation of one or two labeled nucleotides and the incorporation of a greater number of nucleotides.

A need therefore exists for nucleotide analogs that promote accurate base-over-base incorporation in sequencing-by-synthesis reactions.

SUMMARY OF THE INVENTION

The invention provides nucleotide analogs and methods of using them to allow sequencing-by-synthesis to occur such that, on average, a single nucleotide is incorporated into the 3' end of a primer portion of a template/primer duplex per sequencing cycle. The invention is based, in part, on the discovery that nucleotide analogs having an attached inhibitory region with one or more charged groups provide good incorporation of a single nucleotide into the duplex without allowing a significant, or any, amount of second, third, etc. base incorporation.

The invention generally provides nucleotide analogs and methods of using nucleotide analogs in sequencing. More particularly, the invention provides compounds, methods and compositions useful in introduction of a single base at a time in a template-dependent sequencing-by-synthesis reaction. The invention allows template-dependent sequencing-by-synthesis through all regions of a target nucleic acid, including homopolymer regions, and provides methods for the determination of the number of nucleotides present in a homopolymer region.

The invention provides nucleotide analogs that comprise a nucleotide (or nucleotide analog), a detectable label, and an inhibitor group. Upon incorporation of the nucleotide, the inhibitor prevents subsequent nucleotide incorporation into the same duplex. However, upon removal of the detectable label and the inhibitor group, the nucleotide analog does not substantially hinder subsequent nucleotide (or nucleotide analog) incorporation.

In one aspect, A method for sequencing a nucleic acid. The method includes the steps of: exposing a nucleic acid duplex comprising a template portion and a primer portion to a nucleotide analog comprising an inhibitor that is charged or capable of becoming charged, and a polymerase, under conditions that permit template-dependent incorporation of the analog into the primer; detecting incorporation of the analog; removing or neutralizing the inhibitor; and repeating the exposing, detecting, and removing steps at least once, thereby to determine the sequence of the template.

In another aspect, the invention relates to a nucleotide analog that includes: a nucleoside triphosphate; an inhibitor comprising (a) one or more multiply charged groups or groups capable of becoming multiply charged, or (b) two or more (i.e., a plurality of) singly charged groups or two or more groups capable of becoming singly charged; a detectable label; and a linker connecting the inhibitor and the label to the nucleoside triphosphate. It should be noted that in some embodiments, one or a single charged group may be sufficient to provide the desired inhibitory effect.

In yet another aspect, the invention relates to nucleotide analogs of the formula:

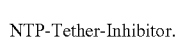

I

NTP is a nucleoside or nucleotide triphosphate or an analog thereof capable of template-dependent incorporation into the 3' end of a polynucleotide strand hybridized to a template. Inhibitor comprises a moiety that is charged or capable of becoming charged and that inhibits subsequent nucleotide incorporation once the first nucleotide is incorporated. Tether is a bond or a group linking the NTP to the Inhibitor group. In a preferred embodiment, the inhibitor is a non-steric inhibitor.

In yet another aspect, the invention relates to nucleotide analogs of Formula II:

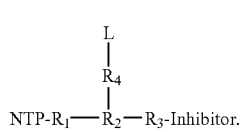

II

NTP is a nucleoside or nucleotide triphosphate or an analog of either capable of template-dependent incorporation into the 3' end of a polynucleotide strand hybridized to a template presenting the complement of the NTP. L is a detectable label that facilitates the identification of the nucleotide analog. Inhibitor comprises (a) one or more multiply charged groups or groups capable of becoming multiply charged, or (b) two or more singly charged groups or two or more groups capable of becoming singly charged. $R_1$ and $R_2$ are independently a bond or a group, wherein at least one of $R_1$ and $R_2$ comprises a cleavable bond, which upon cleavage results in de-association of NTP from both Label and Inhibitor. $R_3$ is a bond or group linking $R_2$ to the Inhibitor. $R_4$ is a bond or group linking $R_2$ to a Label.

In yet another aspect, the invention relates to nucleotide analogs of nucleotide analog of the following Formula II:

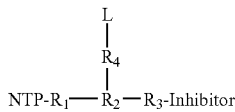

II wherein NTP is a nucleoside or nucleotide triphosphate or an analog of either capable of incorporating onto the 3' end of a polynucleotide strand hybridized to a template presenting the complement of the NTP; L is a detectable label that facilitates the identification of the nucleotide analog; Inhibitor comprises (a) one or more multiply charged groups or groups capable of becoming multiply charged, or (b) two or more singly charged groups or two or more groups capable of becoming singly charged; $R_1$ comprises a cleavable bond, which upon cleavage results in de-association of NTP from both L and Inhibitor; $R_2$ is a tri-valent radical having the formula:

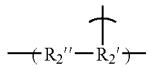

wherein $R_2'$ is a tri-valent radical, and $R_2''$ is a bi-valent radical selected from:

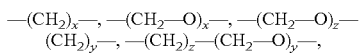

and the same substituted with one or more groups selected from hydroxyl, halogen, amino, thiol, ($C_1$-$C_6$) alkyl, wherein x, y and z are each integers with x and y+z are each from 2 to 10; $R_3$ is a bond or group linking $R_2$ to the Inhibitor moiety; and $R_4$ is a bond or group linking $R_2$ to a L.

In yet another aspect, the invention relates to a method for sequencing a nucleic acid. The method includes: (a) anchoring a nucleic acid duplex, or portion thereof, to a surface, the duplex comprising a template portion and a primer portion hybridized thereto; (b) exposing the duplex to nucleotide analog of Formula I or II (as defined herein) in the presence of a polymerase capable of catalyzing the addition of the nucleotide analog to the primer portion in a template-dependent manner; (c) removing unincorporated nucleotide analog and polymerase; (d) detecting incorporation of the nucleotide analog into the primer portion; and repeating the exposing, removing, and detecting steps at least once.

In yet another aspect, the invention relates to a method for sequencing a nucleic acid, the method comprising the steps of: (a) exposing a nucleic acid duplex comprising a template portion and a primer portion to a nucleotide analog of the following Formula II:

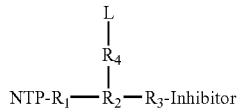

II (b) detecting incorporation of the analog; (c) removing or neutralizing the inhibitor; and (d) repeating the exposing, detecting, and removing steps at least once, thereby to determine the sequence of the template, wherein NTP is a nucleoside or nucleotide triphosphate or an analog of either capable of incorporating onto the 3' end of a polynucleotide strand hybridized to a template presenting the complement of the NTP; L is a detectable label that facilitates the identification of the nucleotide analog; Inhibitor comprises (a) one or more multiply charged groups or groups capable of becoming multiply charged, or (b) two or more singly charged groups or two or more groups capable of becoming singly charged; $R_1$ comprises a cleavable bond, which upon cleavage results in de-association of NTP from both L and Inhibitor; $R_2$ is a trivalent radical having the formula:

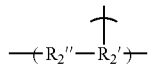

wherein $R_2'$ is a tri-valent radical, and $R_2''$ is a bi-valent radical selected from:

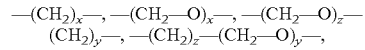

and the same substituted with one or more groups selected from hydroxyl, halogen, amino, thiol, ($C_1$-$C_6$) alkyl, wherein x, y and z are each integers with x and y+z are each from 2 to 10; $R_3$ is a bond or group linking $R_2$ to the Inhibitor moiety; and $R_4$ is a bond or group linking $R_2$ to a L.

In yet another aspect, the invention provides methods and nucleotide analogs for selectively inhibiting the catalytic function of a polymerase enzyme. As such, nucleotide analogs comprise an inhibitory portion, such that the nucleotide analog is capable of being incorporated into a nucleic acid duplex but then inhibits subsequent nucleotide incorporation until the inhibitory portion is removed.

The inhibitory portion of an analog of the invention preferably is a charged group. The charged group can take any appropriate form as long as it carries a charge. Preferably, the charge group is selected from a phosphate, a carboxylic acid (or carboxylate), a sulfate, caproic acid (or a caproic acid derivative), a charged amino acid, —$SO_3$, —$SO_2$, and —$NR_wR_v$, where $R_w$, and $R_w$, independently is H, an alkyl or aryl group. The charged group can convey a negative or positive charge, but negative charged groups are preferred. In another preferred embodiment, the charge group contains multiple charged portions. For example, the charge group can be a dipeptide, a di-phosphate, disulfate, or other multiples of charged moieties. For example, amino acid inhibitors are preferably selected from aspartic acid, glutamic acid, arginine, lysine, and histidine.

The invention provides charged inhibitors of subsequent base incorporation in a sequencing-by-synthesis reaction. By subsequent base incorporation it is intended that a first nucleotide (or analog) is incorporated in a template-dependent manner, but second, third, etc. base incorporation is inhibited by the inhibitor group. In a preferred embodiment, inhibition occurs by positioning a charged group in proximity to the active site of a polymerase enzyme, thus disabling the ability of the polymerase to make subsequent incorporations. Without being limited to theory, analogs of the invention, interfere with magnesium present in the active site of the polymerase, resulting in a reduced ability of the active site to catalyze subsequent nucleotide incorporation.

In a preferred embodiment, an analog of the invention comprises a nucleoside triphosphate, an inhibitor comprising a plurality of charged groups, a detectable label, and a linker connecting the charged groups and the label to the nucleoside triphosphate. Preferred inhibitors comprise a plurality of charged groups and may be selected from any charged group capable of conferring a charge in a local area. Preferably, the inhibitor does not sterically inhibit a polymerase. Also in a preferred embodiment, the linker is cleavable. Multiple cleavable groups, such as enzymatically-cleavable group, such as disulfide bonds and the like.

DETAILED DESCRIPTION OF THE INVENTION

The invention provides methods and compositions that facilitate the addition of a single nucleotide to a template/primer duplex per reaction cycle (i.e., the addition of nucleotides and polymerase enzyme under conditions that result in template-dependent nucleotide incorporation into the primer). Analogs of the invention comprise a charged inhibitory group that, upon incorporation of a nucleotide in a template-dependent manner, prevents subsequent nucleotide incorporation until the inhibitory group is removed. Thus, an analog of the invention comprises a nucleotide triphosphate, a linker (or tether), a detectable label, and a charged inhibitory group, wherein the label and the inhibitory group are removable.

In one aspect, the invention generally provides nucleotide analogs of the following Formula I:

NTP-Tether-Inhibitor     I wherein

NTP is a nucleoside triphosphate or an analog thereof capable of incorporating onto the 3' end of a polynucleotide strand hybridized to a template presenting the complement of the NTP;

Inhibitor comprises a group that is charged or capable of becoming charged, e.g., under reaction conditions, and that inhibits a subsequent incorporation of a nucleotide (or analog thereof), and Tether is a bond or a group linking the NTP to the Inhibitor moiety. A group is considered capable of becoming charged if the group is capable of becoming electrically non-neutral, e.g., under reaction or buffer conditions. Examples of such groups include —COOH and —NR$_w$R$_v$, where R$_w$ and R$_v$ independently is H, an alkyl or aryl group.

In one embodiment, the inhibitor group can cause inhibition of subsequent nucleotide incorporation without steric hinderance. In other words, the inhibition is caused by chemical or charge interaction with the enzyme and not be a physical blocking of the enzyme. In another embodiment, the charged inhibitor also provides steric inhibition of enzyme activity. However, in either case, the inhibitor group is charged.

Natural NTPs include nucleoside triphosphates, adenosine triphosphate (ATP), guanosine triphosphate (GTP), cytidine triphosphate (CTP), thymidine triphosphate (TTP) and uridine triphosphate (UTP); and nucleotide triphosphates, deoxyadenosine triphosphate (dATP), deoxyguanosine triphosphate (dGTP), deoxycytidine triphosphate (dCTP), deoxythimidine triphosphate (dTTP) and deoxyuridine triphosphate (dUTP). NTPs useful in this invention include non-nature nucleosides and nucleotides, and analogs and derivatives thereof.

In some embodiments, the inhibitor may include a moiety that is negatively charged or capable of becoming a negatively charged. In other embodiments, the inhibitor group is positively charged or capable of becoming positively charged.

In some other embodiments, the inhibitor is an amino acid or an amino acid analog. The Inhibitor may be a peptide of 2 to 20 units of amino acids or analogs, a peptide of 2 to 10 units of amino acids or analogs, a peptide of 3 to 7 units of amino acids or analogs, a peptide of 3 to 5 units of amino acids or analogs. In some embodiments, the Inhibitor includes a group selected from the group consisting of Glu, Asp, Arg, His, and Lys, and a combination thereof (e.g., Arg, Arg-Arg, Asp, Asp-Asp, Glu, Glu-Glu, Asp-Glu-Asp, Asp-Asp-Glu or AspAspAspAsp). Peptides or groups may be combinations of the same or different amino acids or analogs.

In one embodiment, the invention relates to an oligonucleotide with at least one nucleotide analog of the invention incorporated therein.

In some embodiments, the Tether comprises

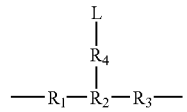

wherein L is detectable label that facilitates the identification of the nucleotide analog after incorporation onto a template;
R$_1$ and R$_2$ are independently a bond or a group, wherein at least one of R$_1$ and R$_2$ comprises a cleavable bond, which upon cleavage results in de-association of NTP from both L and Inhibitor;
R$_3$ is a bond or group linking R$_2$ to the Inhibitor moiety; and
R$_4$ is a bond or group linking R$_2$ to a L.

In another aspect, the present invention is directed to nucleotide analogs of Formula II:

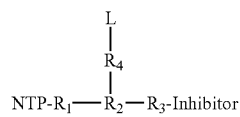

wherein

NTP is a nucleoside triphosphate or an analog thereof capable of incorporating onto the 3' end of a polynucleotide strand hybridized to a template presenting the complement of the NTP;

L is a detectable label to facilitate the identification of the nucleotide analog after incorporation onto the template;

Inhibitor is a moiety that substantially inhibits a subsequent incorporation of a nucleotide (or analog thereof). In some embodiments, the Inhibitor moiety includes a nucleotide or nucleoside or analogs thereof, in other embodiments, the inhibitor is not a nucleotide or analog thereof;

R$_1$ and R$_2$ are independently a bond or a group, wherein at least one of R$_1$ and R$_2$ comprises a cleavable bond, which upon cleavage results in de-association of NTP from both Label and Inhibitor;

R$_3$ is a bond or group linking R$_2$ to the Inhibitor moiety; and
R$_4$ is a bond or group linking R$_2$ to L.

In some embodiments, NTP is a compound having the following formula:

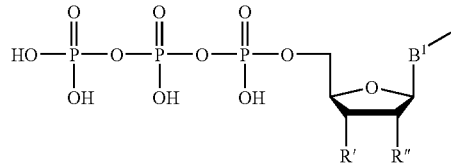

wherein $B^1$ is selected from the group consisting of purine or pyrimidine bases, as well as derivatives of purine and pyrimidine bases; R' is independently selected from the group consisting of —OH, —O—P(O)(OH)$_2$, —O—C(O)—R$^x$, —NHR$^y$, and an —O-blocking agent, where R$^x$ and R$^y$ are alkyl groups; R" is independently selected from the group consisting of H and —OH.

Non-limiting examples of representative purine and pyrimidine bases include adenine, cytosine, guanine, thymine, uracil, or hypoxanthine. Non-limiting examples of derivatives of purine and pyrimidine bases include naturally-occurring and synthetic derivatives of a base, including pyrazolo [3,4-d]pyrimidines, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-propynyl uracil and cytosine, 6-azo uracil, cytosine and thymine, 5-uracil (pseudouracil), 4-thiouracil, 8-halo (e.g., 8-bromo), 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, deazaguanine, 7-deazaguanine, 3-deazaguanine, deazaadenine, 7-deazaadenine, 3-deazaadenine, pyrazolo[3,4-d]pyrimidine, imidazo[1,5-a]1,3,5 triazinones, 9-deazapurines, imidazo[4,5-d]pyrazines, thiazolo[4,5-d]pyrimidines, pyrazin-2-ones, 1,2,4-triazine, pyridazine; and 1,3,5 triazine.

Base $B^1$ of the invention permits a nucleotide to be incorporated into a polynucleotide chain by a polymerase and forms base pairs with a base on an antiparallel nucleic acid strand. The term base pair encompasses not only the standard AT, AU or GC base pairs, but also base pairs formed between nucleotides and/or nucleotide analogs comprising non-standard or modified bases, wherein the arrangement of hydrogen bond donors and hydrogen bond acceptors permits hydrogen bonding between a nonstandard base and a standard base or between two complementary non-standard base structures. One example of such non-standard base pairing is the base pairing between the nucleotide analog inosine and adenine, cytosine or uracil, where two hydrogen bonds are formed.

The Inhibitor may include a charged moiety (e.g., a negatively charged moiety, a positively charged moiety, or both) or a moiety that is capable of becoming charged. The Inhibitor can include two or more charged groups. The Inhibitor may have a charged group selected from the group consisting of —COOH, —PO$_4$, —SO$_4$, —SO$_3$, —SO$_2$, —NR$_w$R$_v$, where R$_w$, and R$_v$ independently is H, an alkyl or aryl group. In other embodiments, the Inhibitor moiety does not comprise a —PO$_4$ group. In some other embodiments, the Inhibitor moiety does not comprise an aryl group. In certain other embodiments, the Inhibitor does not include a nucleotide or nucleoside or analogs thereof.

Inhibitor may be a compound having the following formula:

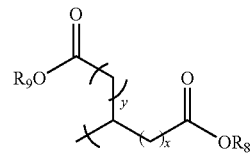

wherein $R_8$ and $R_9$ independently is a H or an alkyl group; each of x and y is an integer from 0 to about 5. In some embodiments, $R_8$ and $R_9$ are H atoms and x=1 and y=2.

$R_3$ of a nucleotide analog of Formula II may include a group having the formula of

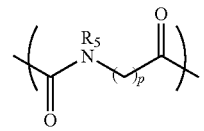

wherein $R_5$ is a H or an alkyl group; p is an integer from 0 to about 10. In some embodiments, p is 5 or 6.

In some embodiments, $R_3$ of a nucleotide analog of Formula II may include a group having the formula of

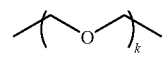

wherein k is an integer from about 1 to about 5. In some embodiments, k is an integer from about 2 to about 4. In some embodiments, k is 3.

In some embodiments, $R_3$ of a nucleotide analog of Formula II may include a group having the formula of

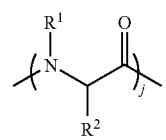

wherein $R^1$, $R^2$ are independently H or alkyl groups, and may together form one or more 3, 4, 5, or 6-member rings, and j is an integer from about 1 to about 5. In some embodiments, $R_3$ of include a group having the formula of

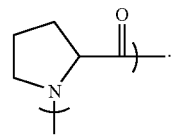

In some embodiments, $R_1$ of a nucleotide analog of Formula II may include a group having the formula of

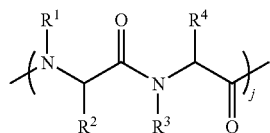

wherein $R^1$, $R^2$, $R^3$, and $R^4$ are independently H or alkyl groups, and two or more of which may together form one or more 3, 4, 5, or 6-member rings, and j is an integer from about 1 to about 3.

In some embodiments, $R^1$ of include a group having the formula of

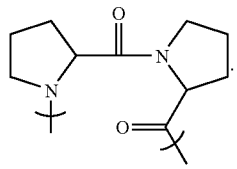

$R^1$ of a nucleotide analog of Formula II may include a C—C triple bond, a S—S bond, or both a C—C triple bond and a S—S bond.

In some embodiments, $R_1$ in the nucleotide analog of Formula II includes a group having the formula of

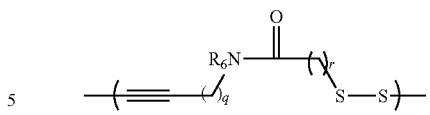

wherein $R_6$ is a H or an alkyl group; q and r independently is an integer from about 1 to about 10.

In some embodiments, q is 1 or 2 and r is 1, 2 or 3.

In some embodiments, $R_2$ is a tri-valent radical having the formula:

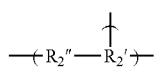

wherein
$R_2'$ is a tri-valent radical, and
$R_2''$ is a bi-valent radical selected from:
—(CH$_2$)$_x$—, —(CH$_2$—O)$_x$—, —(CH$_2$—O)$_z$—(CH$_2$)$_y$—, —(CH$_2$)$_z$—(CH$_2$—O)$_y$—,
and the same substituted with one or more groups selected from hydroxyl, halogen, amino, thiol, (C$_1$-C$_6$) alkyl,
wherein x, y and z are each integers with x and y+z are each from 2 to 10.

In some detailed embodiments, $R_2''$ is —(CH$_2$)$_x$— or —(CH$_2$—O)$_x$—, where x is 2, 3, 4, 5, or 6. In some other detailed embodiments, $R_2''$ is —(CH$_2$—O)$_x$—(CH$_2$)$_y$— or —(CH$_2$)$_z$—(CH$_2$—O)$_y$—, where y+z is 2, 3, 4, 5, or 6. Advantages of these analogs include increased stability and enhanced level of inhibition, allowing more optimal spacing of the inhibitor moiety within/on the polymerase to increase effective inhibition. Exemplary compounds include:

TABLE 1

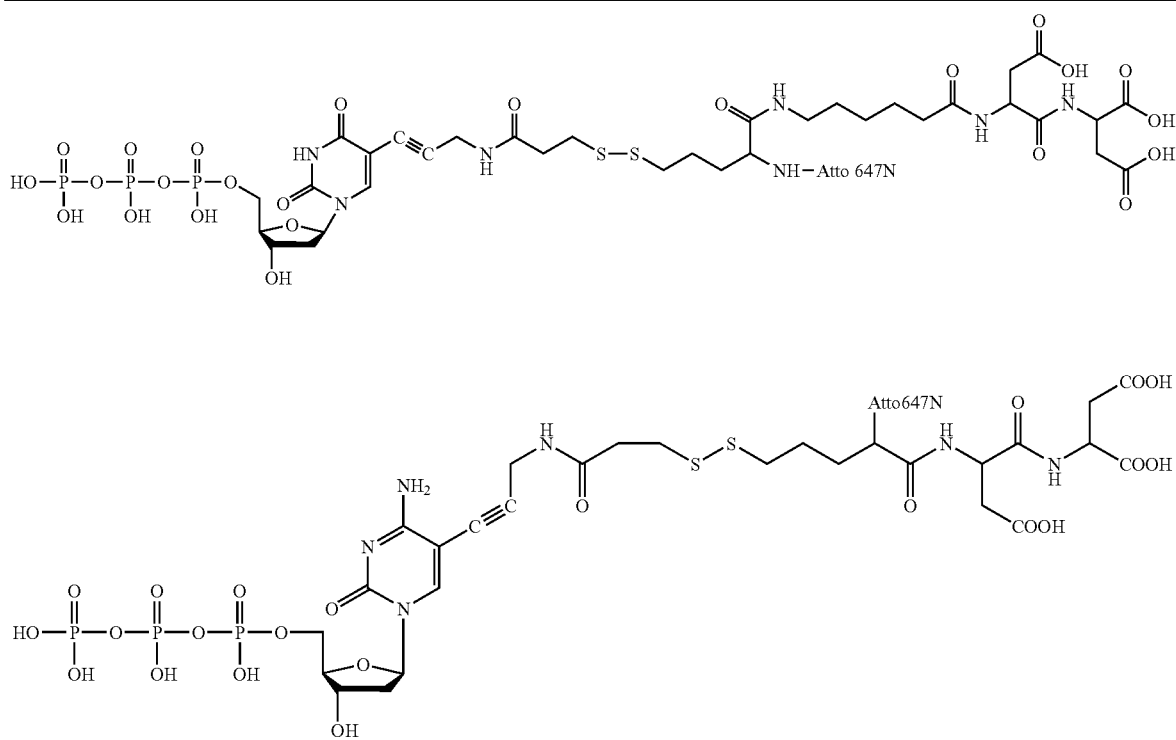

TABLE 1-continued

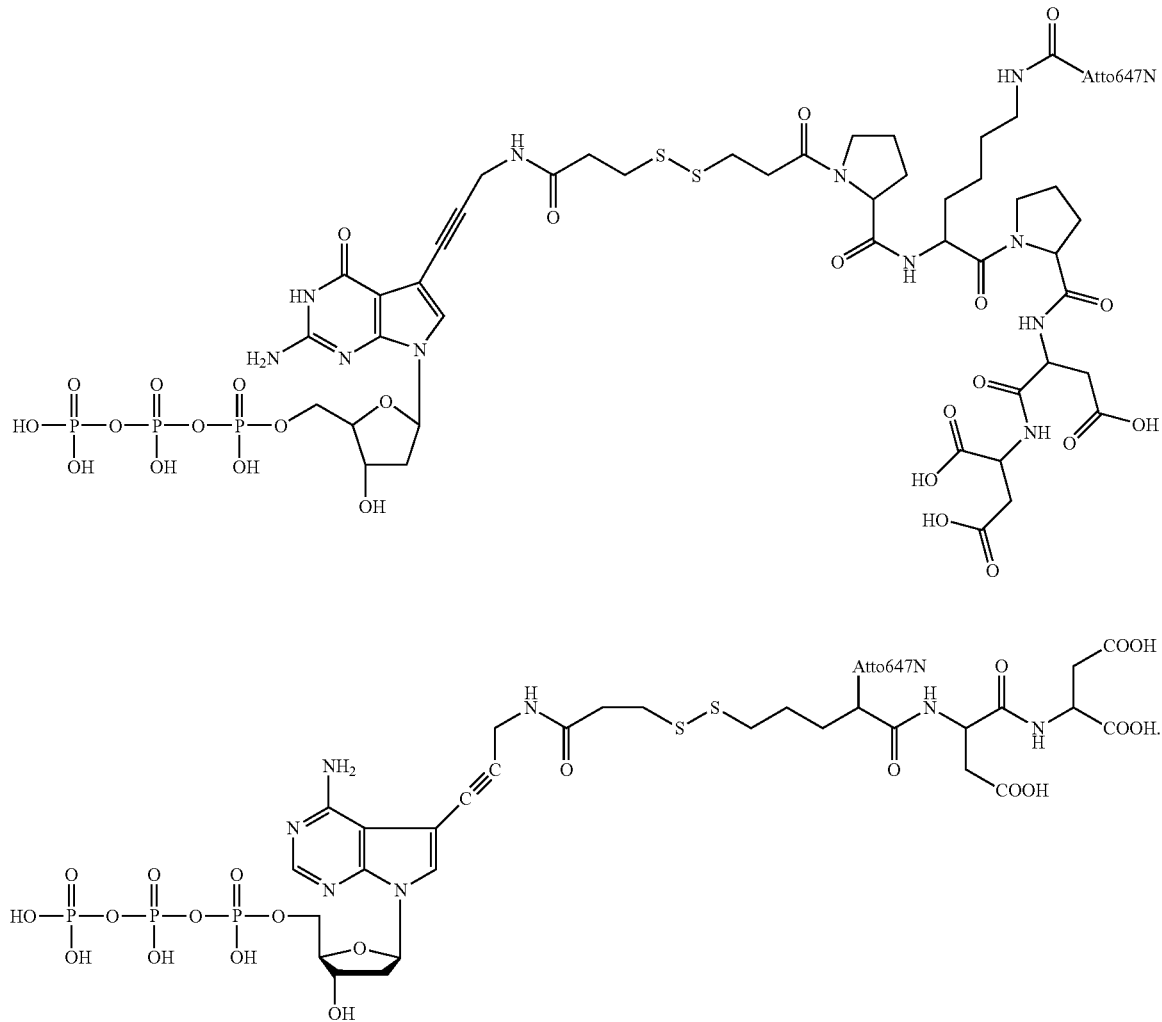

In some embodiments of the invention, the location of the charged moiety within the inhibitor group and/or the distance of the charged group to the NTP plays an important role in the effectiveness of inhibiting a subsequent nucleotide incorporation. In some embodiments, the charged moiety of the inhibitor is from about 5 to about 60 bonds away from the NTP. In some other embodiments, the charged moiety of the inhibitor is from about 10 to about 40 bonds away from the NTP. In some other embodiments, the charged moiety of the inhibitor is from about 10 to about 35 bonds away from the NTP. In some other embodiments, the charged moiety of the inhibitor is from about 10 to about 30 bonds away from the NTP. In some other embodiments, the charged moiety of the inhibitor is from about 10 to about 20 bonds away from the NTP.

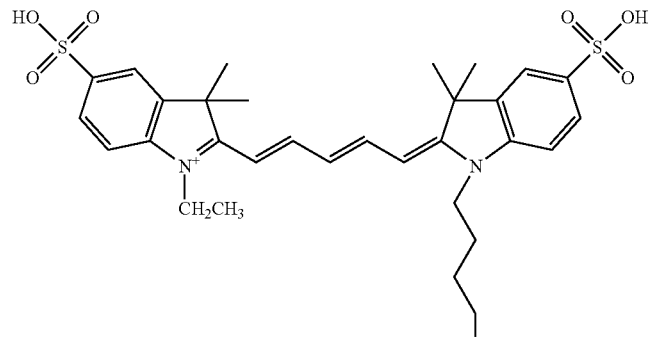

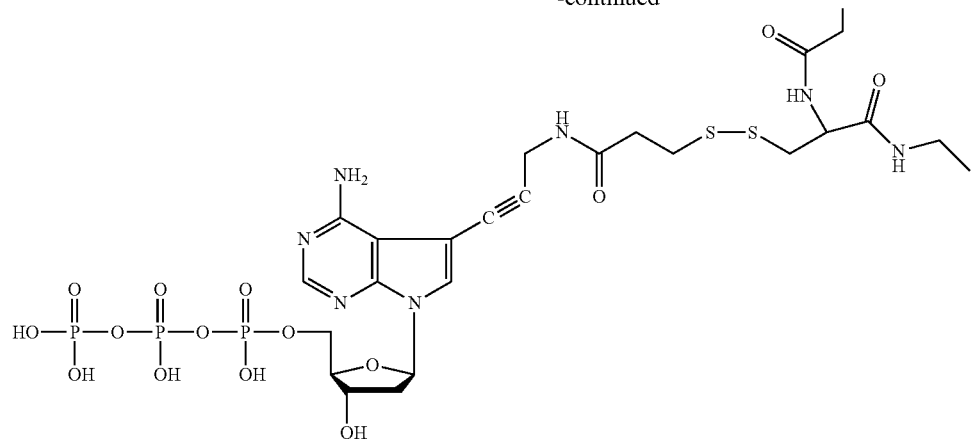
$C_{71}H_{97}N_{10}O_{29}P_4S_4^+$
Exact Mass: 1805.43
For example, the above compound (about 17× fold inhibition) exhibits an inhibiting effect that is much less than the following compound (about 70× fold inhibition).
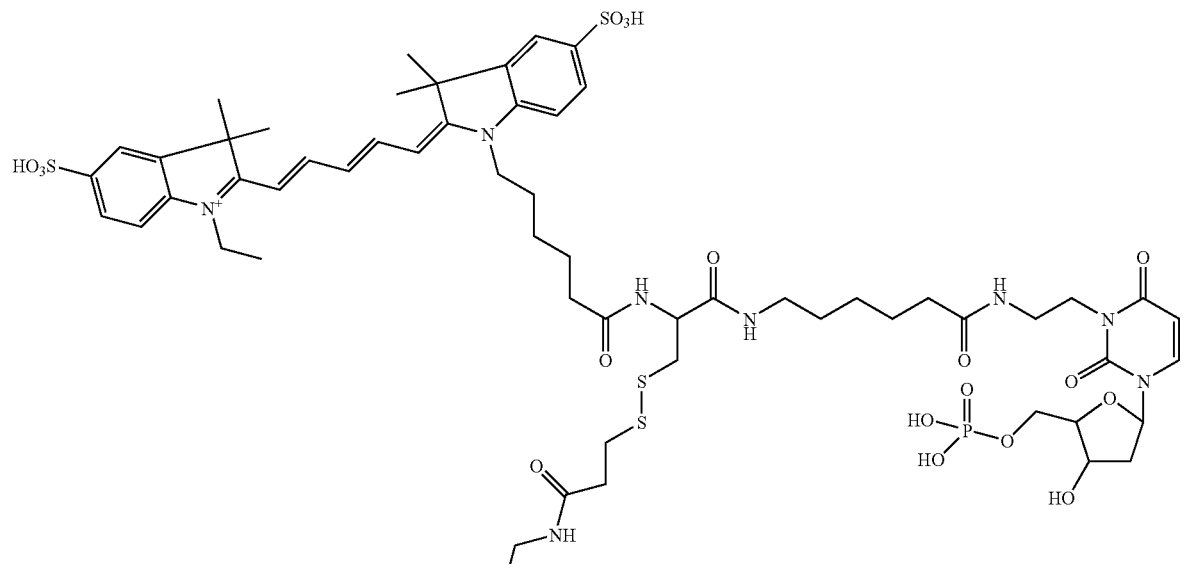

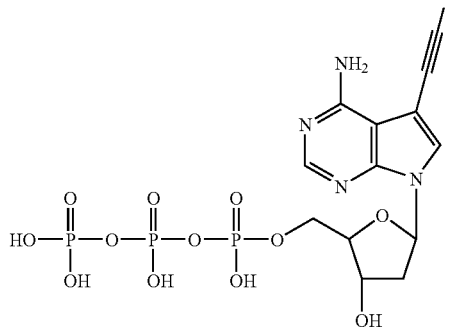

C₇₀H₉₅N₁₂O₃₀P₄S₄⁺
Exact Mass: 1835.41
Mol. Wt.: 1836.72

The label (or "L") may be any moiety that can be attached to or associated with, e.g., directly or via a linker or spacer, an oligonucleotide and that functions to provide a detectable signal, and/or to interact with a second label to modify the detectable signal provided by the first or second label, e.g. fluorescence resonance energy transfer (FRET). In one embodiment, the label is an optically-detectable moiety (e.g., a fluorophore). Non-limiting examples of types of optically-detectable labels include a fluorescent, chemiluminescence, or electrochemically luminescent label. Examples of fluorescent labels include, but are not limited to, 4-acetamido-4'-isothiocyanatostilbene-2,2'disulfonic acid; acridine and derivatives thereof such as acridine, acridine isothiocyanate; 5-(2'-aminoethyl)aminonaphthalene-1-sulfonic acid (EDANS); 4-amino-N-[3-vinylsulfonyl)phenyl]naphthalimide-3,5disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5',5''-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivatives of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700; IRD 800; La Jolta Blue; phthalocyanine; naphthalocyanine; any of the fluorescent labels available from Atto-Tec, such as Atto 390, Atto 425, Atto 465, Atto 488, Atto 495, Atto 520, Atto 532, Atto 550, Atto 565, Atto 590, Atto 594, Atto 610, Atto 611X, Atto 620, Atto 633, Atto 635, Atto 637, Atto 647, Atto 647N, Atto 655, Atto 680, Atto 700, Atto 725, Atto 740, etc.; any of the fluorescent labels available from Dyomics such as DY-630, DY-631, DY-632, DY-633, DY-634, DY-635, DY-636, Dy-647, Dy-648, DY-649, Dy-650, Dy-651, DY-652, etc.; any of the fluorescent labels available from Pierce such as DyLight 405, DyLight 488, DyLight 549, DyLight 633, DyLight 649, DyLight 680, DyLight 800, etc.; any of the fluorescent labels available from AnaSpec such as HiLyte Fluor™ 488 dyes, HiLyte Fluor™ 555 dyes, HiLyte Fluor™ 647 dyes, HiLyte Fluor™ 680 dyes, HiLyte Fluor™ 750 dyes, HiLytePlus™ 555 dyes, HiLytePlus™ 647 dyes, HiLytePlus™ 750 dyes, etc.; any of the fluorescent labels available from Denovo Biolables such as Oyster 500, Oyster 550 P, Oyster 550 D, Oyster 556, Oyster 645, Oyster 650 P, Oyster 650 D, Oyster 656, etc.; IRDye® 680, IRDye® 700, IRDye® 700DX, IRDye® 800, IRDye® 800 RS, IRDye® 800 CW, etc.; any of the fluorescent labels available from SETA Biomedicals such as Seta K1-204, Seta K5-3212, Seta K8-1342, Seta K8-1352, Seta K8-1357, Seta K8-1407, Seta K8-1642, Seta K8-1644, Seta K8-1663, Seta K8-1664, Seta K8-1669, Seta K8-3002, Seta K4-1082, Seta K8-1669, Seta K7-545, Seta K7-547, Seta K7-549, Seta K8-1252, Seta K8-1261, Seta K8-1262, Seta K8-1320, Seta K8-1344, Seta K8-1367, Seta K8-1377, Seta K8-1382, Seta K8-1446, Seta K8-1667, Seta K8-1752, Seta K8-1762, Seta K8-1767, Seta K8-1777, Seta K8-1782, etc.; Q Dots; and dyes having the following structures:

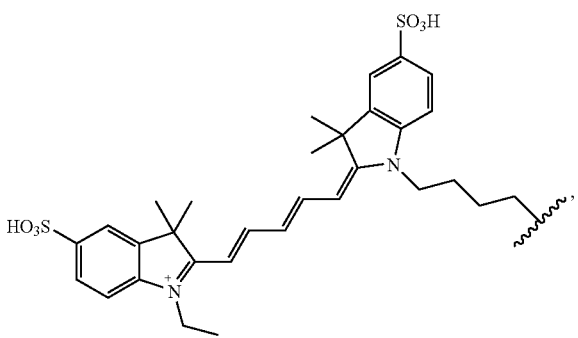

-continued

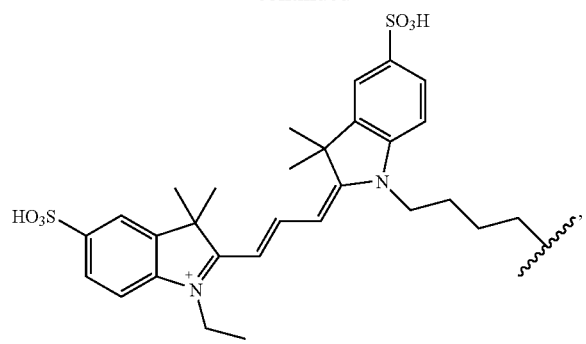

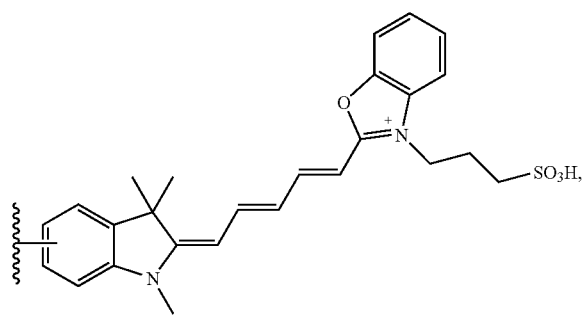

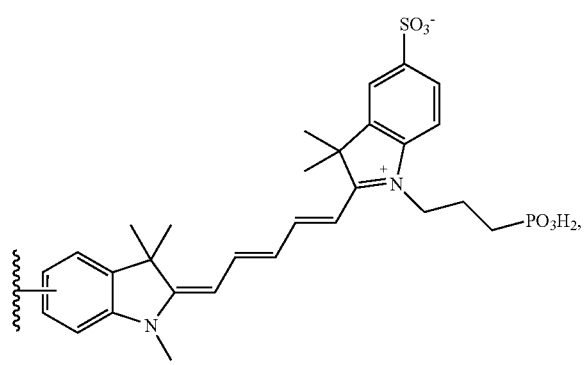

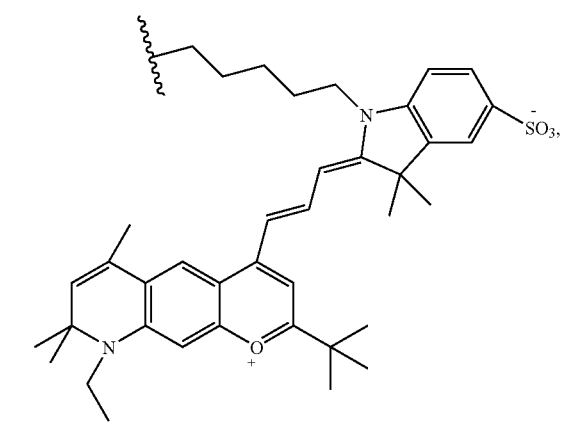

-continued

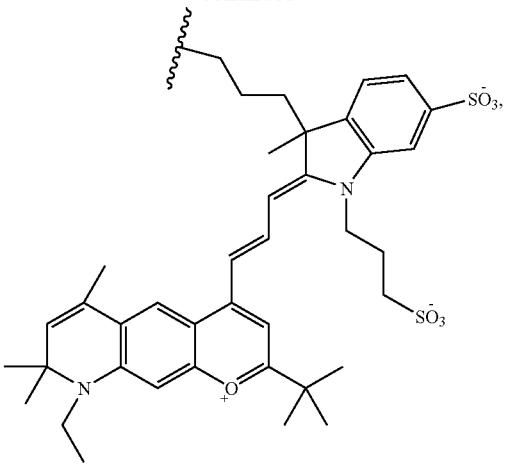

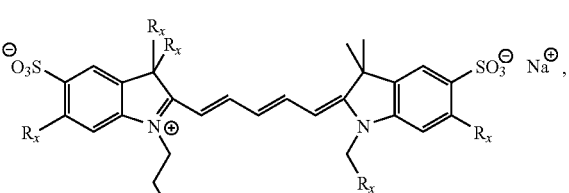

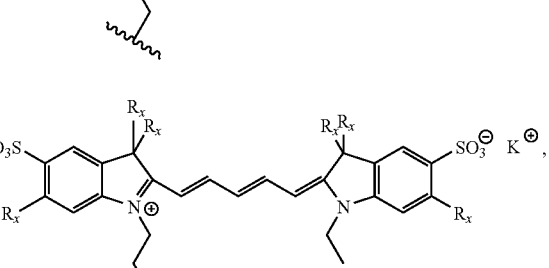

wherein each $R_x$ is independently selected from the group consisting of H, alkyl, and substituted alkyl.

The above exemplary label moieties include any derivatives containing the chromophore of any of the labeling moieties exemplified or described herein, attached to the nucleotide analog by means of any suitable chemical linking group. For example, the chromophore can be attached to the nucleotide analog via an alkyl chain bonded to the nucleotide analog by a functional group such as an amide, ester, ether, amine, thiol, disulfide, urea, urethane, carbonate, etc. In one embodiment, the label is a fluorescent label such as cyanine-3 and cyanine-5.

Labels other than fluorescent labels are contemplated as part of the invention, including other optically-detectable labels. Any appropriate detectable label can be used according to the invention, and numerous other labels are known to those skilled in the art.

The invention also relates to methods for nucleic acid sequence determination using the nucleotide analogs described herein. The nucleotide analogs of the invention are particularly suitable for use in single molecule sequencing techniques. Such techniques are described for example in U.S. patent application Ser. No. 10/831,214 filed April 2004; Ser. No. 10/852,028 filed May 24, 2004; Ser. No. 10/866,388 filed Jun. 10, 2005; Ser. No. 10/099,459 filed Mar. 12, 2002; and U.S. Published Application 2003/013880 published Jul. 24, 2003, each of which is herein incorporated in its entirety for all purposes. In general, methods for nucleic acid sequence determination include exposing a target nucleic acid (also referred to herein as template nucleic acid or template) to a primer that is complementary to at least a portion of the target nucleic acid, under conditions suitable for hybridizing the primer to the target nucleic acid, forming a template/primer duplex.

The invention also relates to methods for nucleic acid sequence determination using the nucleotide analogs described herein. The nucleotide analogs of the invention are particularly suitable for use in single molecule sequencing techniques. Such techniques are described for example in U.S. patent application Ser. No. 10/831,214 filed April 2004; Ser. No. 10/852,028 filed May 24, 2004; Ser. No. 10/866,388 filed Jun. 10, 2005; Ser. No. 10/099,459 filed Mar. 12, 2002; and U.S. Published Application 2003/013880 published Jul. 24, 2003, each of which is herein incorporated in its entirety for all purposes. In general, methods for nucleic acid sequence determination include exposing a target nucleic acid (also referred to herein as template nucleic acid or template) to a primer that is complementary to at least a portion of the target nucleic acid, under conditions suitable for hybridizing the primer to the target nucleic acid, forming a template/primer duplex.

In another aspect, the invention relates to a method for sequencing a nucleic acid. The method includes: (a) anchoring a nucleic acid duplex to a surface, the duplex comprising a template portion and a primer portion hybridized thereto; (b) exposing the duplex to nucleotide analog of Formula I or Formula II in the presence of a polymerase capable of catalyzing the addition of the nucleotide analog to the primer portion in a template-dependent manner; (c) removing unincorporated nucleotide analog and polymerase; (d) detecting incorporation of the nucleotide analog into the primer portion; and (e) repeating said exposing, removing, and detecting steps at least once. The method may further include cleaving L from the nucleotide analog after the detecting step.

In another aspect, the invention relates to a method for inhibiting the catalytic function of a polymerase enzyme in a sequencing-by-synthesis reaction comprising introducing a nucleotide attached to an inhibitory group. In one aspect, the invention comprises attaching one or both members of a template/primer duplex to a surface, introducing a polymerase and a nucleotide analog comprising a charged inhibitor under conditions sufficient for template-dependent incorporation of the nucleotide and inhibition of subsequent incorporation. Such methods further comprise removing or neutralizing the inhibitor in order to facilitate further nucleotide incorporation. Finally, nucleotides of the invention can be detectably labeled to monitor incorporation.

Target nucleic acids include deoxyribonucleic acid (DNA) and/or ribonucleic acid (RNA). Target nucleic acid molecules can be obtained from any cellular material obtained from an animal, plant, bacterium, virus, fungus, or any other cellular organism, or may be synthetic DNA. Target nucleic acids may be obtained directly from an organism or from a biological sample obtained from an organism, e.g., from blood, urine, cerebrospinal fluid, seminal fluid, saliva, sputum, stool and tissue. Any tissue or body fluid specimen may be used as a source for nucleic acid for use in the invention. Nucleic acid molecules may also be isolated from cultured cells, such as a primary cell culture or a cell line. The cells from which target nucleic acids are obtained can be infected with a virus or other intracellular pathogen. Nucleic acid molecules may also include those of animal (including human), wild type or engineered prokaryotic or eukaryotic cells, viruses or completely or partially synthetic RNAs or DNAs. A sample can also be total RNA extracted from a biological specimen, a cDNA library, or genomic DNA.

Nucleic acid typically is fragmented to produce suitable fragments for analysis. In one embodiment, nucleic acid from a biological sample is fragmented by sonication. Test samples can be obtained as described in U.S. Patent Application 2002/0190663 A1, published Oct. 9, 2003, herein incorporated by reference in its entirety for all purposes. Generally, nucleic acid can be extracted from a biological sample by a variety of techniques such as those described by Maniatis, et al., Molecular Cloning: A Laboratory Manual, Cold Spring Harbor, N.Y., pp. 280-281 (1982). Generally, target nucleic acid molecules can be from about 5 bases to about 20 kb, about 30 kb, or even about 40 kb or more. Nucleic acid molecules may be single-stranded, double-stranded, or double-stranded with single-stranded regions (for example, stem- and loop-structures)

Single molecule sequencing includes a template nucleic acid molecule/primer duplex that is immobilized on a surface such that the duplex and/or the nucleotides (or nucleotide analogs) added to the immobilized primer are individually optically resolvable. The primer, template and/or nucleotide analogs are detectably labeled such that the position of an individual duplex molecule is individually optically resolvable. Either the primer or the template is immobilized to a solid support. The primer and template can be hybridized to each other and optionally covalently cross-linked prior to or after attachment of either the template or the primer to the solid support.

In general, methods for facilitating the incorporation of a nucleotide analog as an extension of a primer include exposing a target nucleic acid/primer duplex to one or more nucleotide analogs disclosed herein and a polymerase under conditions suitable to extend the primer in a template dependent manner. Generally, the primer is sufficiently complementary to at least a portion of the target nucleic acid to hybridize to the target nucleic acid and allow template-dependent nucleotide polymerization. The primer extension process can be repeated to identify additional nucleotide analogs in the template. The sequence of the template is determined by compiling the detected nucleotides, thereby determining the complementary sequence of the target nucleic acid molecule.

Any polymerase and/or polymerizing enzyme may be employed. A preferred polymerase is Klenow with reduced exonuclease activity. Nucleic acid polymerases generally useful in the invention include DNA polymerases, RNA polymerases, reverse transcriptases, and mutant or altered forms of any of the foregoing. DNA polymerases and their properties are described in detail in, among other places, DNA Replication 2nd edition, Kornberg and Baker, W. H. Freeman, New York, N.Y. (1991). Known conventional DNA polymerases useful in the invention include, but are not limited to, *Pyrococcus furiosus* (Pfu) DNA polymerase (Lundberg et al., 1991, Gene, 108: 1, Stratagene), *Pyrococcus woesei* (Pwo) DNA polymerase (Hinnisdaels et al., 1996, Biotechniques, 20: 186-8, Boehringer Mannheim), *Thermus thermophilus* (Tth) DNA polymerase (Myers and Gelfand 1991, Biochemistry 30:7661), *Bacillus stearothermophilus* DNA polymerase (Stenesh and McGowan, 1977, Biochim Biophys Acta 475:32), *Thermococcus litoralis* (Tli) DNA polymerase (also referred to as Vent™ DNA polymerase, Cariello et al., 1991, Polynucleotides Res, 19: 4193, New England Biolabs), 9"NM™ DNA polymerase (New England Biolabs), Stoffel fragment, Thermosequenase® (Amersham Pharmacia Biotech UK), Therminator™ (New England Biolabs), *Thermotoga maritima* (Tma) DNA polymerase (Diaz and Sabino, 1998 Braz J. Med. Res, 31:1239), *Thermus aquaticus* (Taq) DNA polymerase (Chien et al., 1976, J. Bacteoriol, 127: 1550), DNA polymerase, *Pyrococcus* kodakaraensis KOD DNA polymerase (Takagi et al., 1997, Appl. Environ. Microbiol. 63:4504), JDF-3 DNA polymerase (from *thermococcus* sp. JDF-3, Patent application WO 0132887), *Pyrococcus* GB-D (PGB-D) DNA polymerase (also referred as Deep VentTMD NA polymerase, Juncosa-Ginesta et al., 1994, Biotechniques, 16:820, New England Biolabs), UlTma DNA polymerase (from thermophile *Thermotoga maritima*; Diaz and Sabino, 1998 Braz J. Med. Res, 31:1239; PE Applied Biosystems), Tgo DNA polymerase (from *thermococcus gorgonarius*, Roche Molecular Biochemicals), *E. coli* DNA polymerase I (Lecomte and Doubleday, 1983, Polynucleotides Res. 11:7505), T7 DNA polymerase (Nordstrom et al., 1981, J. Biol. Chem. 256:3112), and archaeal DP1I/DP2 DNA polymerase II (Cann et al., 1998, Proc Natl Acad. Sci. USA 95: 14250-5).

Other DNA polymerases include, but are not limited to, ThermoSequenase® 9° Nm™, Therminator™, Taq, Tne, Tma, Pfu, Tfl, Tth, Tli, Stoffel fragment, Vent™ and Deep Vent™ DNA polymerase, KOD DNA polymerase, Tgo, JDF-3, and mutants, variants and derivatives thereof. Reverse transcriptases useful in the invention include, but are not limited to, reverse transcriptases from HIV, HTLV-1, HTLV-11, FeLV, FIV, SIV, AMV, MMTV, MoMuLV and other retroviruses (see Levin, Cell 88:5-8 (1997); Verma, Biochim Biophys Acta. 473:1-38 (1977); Wu et al., CRC Crit. Rev. Biochem. 3:289-347 (1975)).

Unincorporated nucleotide analog molecules may be removed prior to or after detecting. Unincorporated nucleotide analog molecules may be removed by washing.

A template/primer duplex is treated to remove the label and/or to cleave the molecular chain attaching the label to the nucleotide. One may repeat the steps of exposing template/primer duplex to one or more nucleotide analogs and polymerase, detecting incorporated nucleotides, and then treating to (1) remove the label, (2) remove the label and at least a portion of the molecular chain associating the label to the nucleotide or (3) cleave the molecular chain thereby identifying additional bases in the template nucleic acid, The identified bases can be compiled to determine the sequence of the target nucleic acid. In some embodiments, at least some portions of the remaining molecular chain and/or label are not removed, for example, in the last round of primer extension.

In some embodiments, a nucleotide analog, after removal of the label and portions of the molecular chain connecting the label to the nucleotide can be represented by:

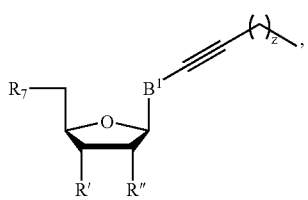

wherein $B^1$, R', R", are as described herein, and z is an integer from about 1 to about 12. $R^7$ is a phosphodiester linkage connecting the nucleotide analog to a sugar of an adjacent nucleotide in the nucleic acid, or a phosphoryl group. In some embodiments, z is an integer from about 1 to about 5. In some other embodiments, z is an integer from about 1 to about 3.

The invention also provides for a method of removing a label from a labeled base, comprising (a) exposing a base of Formula I or Formula II:

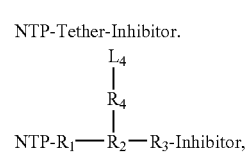

as described herein, to a reducing agent for a time sufficient to produce an unlabelled base of Formula III:

where $B^1$ is a part of the NTP of a nucleotide analog in Formula I or Formula II, and n is an integer from about 1 to about 12. In some embodiments, the reducing agent is tris (2-carboxyl ethyl) phosphine. In other embodiments, the base is linked to a sugar selected from the group consisting of ribose, deoxyribose, and analogs thereof, where the base and sugar together may be present in a nucleotide in a nucleic acid.

One embodiment of a method for sequencing a nucleic acid template includes exposing a nucleic acid template to a primer capable of hybridizing to the template, a polymerase capable of catalyzing nucleotide addition to the primer, and a labeled nucleotide analog disclosed herein under conditions to permit the polymerase to add the nucleotide analog to the primer. A method for sequencing may further include identifying or detecting the incorporated labeled nucleotide. A cleavable bond may then be cleaved, removing at least the label from the nucleotide analog. The exposing, detecting, and removing steps are repeated at least once. In certain embodiments, the exposing, detecting, and removing steps are repeated at least three, five, ten or even more times. The sequence of the template can be determined based upon the order of incorporation of the labeled nucleotides.

In another embodiment, a method for sequencing a nucleic acid template includes exposing a nucleic acid template to a primer capable of hybridizing to the template and a polymerase capable of catalyzing nucleotide addition to the primer. The polymerase is, for example, Klenow with reduced exonuclease activity. The polymerase adds a labeled nucleotide analog disclosed herein. The method may include identifying the incorporated labeled nucleotide. Once the labeled nucleotide is identified, the label and at least a portion of a molecular chain connecting the label to the nucleotide analog are removed and the remaining portion of the molecular chain includes a free hydroxyl group. The exposing, incorporating, identifying, and removing steps are repeated at least once, preferably multiple times depending on the application. The sequence of the template is determined based upon the order of incorporation of the labeled nucleotides.

Removal of a label from a labeled nucleotide analog and/or cleavage of the molecular chain linking a nucleotide analog to a label may include contacting or exposing the labeled nucleotide with a reducing agent. Such reducing agents include, for example, dithiothreitol (DTT), tris(2-carboxyethyl)phosphine (TCEP), tris(3-hydroxy-propyl) phosphine, tris(2-chloropropyl) phosphate (TCPP), 2-mercaptoethanol, 2-mercaptoethylamine, cystein and ethylmaleimide. Such contacting or exposing the reducing agent to a labeled nucleotide analog may occur at a range of pH values, for example at a pH of about 5 to about 10, or about 7 to about 9.

The above-described methods for sequencing a nucleic acid template can further include a step of capping a molecular chain, for example, after the label has been removed. After addition of the nucleotide analog to the primer, any optional 3' phosphate moiety can be removed enzymatically. In one embodiment, an optional phosphate can be removed using alkaline phosphatase or $T_4$ polynucleotide kinase. Suitable enzymes for removing optional phosphate include, any phosphatase, for example, alkaline phosphatase such as shrimp alkaline phosphatase, bacterial alkaline phosphatase, or calf intestinal alkaline phosphatase.

Any suitable detection method may be used to identify an incorporated nucleotide analog. Thus, exemplary detection methods include radioactive detection, optical absorbance detection, e.g., UV-visible absorbance detection, optical emission detection, e.g., fluorescence or chemiluminescence. Single-molecule fluorescence can be carried out using a conventional microscope equipped with total internal reflection (TIR) objective. The detectable moiety associated with the extended primers can be detected on a substrate by scanning all or portions of each substrate simultaneously or serially, depending on the scanning method used. For fluorescence labeling, selected regions on a substrate may be serially scanned one-by-one or row-by-row using a fluorescence microscope apparatus, such as described in Fodor (U.S. Pat. No. 5,445,934) and Mathies et al. (U.S. Pat. No. 5,091,652). Devices capable of sensing fluorescence from a single molecule include scanning tunneling microscope (STM) and the atomic force microscope (AFM). Hybridization patterns may also be scanned using a CCD camera (e.g., Model TE/CCD512SF, Princeton Instruments, Trenton, N.J.) with suitable optics (Ploem, CCD (Chase-Completed-Device) in Fluorescent and Luminescent Probes for Biological Activity Mason, T. G. Ed., Academic Press, Landon, pp. 1-11 (1993), such as described in Yershov et al., Proc. Natl. Aca. Sci. 93:4913 (1996), or may be imaged by TV monitoring. For radioactive signals, a phosphorimager device can be used (Johnston et al., Electrophoresis, 13566, 1990; Drmanac et al., Electrophoresis, 13:566, 1992; 1993). Other commercial suppliers of imaging instruments include General Scanning Inc., (Watertown, Mass. on the World Wide Web at genscan.com), Genix Technologies (Waterloo, Ontario, Canada; on the World Wide Web at confocal.com), and Applied Precision Inc. Such detection methods are particularly useful to achieve simultaneous scanning of multiple attached target nucleic acids.

The present invention provides for detection of molecules ranging from a single nucleotide to a single target nucleic acid molecule. A number of methods are available for this purpose. Methods for visualizing single molecules within nucleic acids labeled with an intercalating dye include, for example, fluorescence microscopy. For example, the fluorescent spectrum and lifetime of a single molecule excited-state can be measured. Standard detectors such as a photomultiplier tube or avalanche photodiode can be used. Full field imaging with a two-stage image intensified CCD camera also can be used. Additionally, low noise cooled CCD can also be used to detect single fluorescent molecules.

The detection system for the signal may depend upon the labeling moiety used. For optical signals, a combination of an optical fiber or charge coupled device (CCD) can be used in the detection step. In those circumstances where the substrate is itself transparent to the radiation used, it is possible to have an incident light beam pass through the substrate with the detector located opposite the substrate from the target nucleic acid. For electromagnetic labeling moieties, various forms of spectroscopy systems can be used. Various physical orientations for the detection system are available and discussion of design parameters is provided in the art.

A number of approaches can be used to detect incorporation of fluorescently labeled nucleotides into a single nucleic acid molecule. Optical setups include near-field scanning microscopy, far-field confocal microscopy, wide-field epi-illumination, but are not limited to, light scattering, dark field microscopy, photoconversion, single and/or multiphoton excitation, spectral wavelength discrimination, fluorophore identification, evanescent wave illumination, and total internal reflection fluorescence (TIRF) microscopy. In general, certain methods involve detection of laser-activated fluorescence using a microscope equipped with a camera. Suitable photon detection systems include, but are not limited to, photodiodes and intensified CCD cameras. For example, an intensified charge couple device (ICCD) camera can be used. The use of an ICCD camera to image individual fluorescent dye molecules in a fluid near a surface provides numerous advantages. For example, with an ICCD optical setup, it is possible to acquire a sequence of images (movies) of fluorophores.

Some embodiments of the present invention use TIRF microscopy for two-dimensional imaging. TIRF microscopy uses totally internally reflected excitation light and is well known in the art. See, e.g., the World Wide Web at nikoninstruments.jp/eng/page/products/tirf.aspx. In certain embodiments, detection is carried out using evanescent wave illumination and total internal reflection fluorescence microscopy. An evanescent light field can be set up at the surface, for example, to image fluorescently-labeled nucleic acid molecules. When a laser beam is totally reflected at the interface between a liquid and a solid substrate (e.g., a glass), the excitation light beam penetrates only a short distance into the liquid. The optical field does not end abruptly at the reflective interface, but its intensity falls off exponentially with distance. This surface electromagnetic field, called the "evanescent wave", can selectively excite fluorescent molecules in the liquid near the interface. The thin evanescent optical field at the interface provides low background and facilitates the detection of single molecules with high signal-to-noise ratio at visible wavelengths.

The evanescent field also can image fluorescently-labeled nucleotides upon their incorporation into the attached target nucleic acid target molecule/primer complex in the presence of a polymerase. Total internal reflectance fluorescence microscopy is then used to visualize the attached target nucleic acid target molecule/primer complex and/or the incorporated nucleotides with single molecule resolution.

Fluorescence resonance energy transfer (FRET) can be used as a detection scheme. FRET in the context of sequencing is described generally in Braslavasky, et al., Proc. Nat'l Acad. Sci., 100: 3960-3964 (2003), incorporated by reference herein. In an embodiment, a donor fluorophore is attached to the primer, polymerase, or template. Nucleotides added for incorporation into the primer comprise an acceptor fluorophore that is activated by the donor when the two are in proximity.

Measured signals can be analyzed manually or preferably by appropriate computer methods to tabulate results. Preferably, the signals of millions of analogs are read in parallel and then deconvoluted to ascertain a sequence. The substrates and reaction conditions can include appropriate controls for verifying the integrity of hybridization and extension conditions, and for providing standard curves for quantification, if desired. For example, a control nucleic acid can be added to the sample. The absence of the expected extension product is an indication that there is a defect with the sample or assay components requiring correction.

As another example, the described nucleotide analogs can be used to facilitate "four color" sequencing by synthesis if each base (A, C, G, T) is labeled with a dye emitting and/or absorbing at a different and resolvable wavelength. The sequencing procedure can be shortened from four separate addition cycles (i.e., one for each base) to the following: add A, C, G, T (each differently labeled) with polymerase and an appropriate reaction buffer, rinse, image the four resolvable dyes and record which base (if any) was incorporated, cleave and cap the nucleotides, and repeat. The described nucleotide analogs facilitate this kind of sequencing because of their ability to incorporate one and only one base at a time. Without that ability, if all four bases are added to the incorporation reaction at once multiple bases would be added to a given strand and the interactions between the proximate dyes would hinder the ability to resolve the sequence information correctly.

For example, the nucleotide analogs described herein can facilitate sequencing nucleic acids containing homopolymer sequences, using sequencing by synthesis methodology (e.g., using the methods of US 2007/0190546, herein incorporated by reference in its entirety for all purpose. When the template sequence contains a homopolymer, using a polymerase, nucleotide analog, and reaction buffer combination that allows for only a single nucleotide analog incorporation allows for each base in the homopolymer to be sequenced sequentially. After one base is incorporated into the homopolymer and detected, the portion of the analog that inhibits subsequent base incorporation and that contains the fluorescent label is removed, making incorporation of the next base in the homopolymer possible during the next addition cycle of the correct base.

Reference to the following figures or schemes illustrating an exemplary reaction scheme and nucleotide analogs is intended in no way to limit the scope of this invention but is provided to illustrate how to prepare and use the compounds of the present invention.

EXAMPLES

Example 1

Caproic-Glu and Caproic-Glu

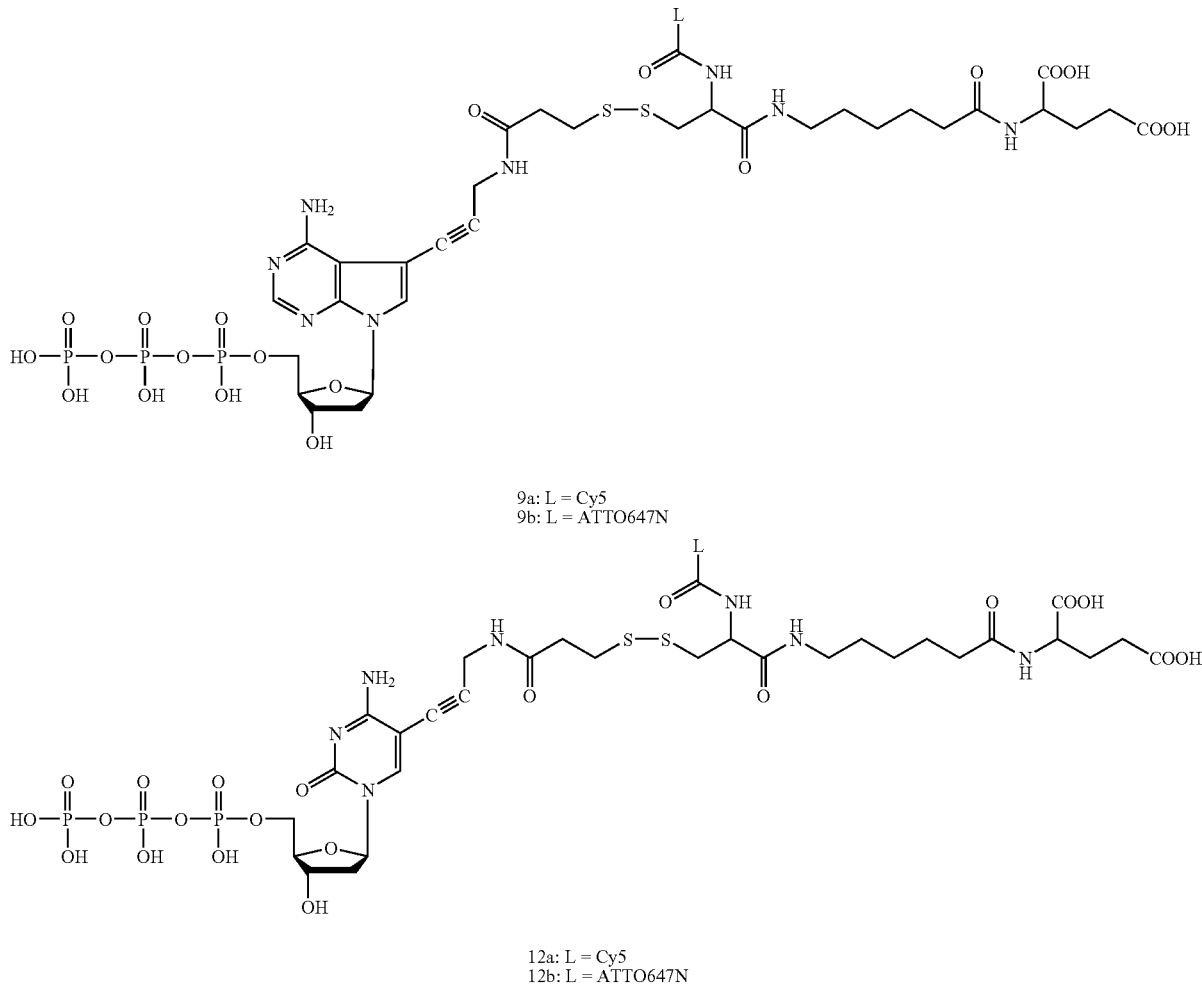

9a: L = Cy5
9b: L = ATTO647N

12a: L = Cy5
12b: L = ATTO647N

-continued
Synthetic Scheme I
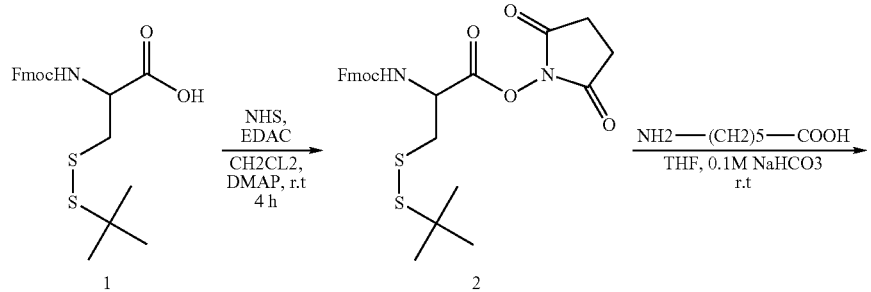
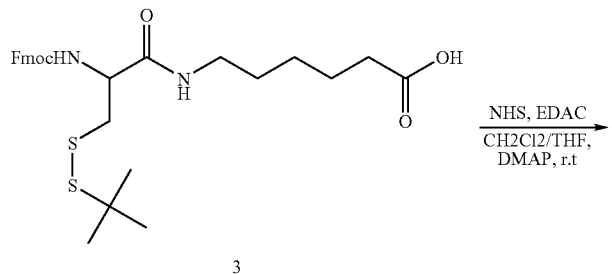
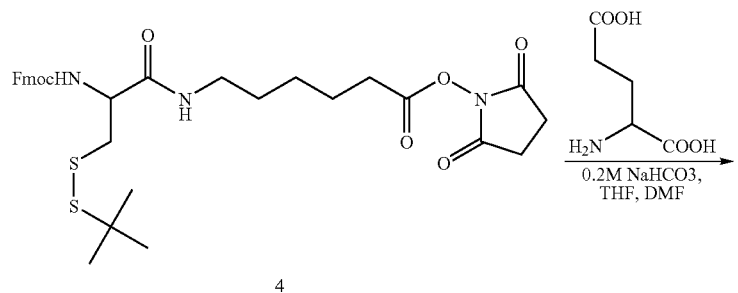
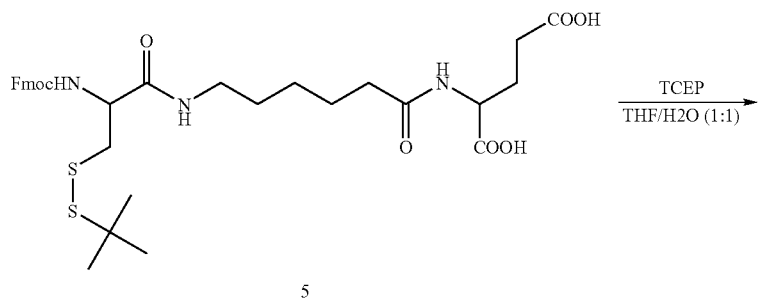
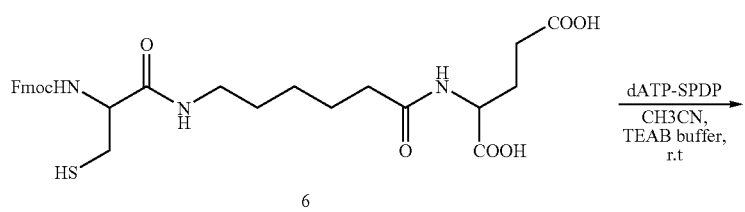

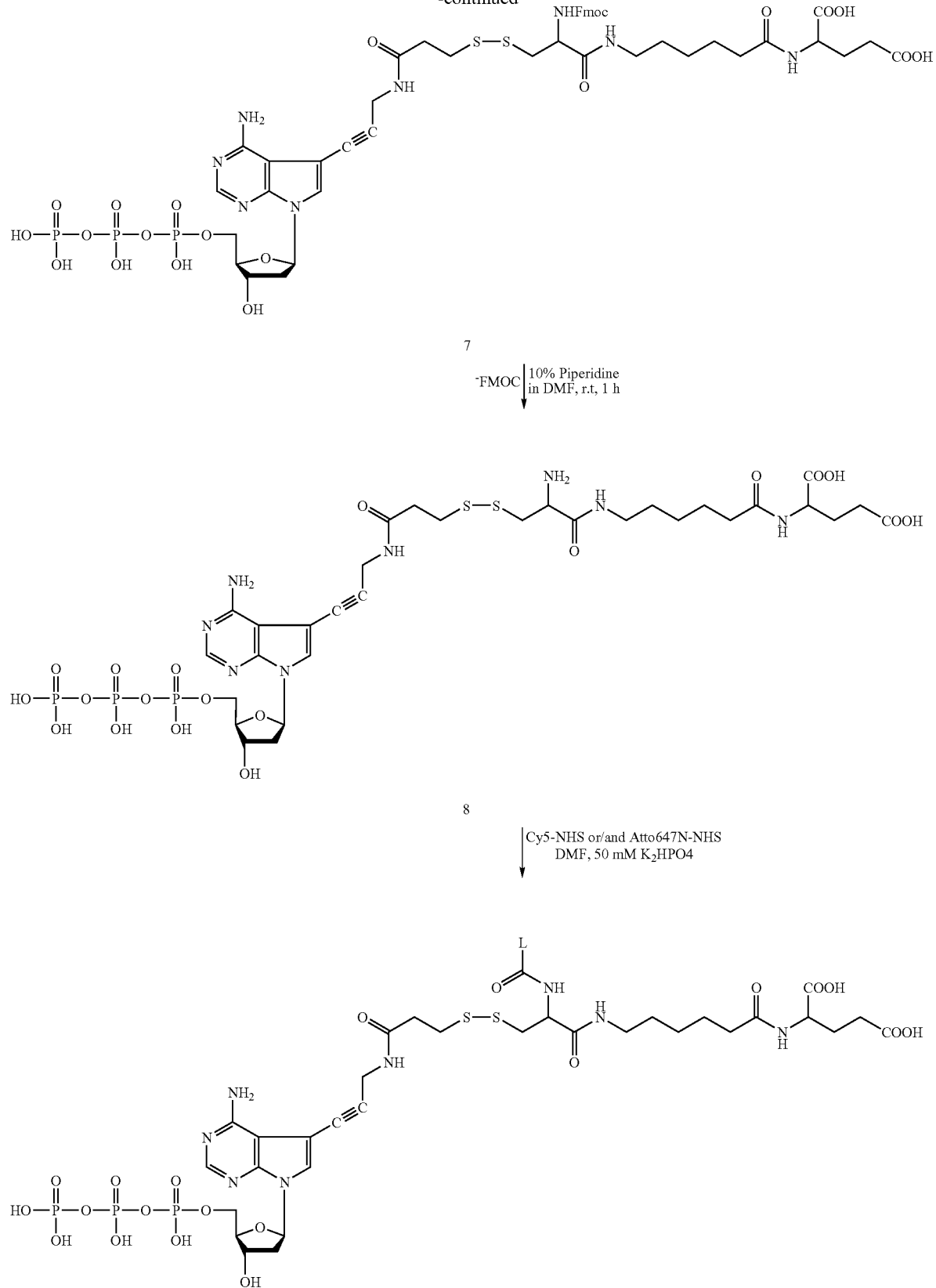
9a: L = Cy5
9b: L = ATTO647N

3-tert-Butyldisulfanyl-2-(9H-fluoren-9-ylmethoxy-carbonylamino)-propionic acid 2,5-dioxo-pyrrolidin-1-yl ester (2)

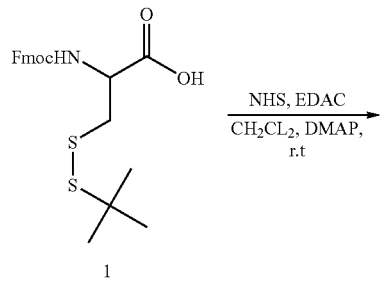

1

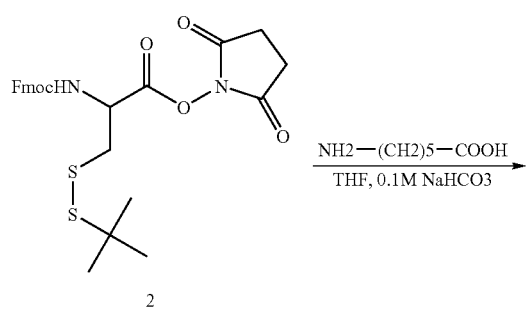

2

To a solution of Fmoc-Cys(SStBu)-OH (1, 2.15 g, 5.0 mmole,) dissolved in anhydrous $CH_2Cl_2$ (30 mL) was added N-Ethyl-N'-(3-dimethylaminopropyl)carbodiimide hydrochloride (EDAC, 1.146 g, 6 mmole), the reaction mixture was stirred for 10 min. at room temperature (RT) and then added N-hydroxysuccinimide (NHS) (0.690 g, 6.0 mmole). To this reaction mixture was added catalytic amount of N,N'-dimethlyaminopyridine and stirred at RT until completion of reaction tested with TLC. The solvent was evaporated and the residue obtained was extracted with ethyl acetate (50 mL×2), washed with 1M $NaHCO_3$ (10 mL), followed by brine solution (20 mL) and dried over anhydrous $Na_2SO_4$. Evaporation of the solvent afforded 2 as a white crystalline solid. Yield. 2.5 g (95%).

6-[3-tert-Butyldisulfanyl-2-(9H-fluoren-9-yl-methoxycarbonylamino)-propionylamino]-hexanoic acid (3)

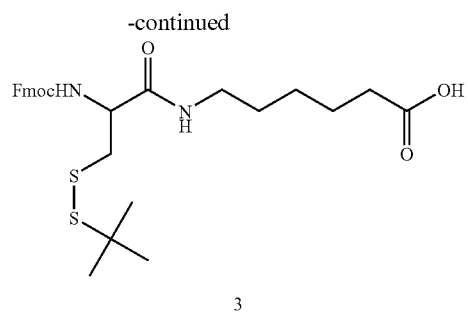

3

To a solution of 6-Aminohexanoic acid (0.158 g, 1.2 mmole) dissolved in 0.1M $NaHCO_3$ (2.0 mL) was added the NHS ester 2 (0.68 g, 1.3 mmole) in 4 mL of anhydrous THF. The reaction mixture was stirred at RT for 2 hr. The solvent was completely evaporated and the dried solid residue obtained was dissolved in $CH_3OH/CH_2Cl_2$ mixture and purified by silica gel column chromatography using 10% $CH_3OH/CH_2Cl_2$ and obtained 3 as a white solid on evaporation the solvent. Yield: 0.5 g (77%).

6-[3-tert-Butyldisulfanyl-2-(9H-fluoren-9-yl-methoxycarbonylamino)-propionylamino]-hexanoic acid 2,5-dioxo-pyrrolidin-1-yl ester (4)

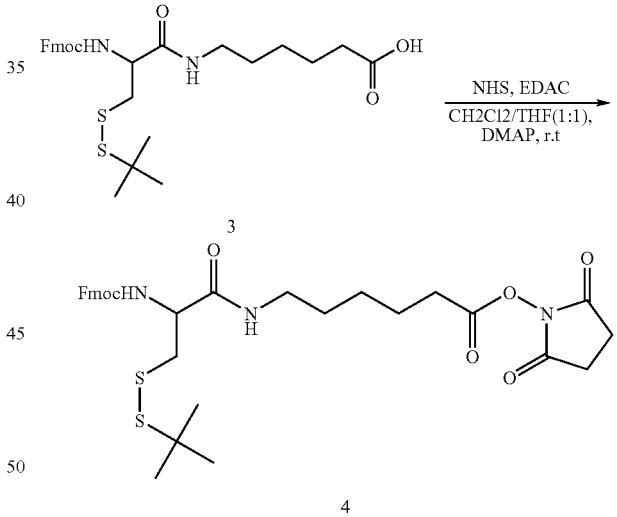

To a solution of (3, 500 mg, 0.92 mmole,) dissolved in anhydrous $CH_2Cl_2$/THF (1:1)(5 mL) was added N-Ethyl-N'-(3-dimethylaminopropyl)carbodiimide hydrochloride (EDAC, 191 mg, 1.0 mmole), followed by NHS (115 mg, 1.0 mmole). To this reaction mixture was added catalytic amount of N,N'-dimethlyaminopyridine and stirred at RT until completion of reaction tested with TLC. The solvent was evaporated and the residue obtained was extracted with ethyl acetate (50 mL×2), washed with 1M $NaHCO_3$ (10 mL), followed by brine solution (10 mL) and dried over anhydrous $Na_2SO_4$. Evaporation of the solvent afforded 4 as a white crystalline solid. Yield: 0.52 g (88%).

2-{(6-[3-tert-Butyldisulfanyl-2-(9H-fluoren-9-yl-methoxycarbonylamino)-propionylamino]-hexanoy-lamino}-nentanedioic acid (5)

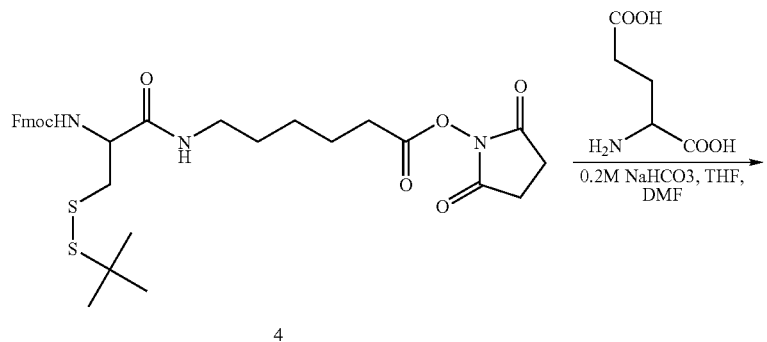

4

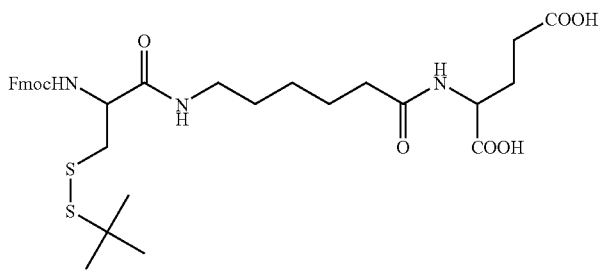

5

To a stirred solution of Glutamic acid (20 mg, 0.14 mmole) in 0.2M NaHCO$_3$ (0.5 mL) was added 6-[3-tert-Butyldisulfanyl-2-(9H-fluoren-9-ylmethoxycarbonylamino)-propionylamino]-hexanoic acid 2,5-dioxo-pyrrolidin-1-yl ester (4, 96 mg, 0.15 mmole) dissolved in (THF-DMF(1:1), 0.5 mL). The reaction mixture was stirred at RT for 10 min. and analyzed with LCMS which showed the product (5) peak with mass m/z: 671.95 [M-H]. The reaction was stirred at RT for overnight and purified by HPLC using Phenomenex C18 preparative column, (250×21.00 mm, gradient: 2% CH$_3$CN/50 mM TEAB (triethylammonium bicarbonate), pH 8.4, 10 mL/min flow). Fractions containing the compound 5 were collected together and evaporated the solvent using rotary evaporator and dried. Yielded 5 as a white solid: 50 mg.

2-{6-[2-(9H-Fluoren-9-ylmethoxycarbonylamino)-3-mercapto-propionylamino]-hexanoylamino}-pentanedioic acid (6)

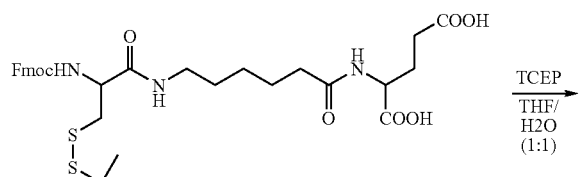

5

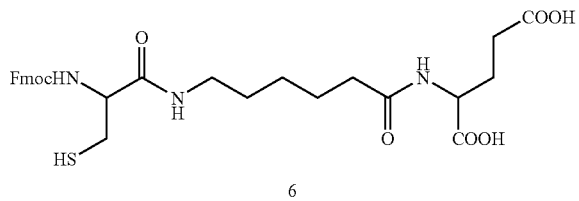

6

A solution of (5) (10 mg, 0.015 mmole) in H$_2$O-THF (1:1, 1.0 ml) was treated with tris(2-carboxyethyl)phosphine (TCEP, 0.10 mL, 0.5M in H$_2$O). The reaction was stirred at RT for 4 h until complete cleavage of disulphide bond (monitored by LCMS) and purified by HPLC using Phenomenex C18 preparative column, (250×21.00 mm, gradient: 2% CH$_3$CN/50 mM TEAB, pH 8.4, 10 mL/min flow). Fractions containing the compound 6 were pooled and used immediately for the subsequent displacement reaction with dATP-SPDP (SPDP: N-succinimidyl 3-(2-pyridyl dithio)propionate) and dCTP-SPDP as described below. LCMS: m/s: 583.95[M-H].

Compound 7

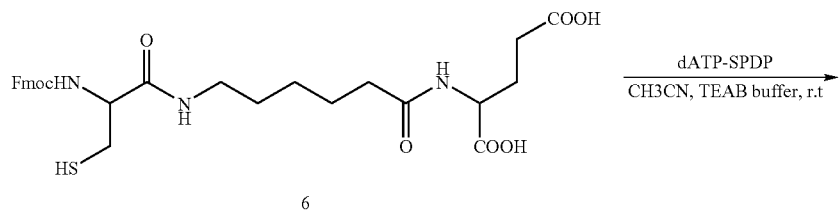

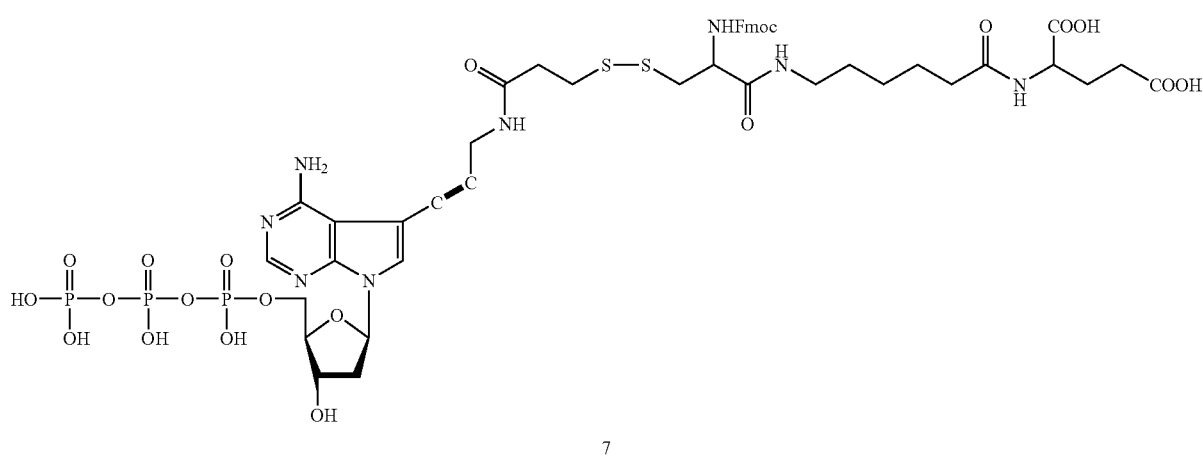

The fractions containing compound 6 in 60% CH₃CN/50 mM TEAB buffer (4.0 mg, in 4 mL) collected from HPLC were mixed with dATP-SPDP (3.6 μmole, ref. previous patent) in 4 ml of 30% CH₃N/50 mM TEAB buffer, pH 8.4 in a round bottom flask and stirred for 2 h. The reaction solution was concentrated under reduced pressure, diluted with water and purified with HPLC (Phenomenex C18 column, 250× 21.0 mm, gradient: 1.5% CH₃CN/50 mM TEAB buffer, 10 mL/min flow rate). Fractions containing the desired were pooled together and evaporated and dried. Yielded 7 (3.0 mg) as a white solid. LCMS: m/z: 2121.80 [M-2H], 606.05 [M/2-2H].

Compound 8

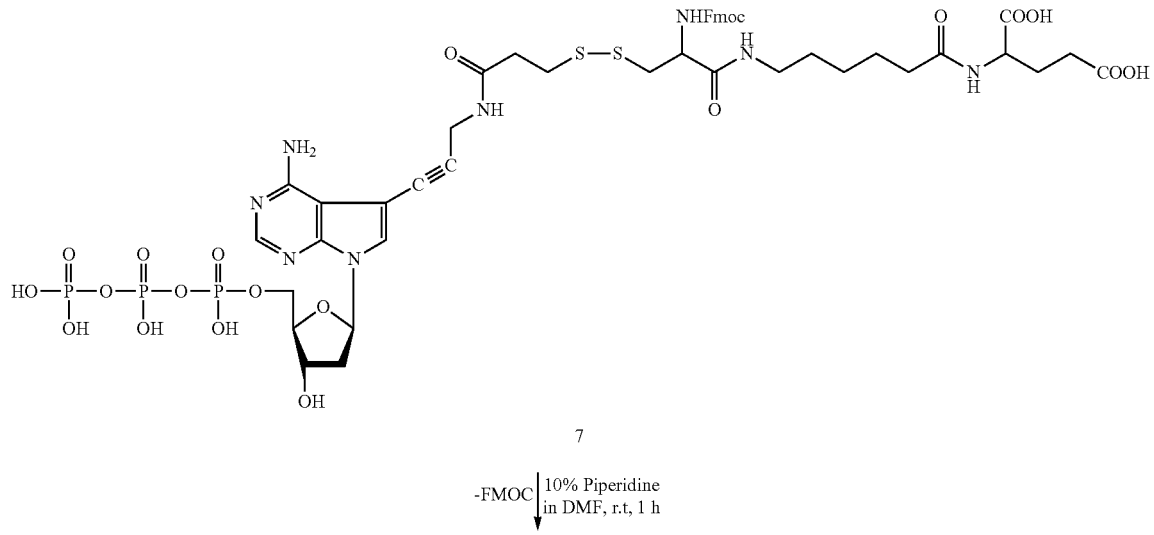

-continued

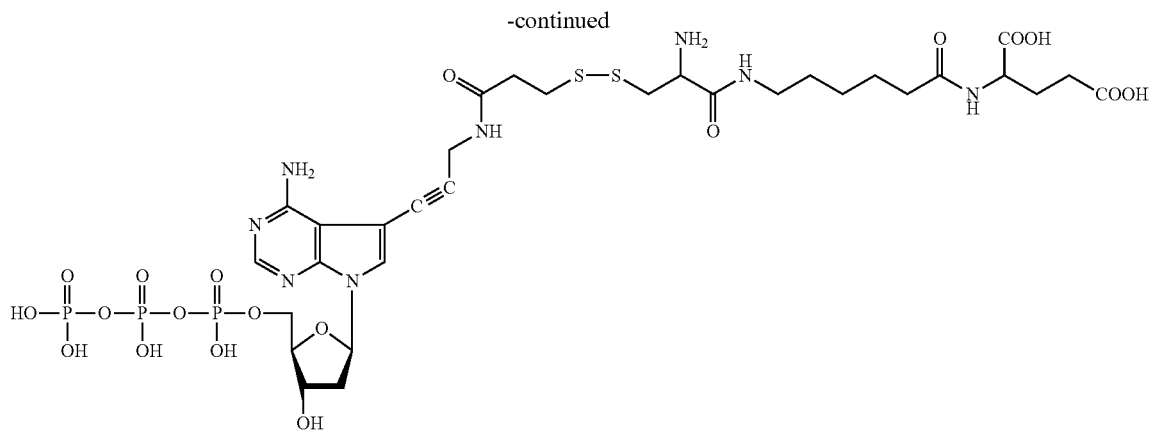

8

The compound 7 (2.0 mg) obtained was dissolved in anhydrous DMF (0.6 mL) added 60 µl of piperidine. The reaction mixture was then stirred at RT for an hour. The complete cleavage of FMOC group was monitored by LCMS and the reaction mixture was purified by HPLC (Phenomenex C18 column, 250×21.0 mm, gradient: 1.5% $CH_3CN$/50 mM TEAB buffer, 10 mL/min flow rate). Fractions containing the desired were pooled together and evaporated and obtained 8 (1.0 µmole) as a colorless solid. LCMS: 990.95 [M/2-2H].

Compound 9

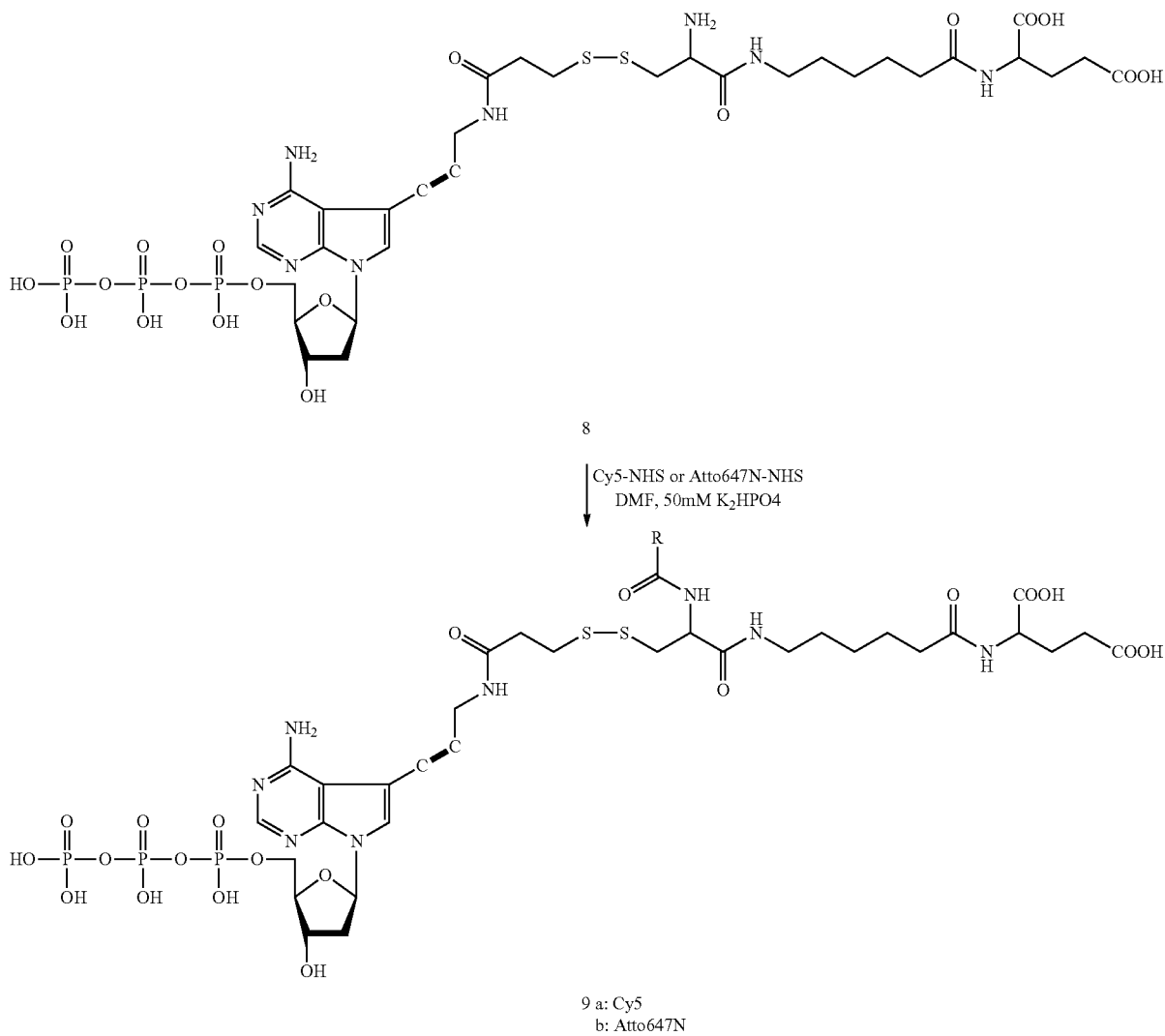

9 a: Cy5
b: Atto647N

To a solution of 8 (0.5 μmole) in 0.5 mL of 50 mM K$_2$HPO$_4$ was added Cy5-NHS (1 mg, 1.2 μmole) dissolved in 20 μL of anhydrous DMF and stirred at RT until the complete disappearance of starting material 8 which was monitored by LCMS. Then the blue color reaction mixture was purified HPLC (Phenomenex C18 column, 250×21.0 mm, gradient: 1.5% CH$_3$CN/50 mM TEAB buffer, 10 mL/min flow rate). Fractions containing the desired were pooled together and lyophilized. Yielded 9a (0.36 μmole) as a blue solid. LCMS: 814.40 [M/2-2H].

Similarly a solution of 8 (0.5 μmole) in 0.5 mL of 50 mM K$_2$HPO$_4$ was added Atto 647N-NHS (2 mg, 2.5 μmole) dissolved in 40 μL of anhydrous DMF and stirred at RT until the complete disappearance of starting material 8 which was monitored by LCMS. Then the blue color reaction mixture was purified HPLC (Phenomenex C18 column, 250×21.0 mm, gradient: 2.0% CH$_3$CN/50 mM TEAB buffer, 10 mL/min flow rate). Fractions containing the desired were pooled together and lyophilized. Yielded 9b (0.3 μmole) as a blue solid. LCMS: 1595.2 [M-2H], 797.0 [M/2-2H].

Compound 10

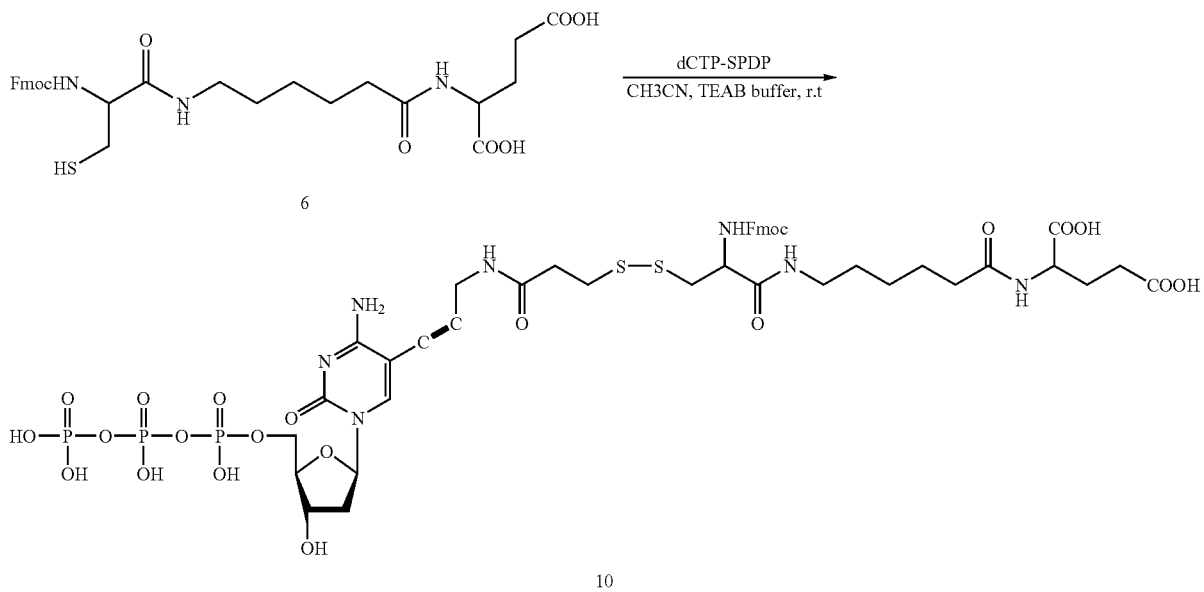

The fractions containing compound 6 in 60% CH$_3$CN/50 mM TEAB buffer (3.0 mg, in 3 mL) collected from HPLC were mixed with dCTP-SPDP (3.0 μmole, ref. previous patent) in 3 ml of 30% CH$_3$N/50 mM TEAB buffer, pH 8.4 in a round bottom flask and stirred for 2 hr. The reaction solution was concentrated under reduced pressure, diluted with water and purified with HPLC (Phenomenex C18 column, 250× 21.0 mm, gradient: 1.5% CH$_3$CN/50 mM TEAB buffer, 10 mL/min flow rate). Fractions containing the desired were pooled together and evaporated and dried. Yielded 10 (3.0 mg) as a white solid. LCMS: m/z: 1189.85 [M-2H], 594.8 [M/2-2H].

Compound 11

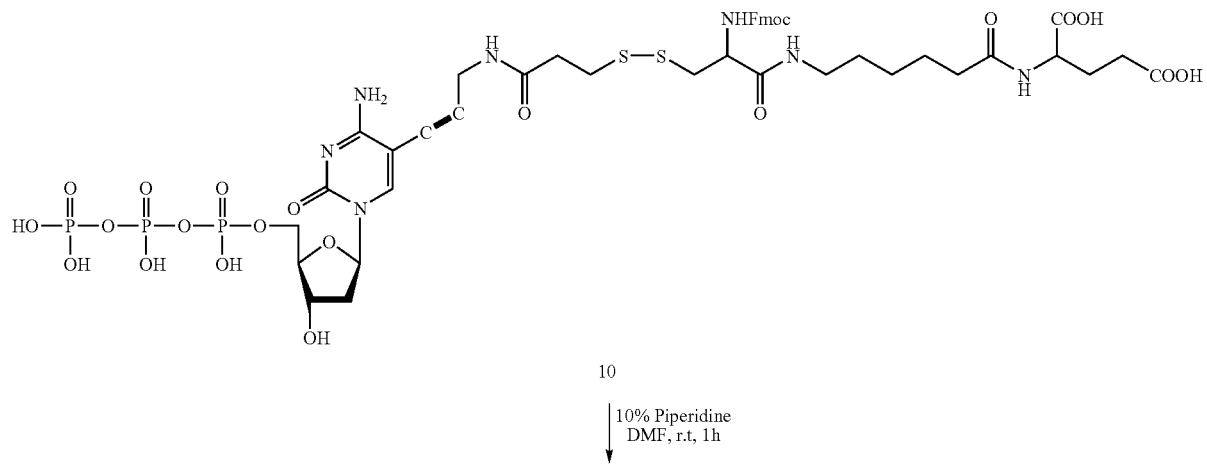

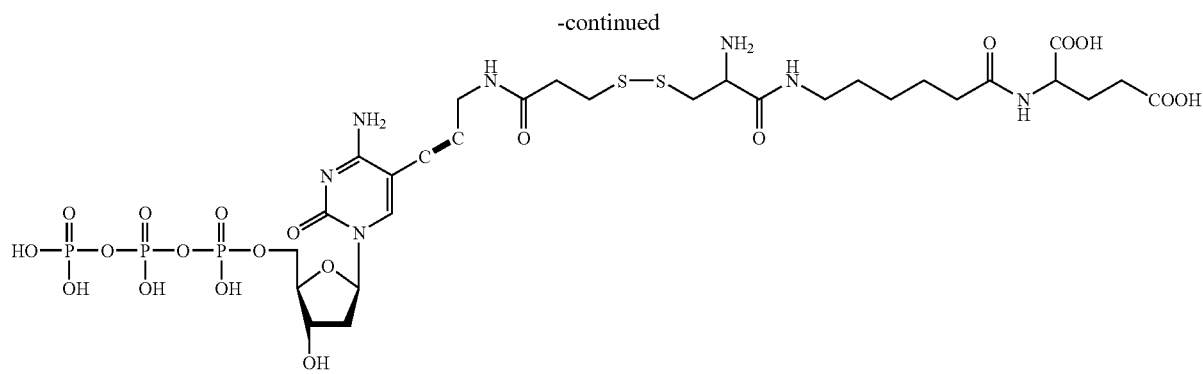

11

The compound 10 (2.0 mg) obtained was dissolved in anhydrous DMF (0.6 mL) added 60 µl of piperidine. The reaction mixture was then stirred at RT for an hour. The complete cleavage of FMOC group was monitored by LCMS and the reaction mixture was purified by HPLC (Phenomenex C18 column, 250×21.0 mm, gradient: 1.5% CH$_3$CN/50 mM TEAB buffer, 10 mL/min flow rate). Fractions containing the desired were pooled together and evaporated and obtained 11 (1.2 µmole) as a colorless solid. LCMS: 967.90 [M/2-2H].

Compound 12

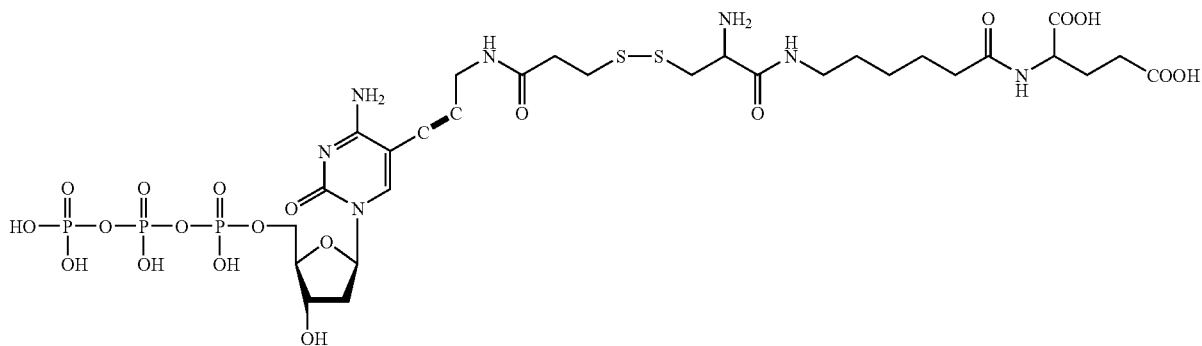

11

| Cy5-NHS or Atto647N-NHS,
DMF, 50mM K$_2$HPO4

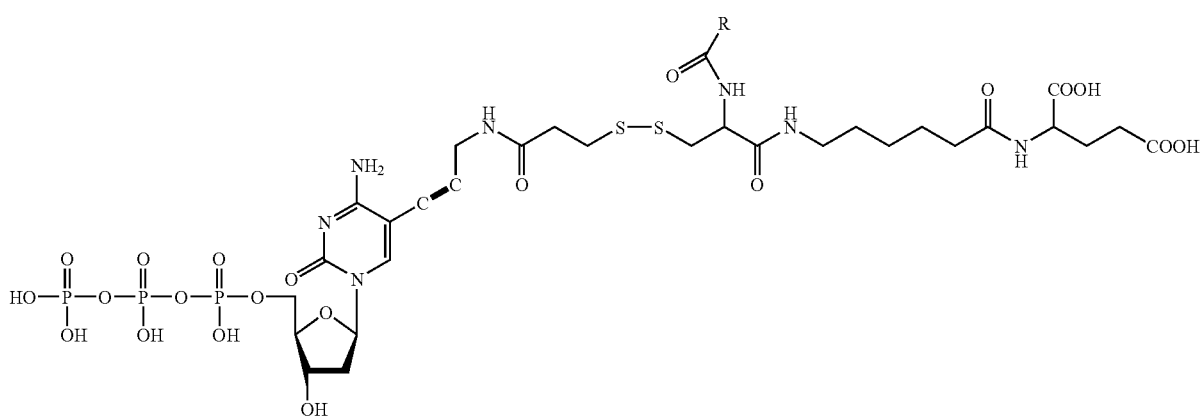

12 a: Cy5
b: Atto647N

To a solution of 11 (0.6 μmole) in 0.5 mL of 50 mM K$_2$HPO$_4$ was added Cy5-NHS (1.5 mg, 1.6 μmole) dissolved in 30 μL of anhydrous DMF and stirred at RT until the complete disappearance of starting material 11 which was monitored by LCMS. Then the blue color reaction mixture was purified HPLC (Phenomenex C18 column, 250×21.0 mm, gradient: 1.5% CH$_3$CN/50 mM TEAB buffer, 10 mL/min flow rate). Fractions containing the desired were pooled together and lyophilized. Yielded 12a (0.5 μmole) as a blue solid. LCMS: 814.40 [M/2-2H].

Similarly a solution of 11 (0.4 μmole) in 0.5 mL of 50 mM K$_2$HPO$_4$ was added Atto 647N-NHS (2 mg, 2.5 μmole) dissolved in 40 μL of anhydrous DMF and stirred at RT until the complete disappearance of starting material 11 which was monitored by LCMS. Then the blue color reaction mixture was purified HPLC (Phenomenex C18 column, 250×21.0 mm, gradient: 2.0% CH$_3$CN/50 mM TEAB buffer, 10 mL/min flow rate). Fractions containing the desired were pooled together and lyophilized. Yielded 12b (0.35 μmole) as a blue solid. LCMS: 1595.2 [M-2H], 797.0 [M/2-2H].

Example 2

Caproic-Asp-Asp

Synthetic Scheme II

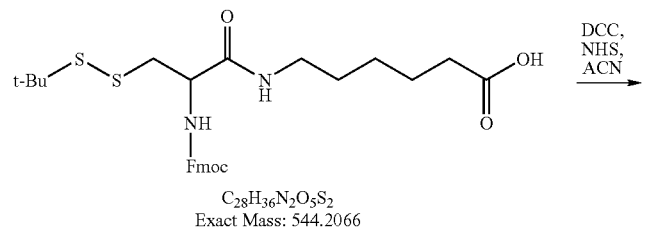

C$_{28}$H$_{36}$N$_2$O$_5$S$_2$
Exact Mass: 544.2066

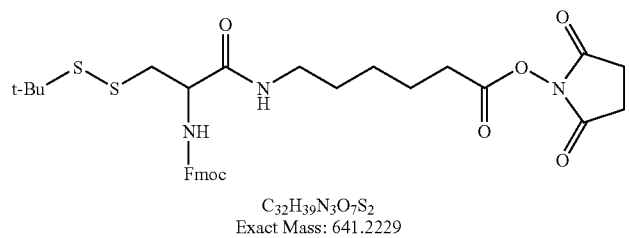

C$_{32}$H$_{39}$N$_3$O$_7$S$_2$
Exact Mass: 641.2229

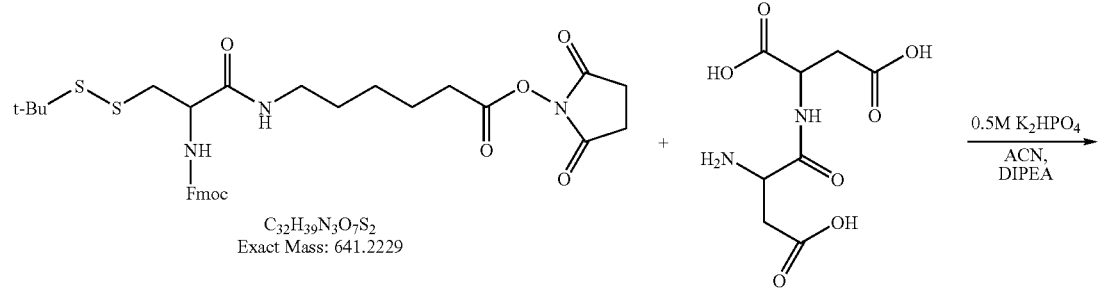

C$_{32}$H$_{39}$N$_3$O$_7$S$_2$
Exact Mass: 641.2229

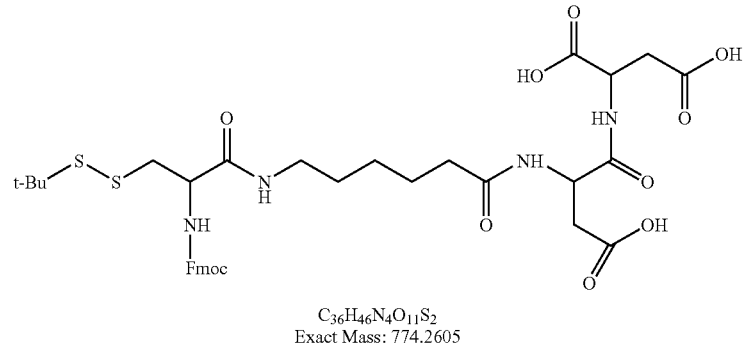

C$_{36}$H$_{46}$N$_4$O$_{11}$S$_2$
Exact Mass: 774.2605

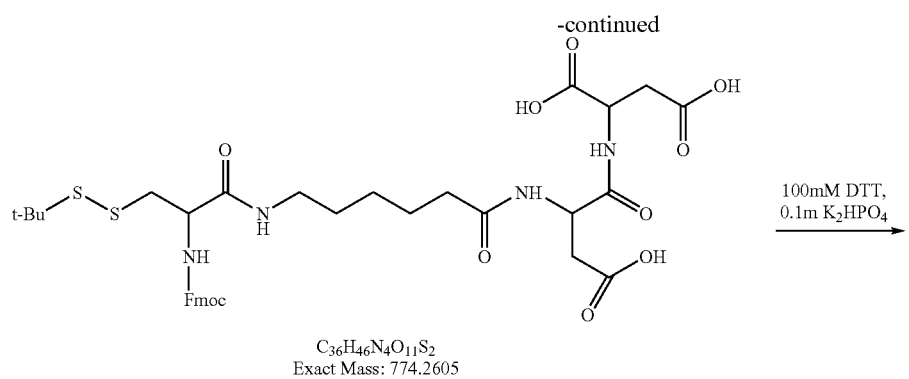
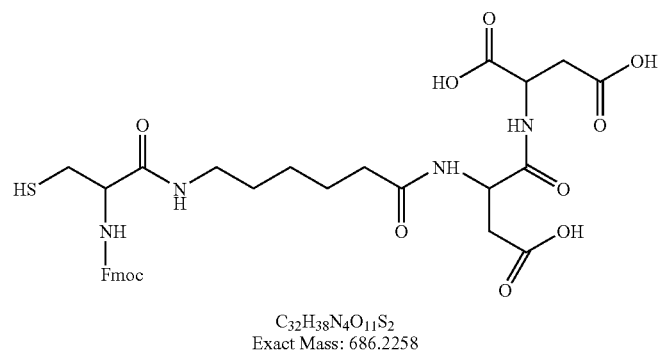
C* cap-Asp-Asp:
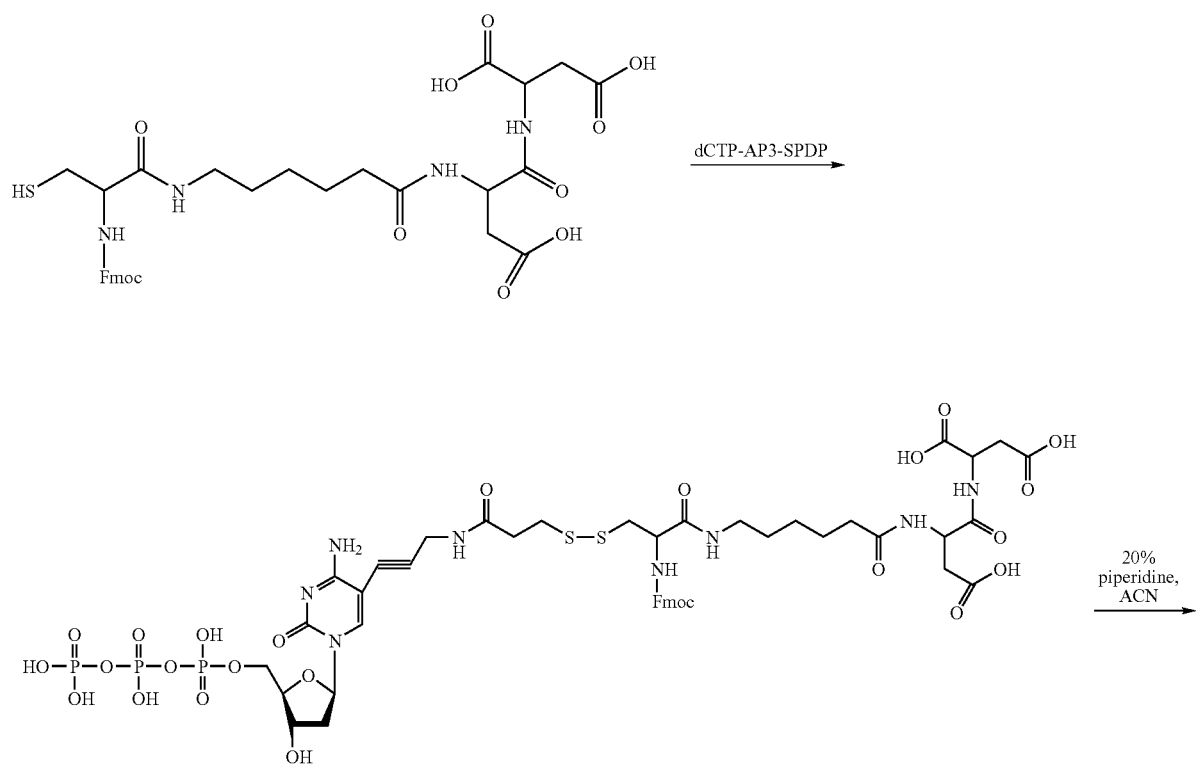

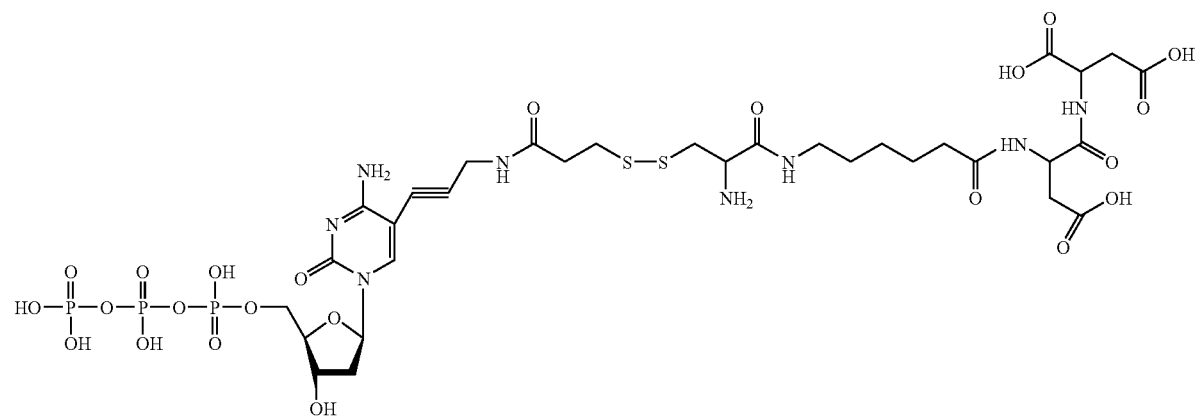
21
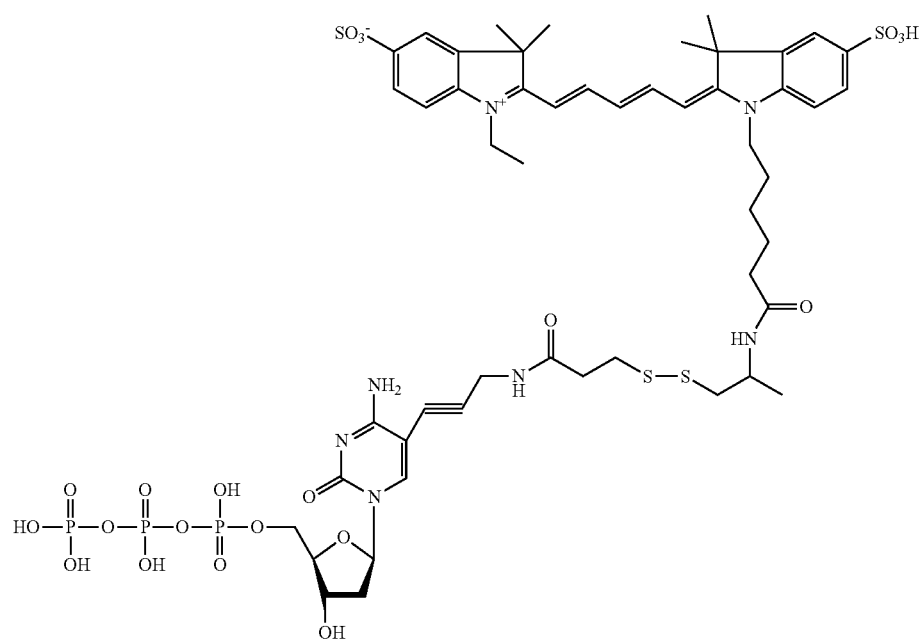
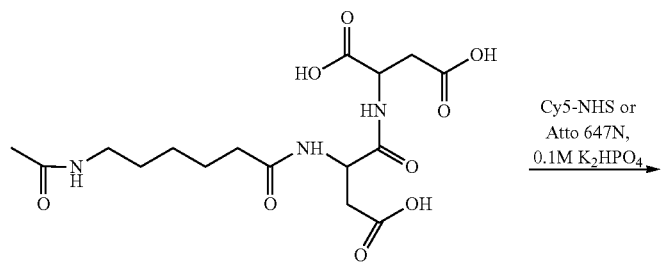
23
C$_{65}$H$_{87}$N$_{10}$O$_{30}$P$_3$S$_4$
Exact Mass: 1708.3685

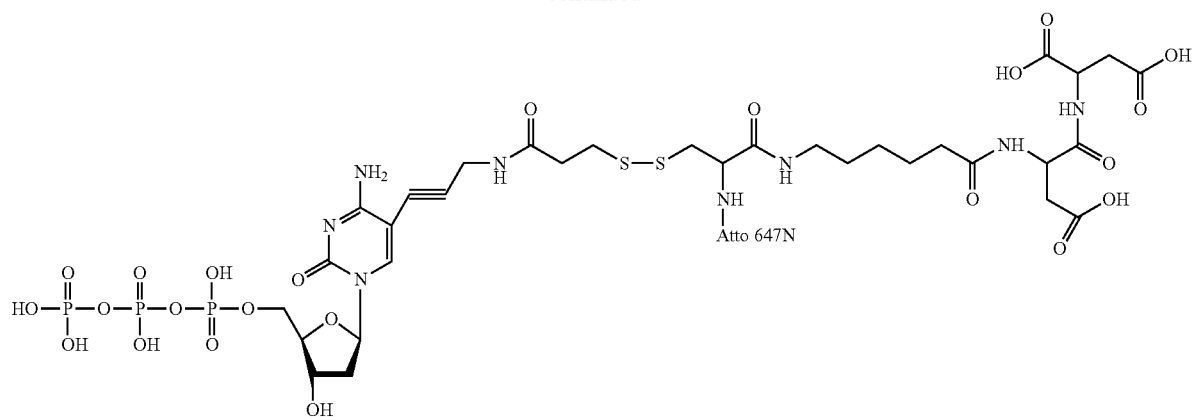
25
A*cap-Asp-Asp:
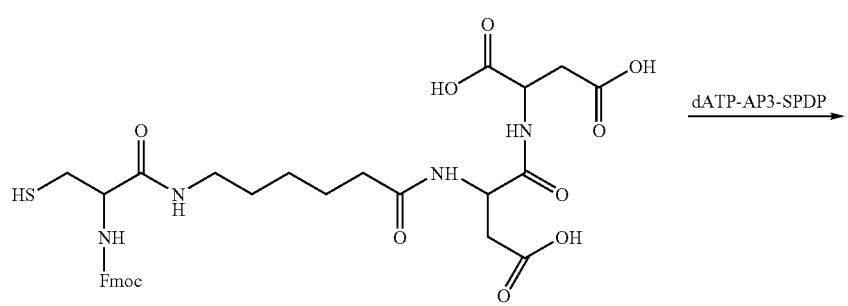
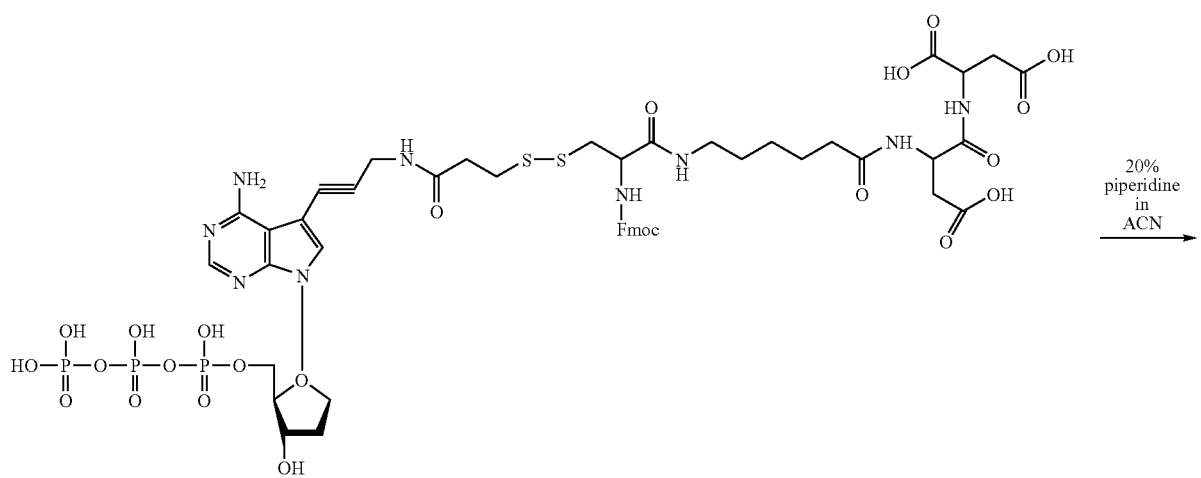
20

-continued
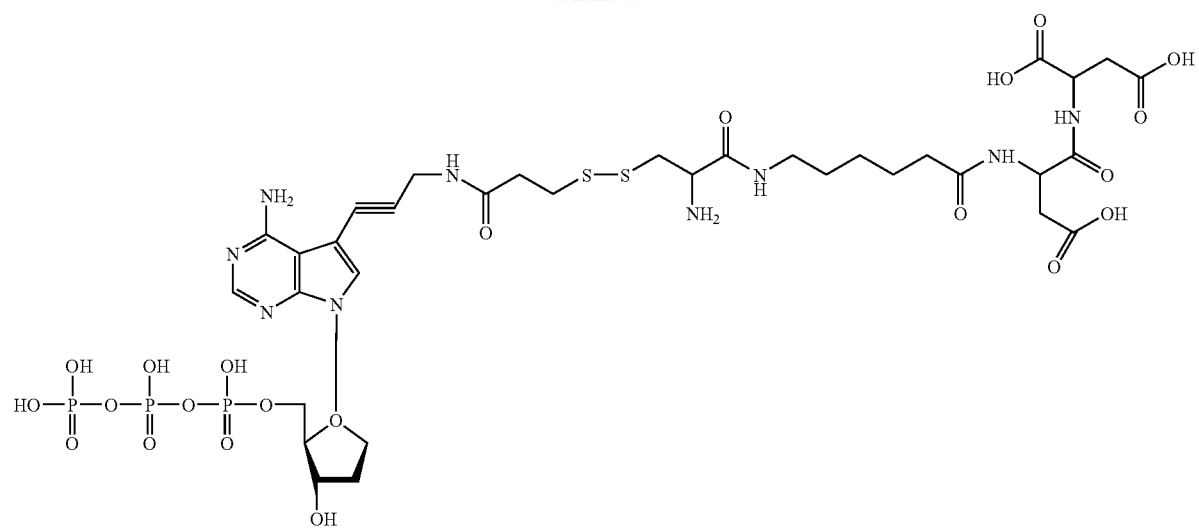
22
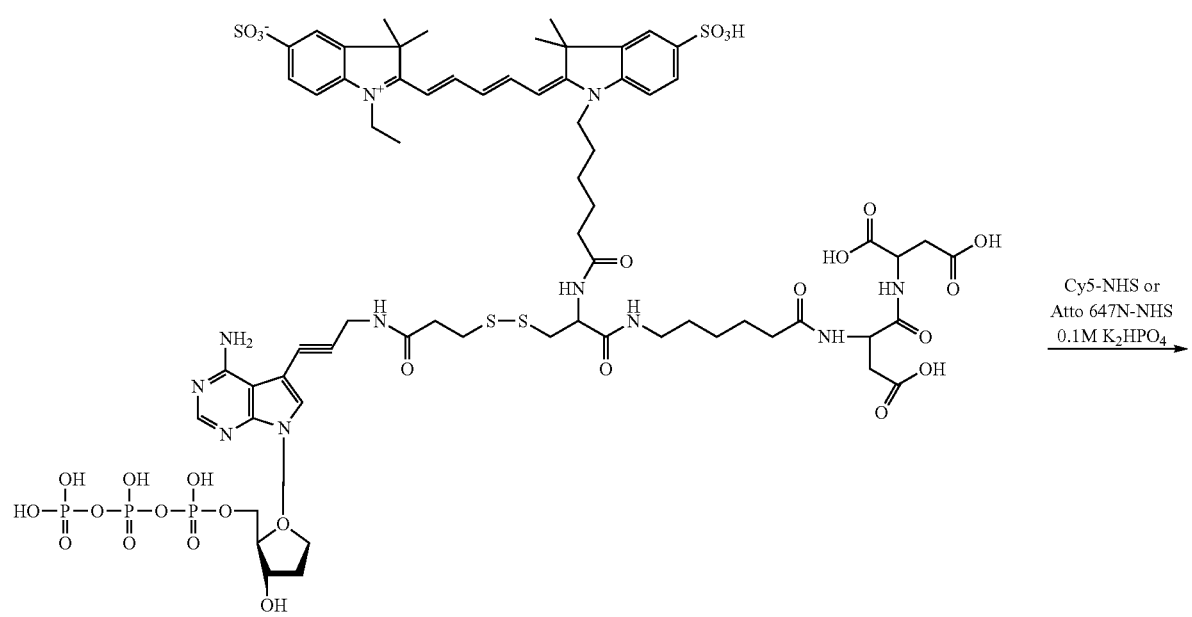
24

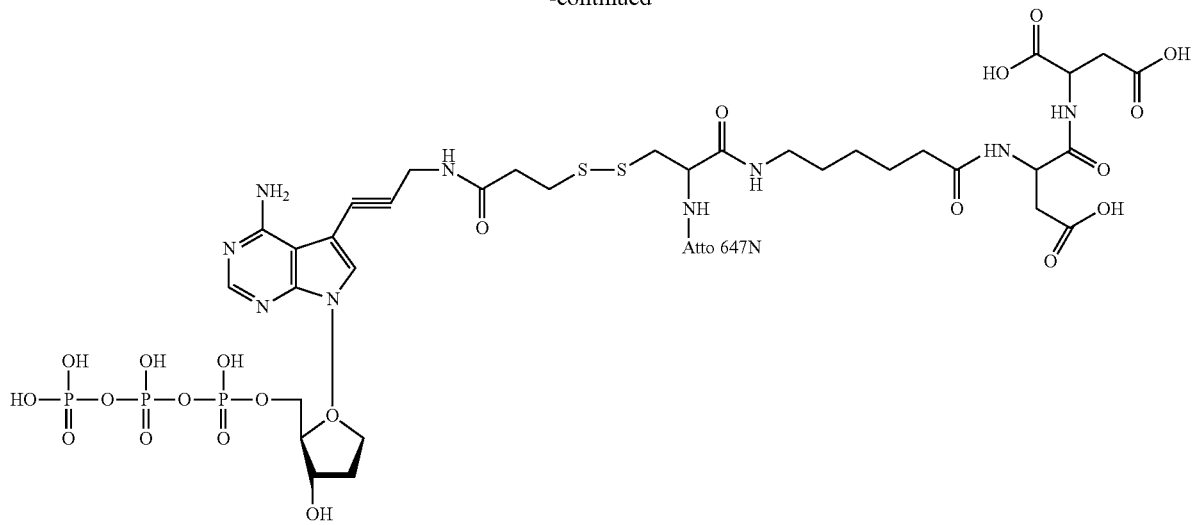

26

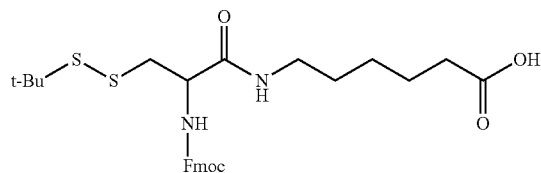

3

α-N-Fmoc-S-tert-butylthio-L-cysteine (1 g, 2.32 mmol) was dissolved in anhydrous acetonitrile and solution of dicyclohexylcarbodiimide (DCC) (573 mg, 2.78 mmol in CH$_3$CN) was added followed by solution of NHS (345 mg, 3.01 mmol in CH$_3$CN). After 1 hr. dicyclohexylurea was spun down and active ester used without purification in coupling with ε-amino-hexanoic acid (304 mg, 2.32 mmol) dissolved in 50% aq. DMF. N,N'-Diisopropylethylamine (DIPEA) was added to correct pH to 8.0. Upon completion reaction mixture was acidified to pH 3 and partitioned between water and dichloromethane (DCM). Organic layer was dried over anhydrous Na$_2$SO$_4$ and evaporated to give 1.33 g of crude material. Purification using flash chromatography in DCM/methanol gave 745 mg of pure material (MW=544.75).

DCC (35 mg, 169 μmols, CH$_3$CN) and NHS (21 mg, 183 μmols, ACN). After 1 hr. precipitate of dicyclohexylurea was removed by centrifugation and ester used without further purification in coupling with H-Asp-Asp-OH peptide (12 mg, 48 nmols) dissolved in 0.5M K$_2$HPO$_4$, pH of reaction mixture corrected to 7.5 with DIPEA. Progress of reaction was monitored by TLC (disappearance of ester) and by LC-MS (formation of product). Upon completion product was isolated by direct injection on preparative HPLC (C18 column, 3% CH$_3$CN gradient in 50 mM TEAB, pH 8.6). Isolated product was lyophilized to give white powder (MW=774.9)

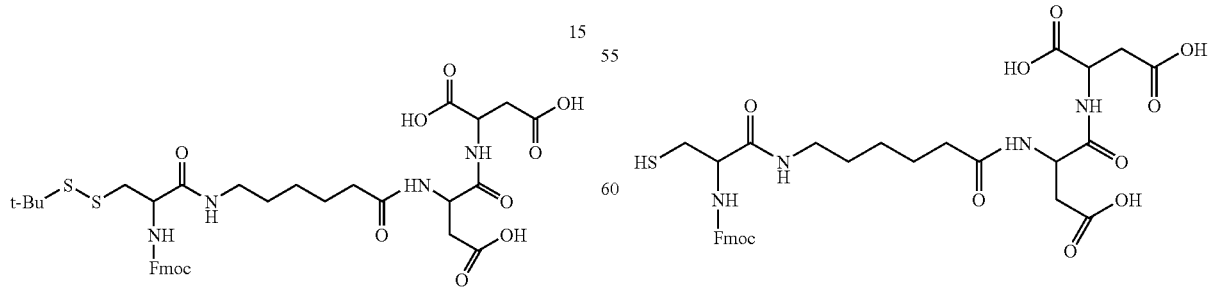

α-N-Fmoc-S-tert-butylthio-L-cyst-caproic acid (3, 77 mg, 141 μmols, CH$_3$CN) was converted to NHS active ester using To free the thiol α-N-Fmoc-5-tert-butylthio-L-cyst-caproic-Asp-Asp-OH (15) was treated with 100 mM DTT in 0.1M K$_2$HPO$_4$ during 1 hr. at RT. Reaction was monitored by LC-MS and upon completion injected directly on preparative HPLC (C18 column). Purification using 2% CH₃CN gradient in 50 mM TEAB, pH 8.6 yielded product (MW=686.7) which was used immediately without evaporation in displacement reaction with SPDP modified nucleotide triphosphates.

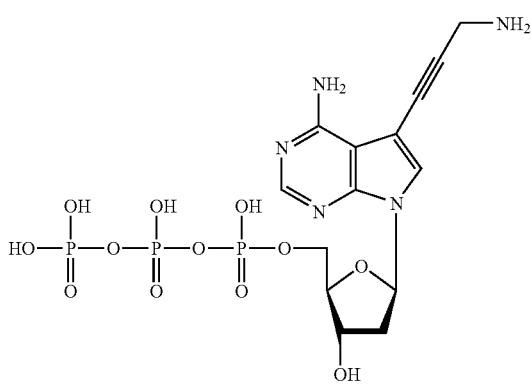

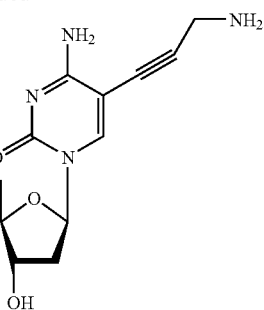

dATP-AP3 and dCTP-AP3 were prepared by a modified procedure of Hobbs and Cocuzza: a) Pyrophosphate and tributylamine were added to the reaction mixture rather than vice versa; b) After pyrophosphate addition the reaction was quenched with 50 mM TEAB within 15 min.; c) DEAE-Sephadex chromatography was replaced by preparative HPLC.

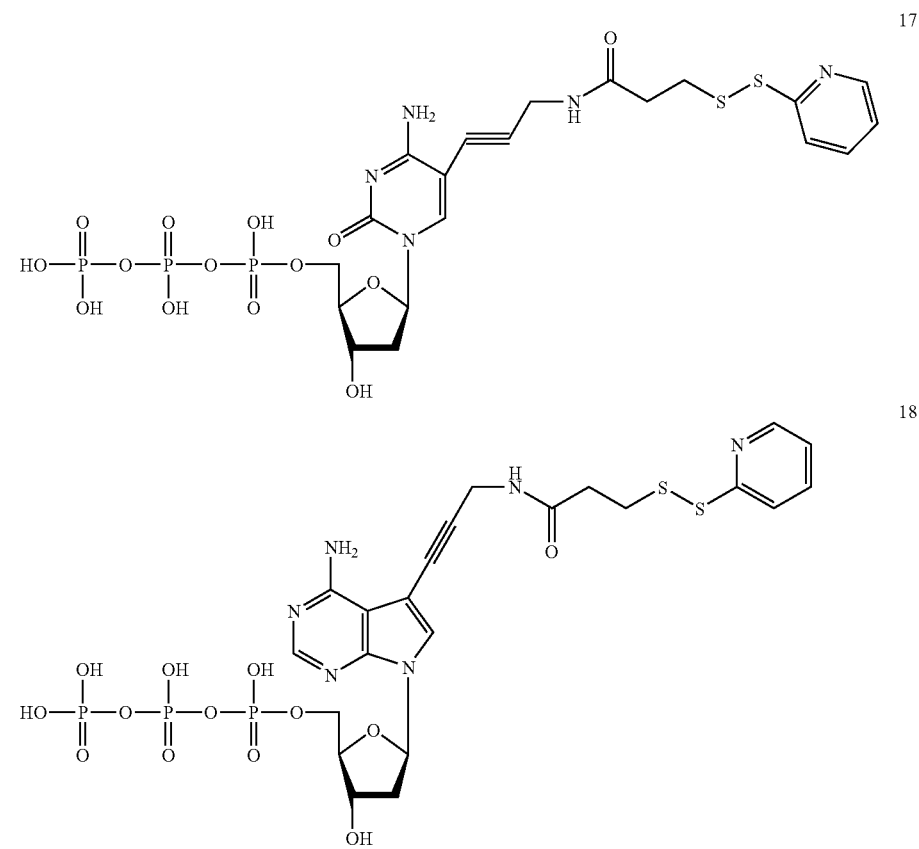

SPDP modification of dATP-AP3 and dCTP-AP3 was accomplished using standard protocol: 2 μmols of dNTP-AP3 were dissolved in 250 μl of 0.1N NaHCO₃ and 1.2 equivalent (.) of freshly prepared 50 mM stock of SPDP in anhydrous DMF was added. Progress of modification was monitored using LC-MS. Product was isolated using preparative HPLC (C18 column) with 1% CH₃CN gradient in 50 mM TEAB, pH 8.6 gradient and used in displacement reaction with thiol without evaporation of HPLC solvents (MW=717.01 for dCTP-AP3-SPDP, MW=740.03 for dATP-AP3-SPDP).

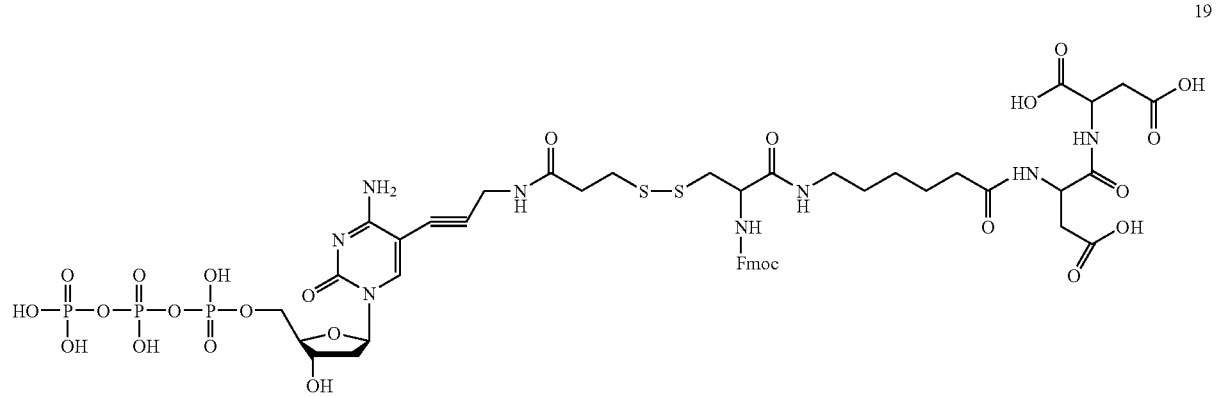

19

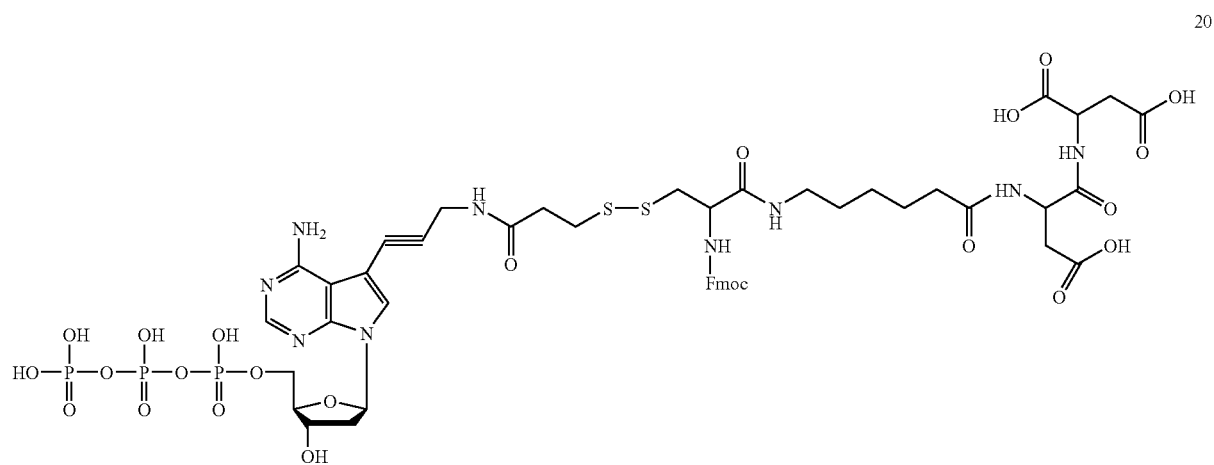

20

Small aliquots of isolated thiol were added to freshly isolated dNTP-AP3-SPDP to obtain displacement product. Progress of reaction was monitored by LC-MS after every addition of thiol. Reaction was completed when all dNTP-AP3-SPDP was consumed at which point reaction mixture was concentrated and purified on preparative HPLC (C18 column) using 1% gradient of CH$_3$CN in 50 mM TEAB, pH 8.6. Isolated product was lyophilized to give white powder (MW=1293.06 for cytidine-analog and MW=1316.09 for adenosine-analog).

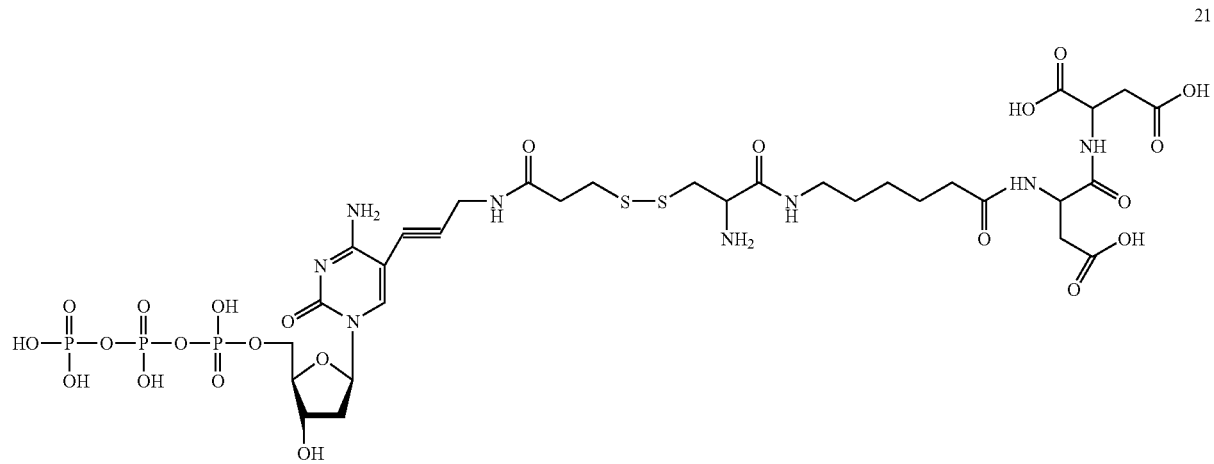

21

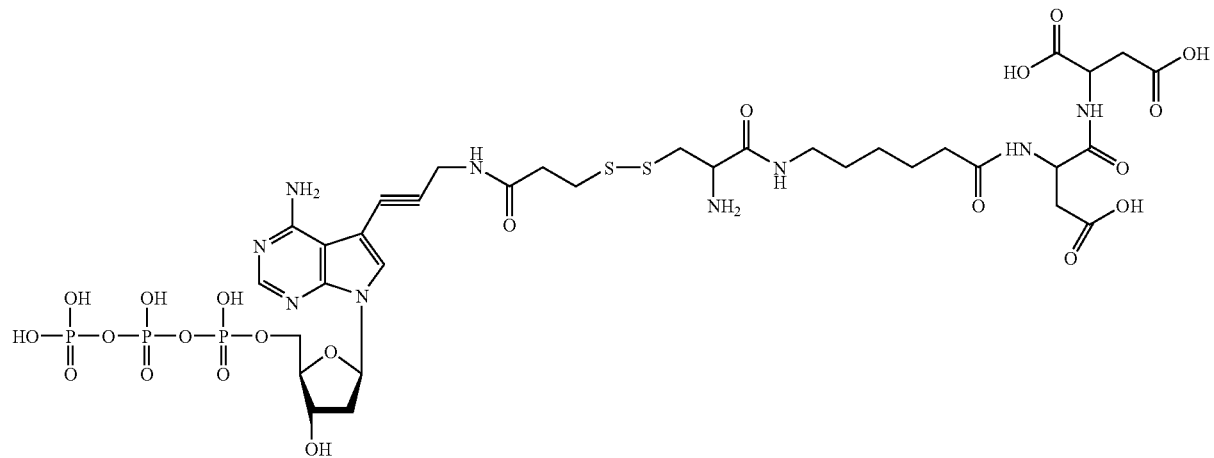
22
Removal of Fmoc-protecting group was accomplished using 20% piperidine in CH$_3$CN (20 min., RT). Subsequently solvents were removed and crude reaction mixture purified on preparative HPLC (C18 column) using 2% CH$_3$CN gradient. Product was dried down and OD measured in water at 290 nm for cytidine analog (800 nmols, MW=1070.8) and 280 nm for adenosine analog (640 nmols, MW=1093.8).
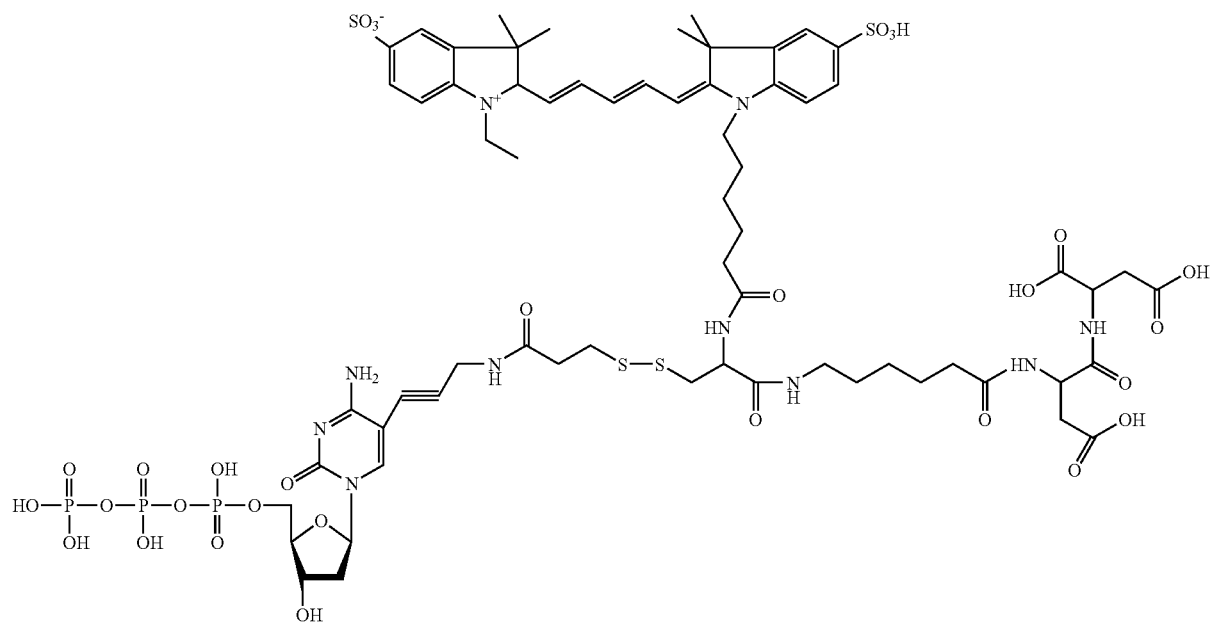
23

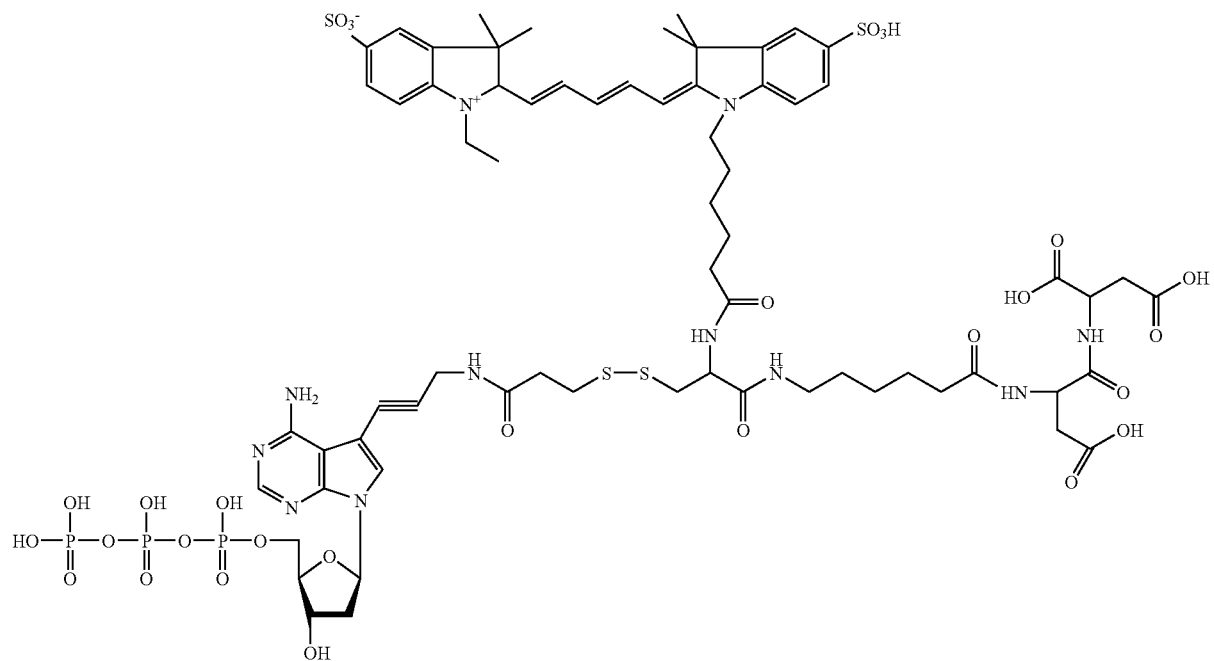
24
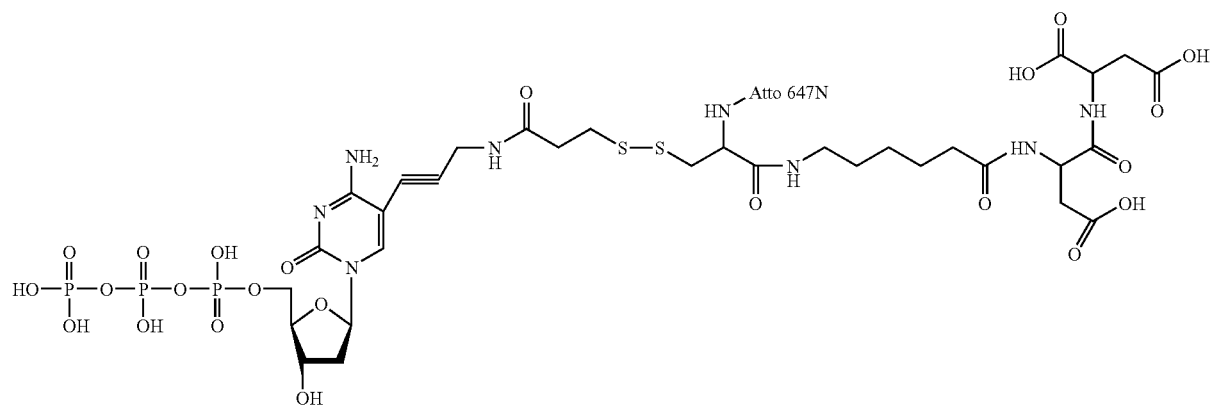
25
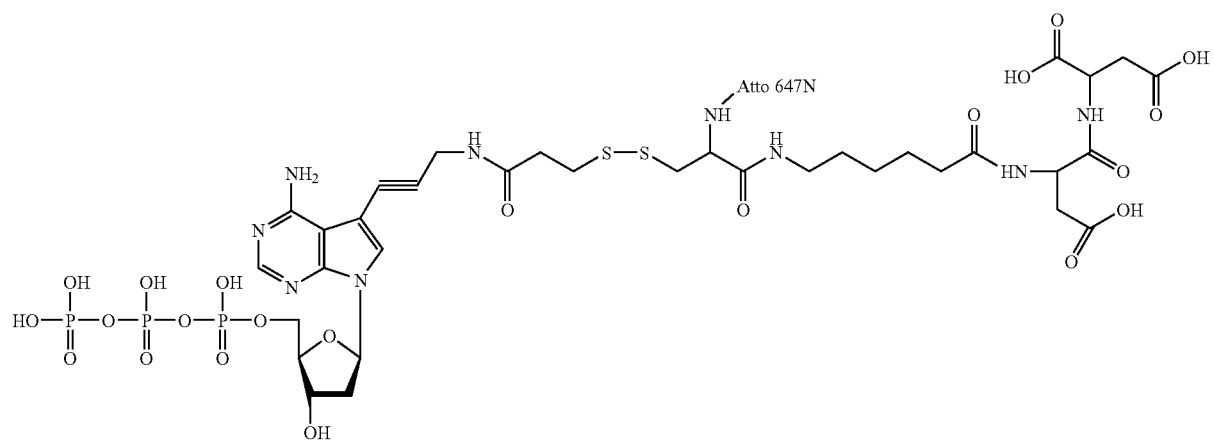
26

Dye modified final products were prepared using following standard conditions: peptide modified dNTPs were re-dissolved in 20 mM $K_2HPO_4$ and dye-NHS dissolved in anhydrous DMF (5 mg in 100 µl) was added using initially 1.2 eqv. up to 4 eqv. to reach complete consumption of starting material. Progress of modification was monitored using LC-MS. Product was isolated using preparative HPLC (C18 column) with 1% $CH_3CN$ gradient and 50 mM TEAB, pH 8.6. Desired fractions were combined, organic solvent removed under reduced pressure and products subjected to $CH_3OH$ repurification on C18 HPLC column (1% $CH_3OH$ gradient). Final fractions were quantitated at 650 nm using $\epsilon_{650}=250000$ $M^{-1}$ $cm^{-1}$ for Cy5 dye and 150000 $M^{-1}$ $cm^{-1}$ for Atto 647N dye.

Example 3

Caproic-Arg-Arg-Arg

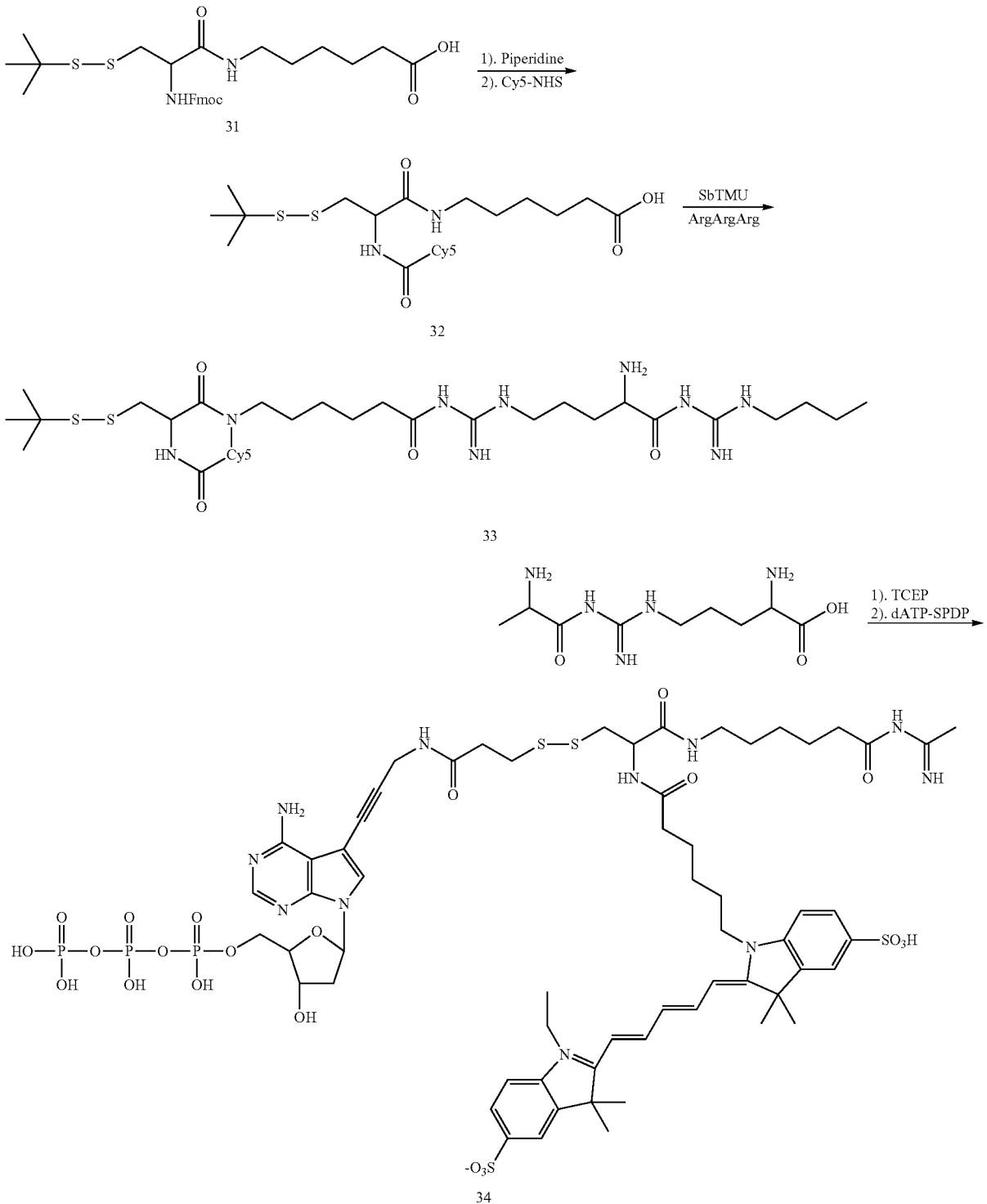

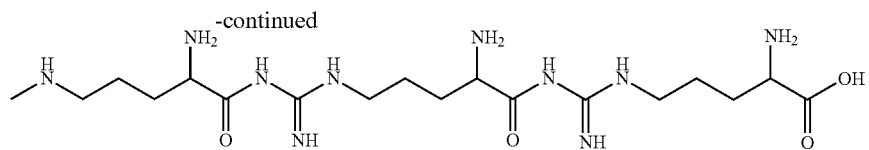

Compound 32

Compound 31 (100 mg, 0.18 mmol) was dissolved in 0.8 ml DMF and added 0.2 mL piperidine and then kept at RT for 30 min. DMF was removed and the residue was purified with flash column using $CH_2Cl_2$: $CH_3OH$ (2:1). The purified amine (35 mg) was dissolved in 1 mL DMF and used directly for the next step without characterization. 3.5 mg of the purified amine in 0.1 mL DMF (10.8 µmol) was added 60 µL DMF and 40 µL DIPEA and then Cy5 Mono NHS Ester (6.63 µmol) in 100 µL anhydrous DMF was added into the solution. After 30 minutes, the reaction mixture was purified with HPLC (Waters Delta 600 pump and 2487 Dual λ Absorbance Detector, Phenomenex C18 preparative column, 250×21.00 mm 10 micron, gradient: 100% A for 5 min, then 1% B/min, buffer A 0.05 M TEAB, buffer B $CH_3CN$, 10 mL/min flow). Fractions containing the desired compound 32 were pooled and quantified; (3.0 µmol, 45%, $\epsilon_{649}$=250000); ESI-MS (negative ion mode): m/z=959.20 (M-H).

Compound 33

The NHS ester of the acid 32 was prepared by dissolving the acid 32 (3.0 µmol) in DMF (500.0 µL) and N,N,N',N'-Tetramethyl-O—(N-succinimidyl)uronium hexafluorophosphate (SbTMU) (4.3 mg, 12 µmol) in 100 µL DMF was added to the acid solution followed by the addition of DIPEA (80 µL). After stirring at RT for 1 hr., the reaction mixture was used immediately for peptide coupling without any purification. The peptide Arg-Arg-Arg-OH (14.5 mg, 30 µmol) was dissolved in 160 µL 0.5M phosphate buffer, and added to the freshly prepared NHS ester of the acid 32. The reaction mixture was stirred for 30 minutes and then the crude reaction mixture was purified with HPLC (Waters Delta 600 pump and 2487 Dual λ Absorbance Detector, Phenomenex C18 preparative column, 250×21.00 mm 10 micron, gradient: 100% A for 5 min, then 1% B/min, buffer A 0.05 M TEAB, buffer B MeCN, 10 mL/min flow). Fractions containing the desired compound 33 were pooled and quantified; (0.6 µmol, 20%, $\epsilon_{649}$=250000); ESI-MS (negative ion mode): m/z=713.45 [(M−2H)/2].

Compound 34

A solution of compound 33 (0.6 µmol) in 3 ml $H_2O$ was treated with TCEP (300 µL, 1M solution) in an aluminum foil covered flask. After 30 minutes, the reaction mixture was purified with HPLC (Waters Delta 600 pump and 2487 Dual λ Absorbance Detector, Phenomenex C18 preparative column, 250×21.00 mm 10 micron, gradient: 100% A for 5 min, then 1% B/min, buffer A 0.05 M TEAB, buffer B $CH_3CN$, 10 mL/min flow). Fractions containing the desired thiol, analyzed with ESI-MS (negative ion mode): m/z=669.90 [(M-2H)/2], were pooled and immediately added dATP-SPDP (1 mmol in 1 mL $H_2O$). After 15 minutes, LCMS analysis indicated that the completion of the reaction and the reaction mixture was then partially concentrated under reduced pressure to remove $CH_3CN$, then purified with HPLC (Waters Delta 600 pump and 2487 Dual λ Absorbance Detector, Phenomenex C18 preparative column, 250×10.00 mm 10 micron, gradient: 100% A for 5 min, then 1% B/min, buffer A 0.05M TEAB, buffer B $CH_3CN$, 5 mL/min flow). Fractions containing the desired compound were pooled and concentrated and then purified again with HPLC using $CH_3OH$ and TEAB buffer. The fractions containing the desired compound 34 were pooled and lyophilized to yield compound 34 as a bright blue solid (0.37 µmol, 62%, $\epsilon_{649}$=250000). ESI-MS (negative ion mode): m/z=983.75 [(M-2H)/2].

Example 4

Cap-Asp-Asp-Asp-Asp

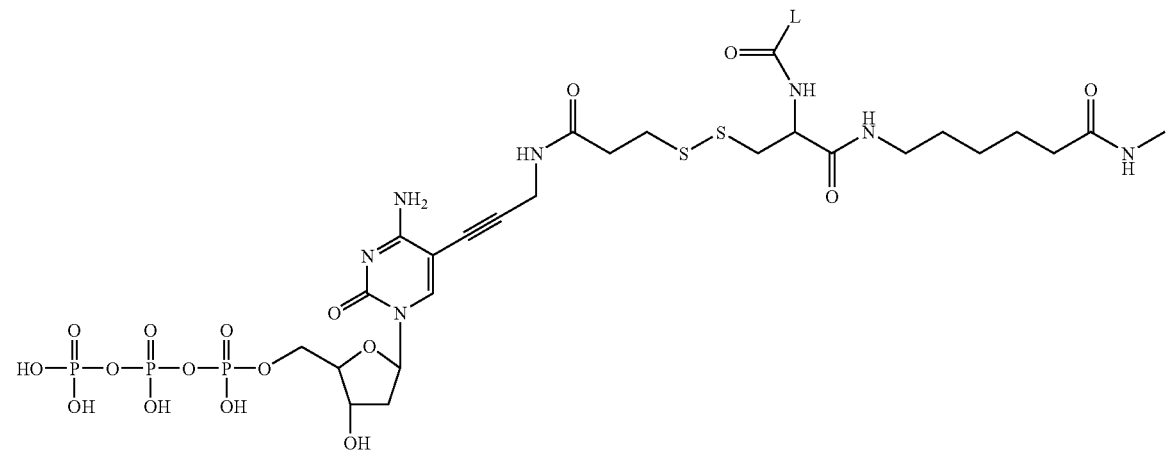

-continued
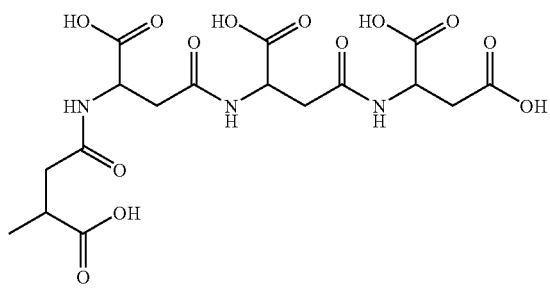
48a: L = Cy5
48b: L = Atto647N
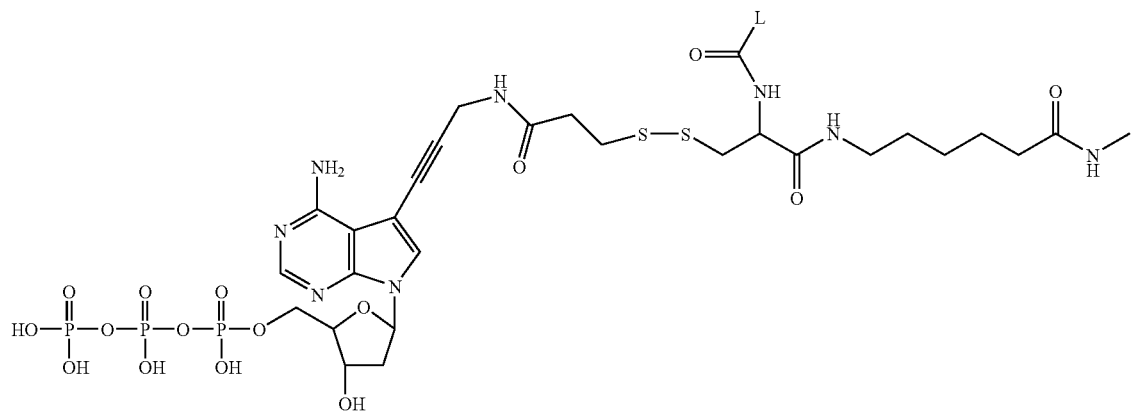
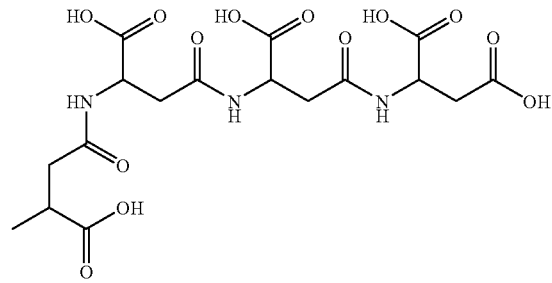
49a: L = Cy5
49b: L = Atto647N
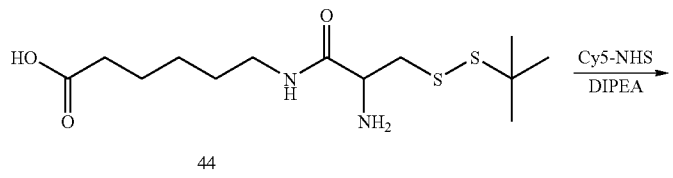
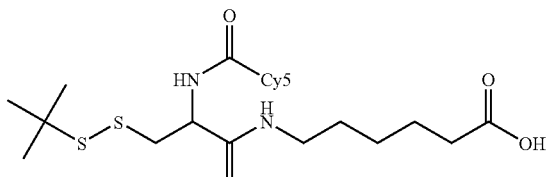

Compound 45

Cy5 Mono NHS Ester (100.0 µL, 6.63 µmol) in anhydrous DMF was added to a solution of amine 44 (13.26 µmol, 2 equiv) in DMF (100 µL) and DIPEA (20.0 µL) in an aluminum foil covered flask. After 30 minutes, the disappearance of the starting amine was determined by LCMS or HPLC. The reaction was HPLC purified (Waters Delta 600 pump and 2487 Dual λ Absorbance Detector, Phenomenex C18 preparative column, 250×21.00 mm 10 micron, gradient: 100% A for 5 min, then 1% B/min, buffer A 0.05 M TEAB, buffer B CH$_3$CN, 10 mL/min flow). Fractions containing the desired product were pooled and quantified; (4.0 µmol, 60.3%, $\epsilon_{649}$=250000); ESI-MS (negative ion mode): m/z=959.20 (M-H).

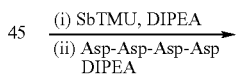

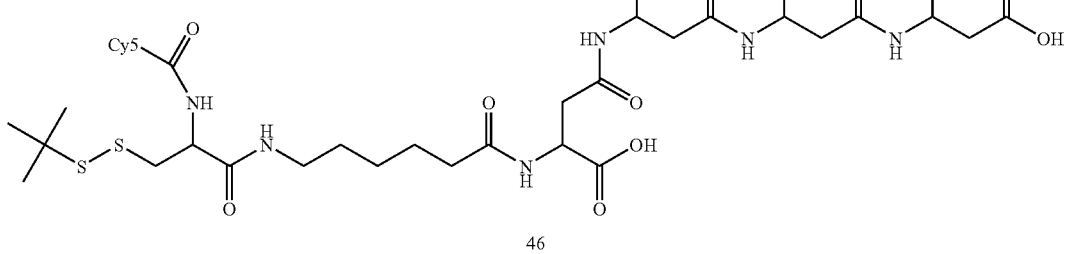

46

Compound 46

The NHS ester of the acid 45 was prepared by dissolving the acid 45 (4.0 µmol, 1 eqv.) in DMF (700.0 µL) and the SbTMU 5.93 mg, 16.5 µmol, in 200 µL DMF, 4.0 eqv.) was added, to the acid solution followed by the addition of DIPEA (103.0 µL). After stirring at RT for 1 hour, the reaction mixture was used immediately for peptide coupling without any purification. The peptide (Asp-Asp-Asp-Asp) was dissolved in DMF:H$_2$O (400.0 µL, 1:1), basified using DIPEA (50.0 µL). To this peptide solution was added freshly prepared NHS ester of the acid 45. The reaction mixture was stirred for 30 minutes and it was then analyzed by LCMS. The crude reaction mixture was HPLC purified (Waters Delta 600 pump and 2487 Dual λ Absorbance Detector, Phenomenex C18 preparative column, 250×21.00 mm 10 micron, gradient: 100% A for 5 min., then 1% B/min, buffer A 0.05 M TEAB, buffer B CH$_3$CN, 10 mL/min flow). Fractions containing the desired were pooled and quantified; (3.0 µmol, 75.0%, $\epsilon_{649}$=250000); ESI-MS (negative ion mode): m/z=709.20 (½M-H).

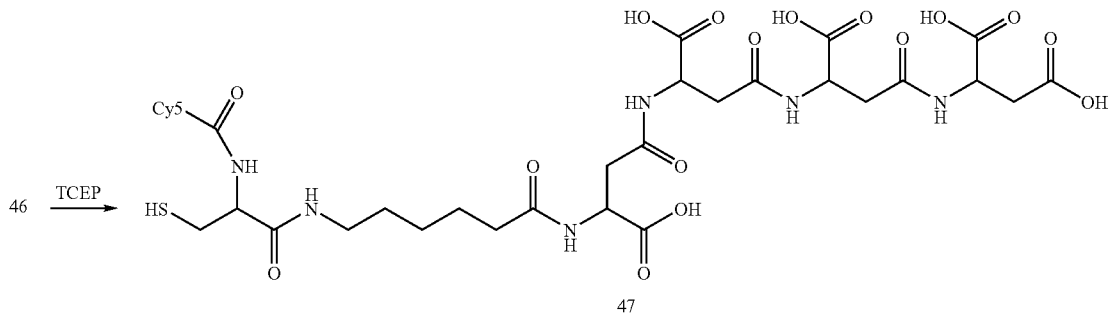

47

Compound 47

A solution of compound 46 (1.0 μmol) in H₂O was treated with TCEP (40.0 μL, 19.92 μmol, 0.5 M in H₂O, 19.92 equiv) in an aluminum foil covered flask. After 30 minutes, the reaction mixture was analyzed by LCMS and was then HPLC purified (Waters Delta 600 pump and 2487 Dual λ Absorbance Detector, Phenomenex C18 preparative column, 250× 21.00 mm 10 micron, gradient: 100% A for 5 min., then 1% B/min, buffer A 0.05 M TEAB, buffer B CH₃CN, 10 mL/min flow). Fractions containing the desired were pooled and used immediately for the subsequent displacement reaction without removing the solvent. ESI-MS (negative ion mode): m/z=665.45 (½M-H).

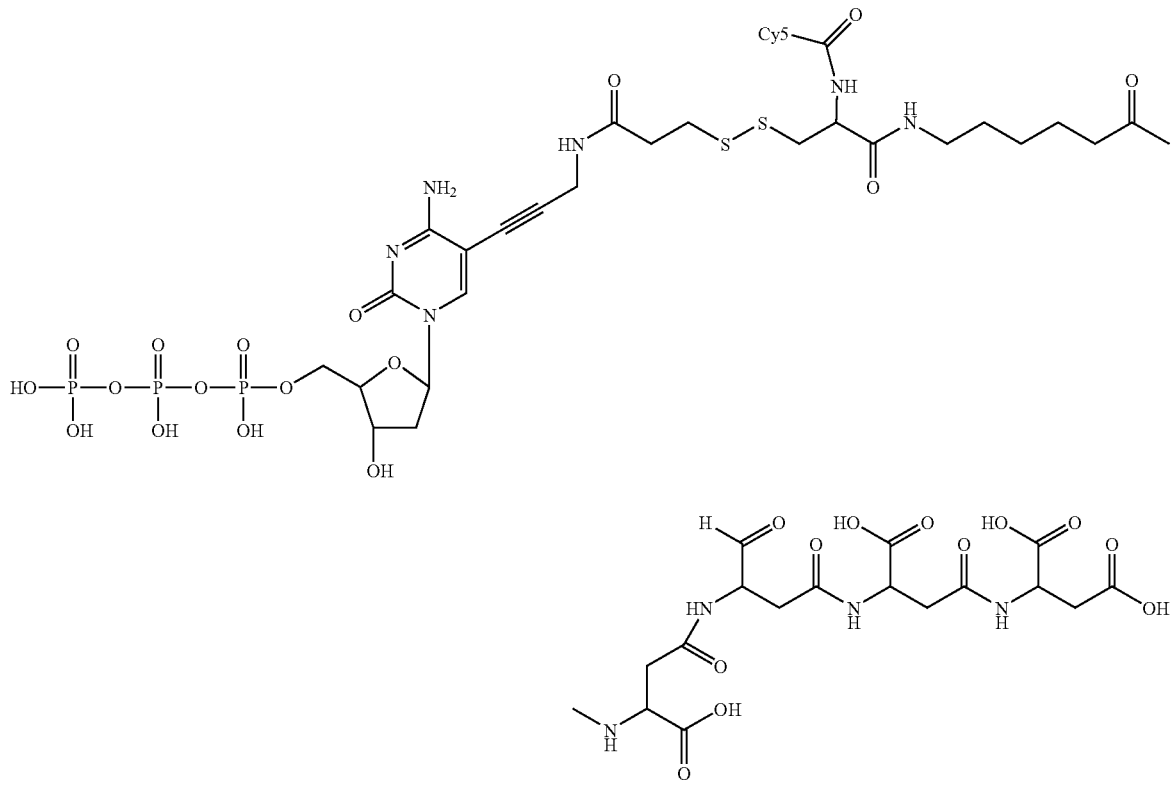

48a

Compound 48a

HPLC fractions containing the thiol 7 (0.34 μmol, 1 eqv.) were mixed with HPLC fractions containing dCTP-SPDP (0.41 μmol, 1.25 eqv.) in an aluminum foil covered flask. After 15 min. LCMS analysis indicated that the completion of the reaction and it was then partially concentrated under reduced pressure to remove CH₃CN, then HPLC purified (Waters Delta 600 pump and 2487 Dual λ Absorbance Detector, Phenomenex C18 preparative column, 250×10.00 mm 10 micron, gradient: 100% A for 5 min, then 1% B/min, buffer A 0.05 M TEAB, buffer B CH₃CN, 5 mL/min flow). Fractions containing the desired were pooled and lyophilized to yield compound 1 as a bright blue solid (0.17 μmol, 50%, ±649=250000). The desired product was HPLC purified a second time under the same conditions, using CH₃OH instead of CH₃CN for buffer B. Fractions containing the desired were pooled and stored at −80° C. without removing the solvent. ESI-MS (negative ion mode): m/z=968.35 (½M-H).

-continued

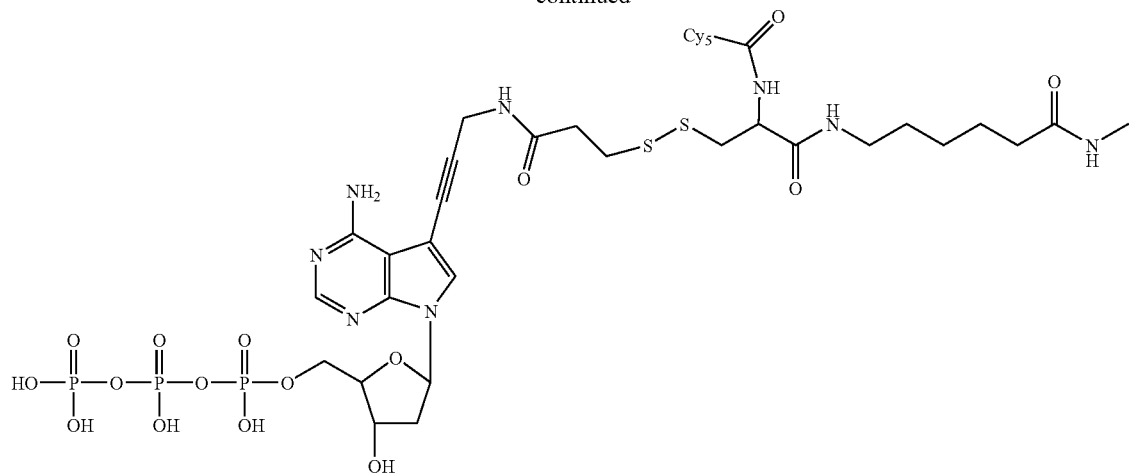

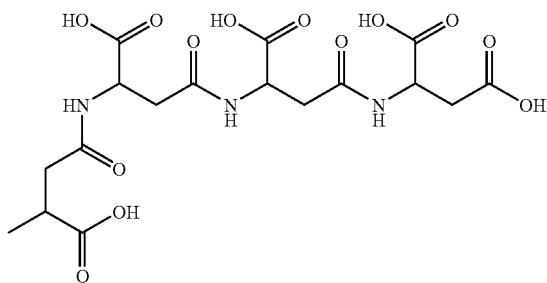

49a

Compound 49a

HPLC fractions containing thiol 47 (0.5 μmol, 1 eqv.) were mixed with HPLC fractions containing dATP-SPDP (0.6 μmol, 1.2 eqv.) in an aluminum foil covered flask. After 15 min. LCMS analysis indicated that the completion of the reaction and it was then partially concentrated under reduced pressure to remove $CH_3CN$, then HPLC purified (Waters Delta 600 pump and 2487 Dual λ Absorbance Detector, Phenomenex C18 preparative column, 250×10.00 mm 10 micron, gradient: 100% A for 5 min., then 1% B/min, buffer A 0.05M TEAB, buffer B $CH_3CN$, 5 mL/min flow). Fractions containing the desired were pooled and lyophilized to yield compound 49a as a bright blue solid (0.35 μmol, 70%, $\epsilon_{649}$=250000). The desired was HPLC purified a second time under the same conditions, using $CH_3OH$ instead of $CH_3CN$ for buffer B. Fractions containing the desired were pooled and stored at −80° C. without removing the solvent. ESI-MS (negative ion mode): m/z=980.10 (½M-H).

Example 5

Caproic-Asp

Synthesic Scheme IV

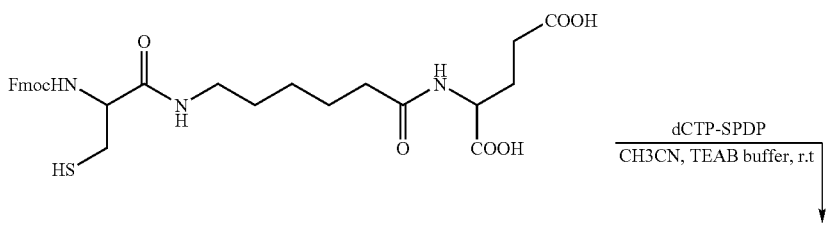

dCTP-SPDP
―――――――――――
CH3CN, TEAB buffer, r.t

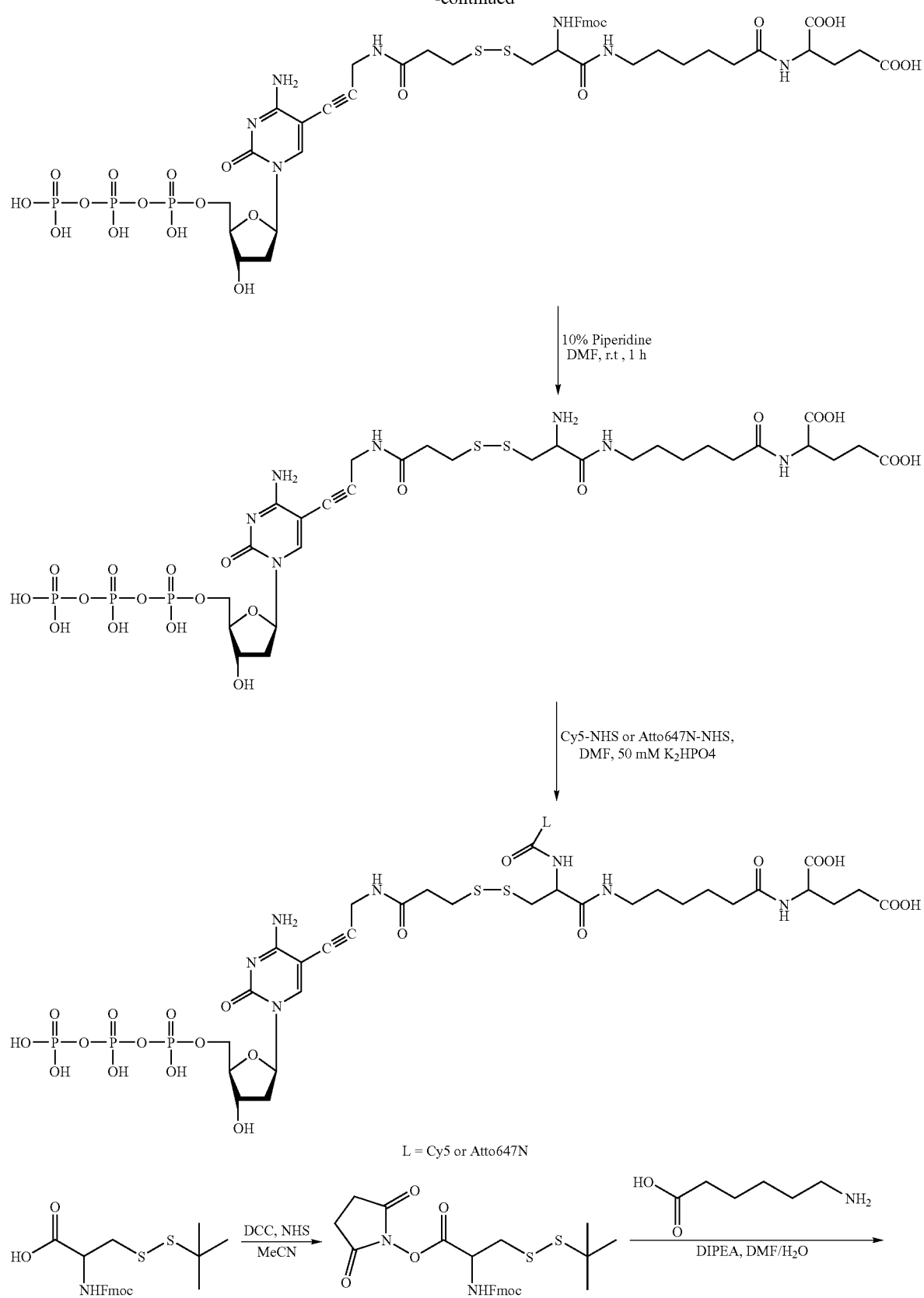
-continued
L = Cy5 or Atto647N

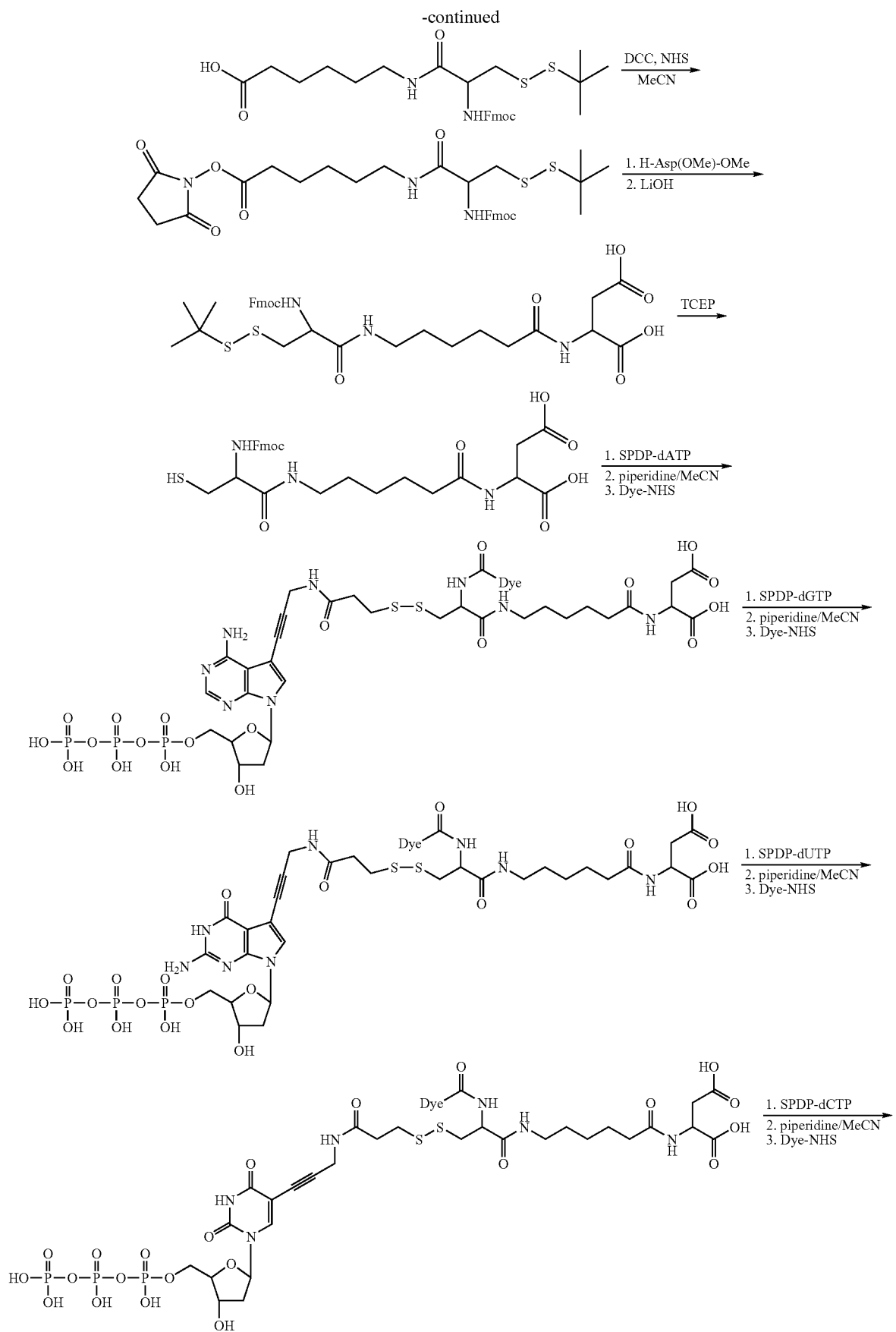

-continued

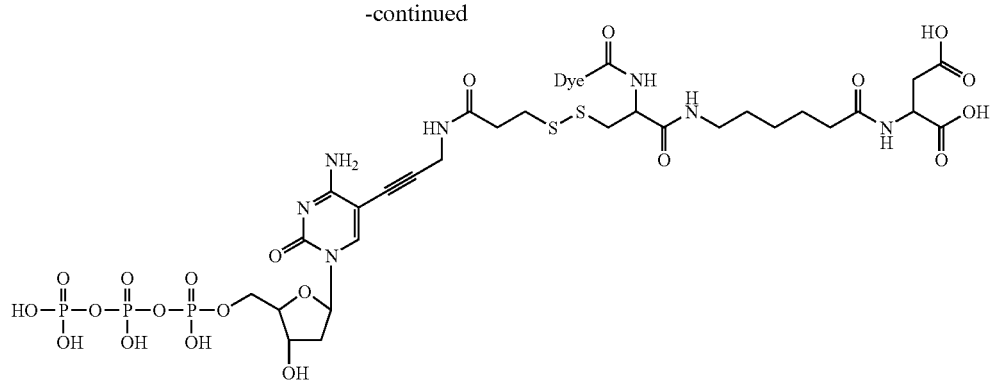

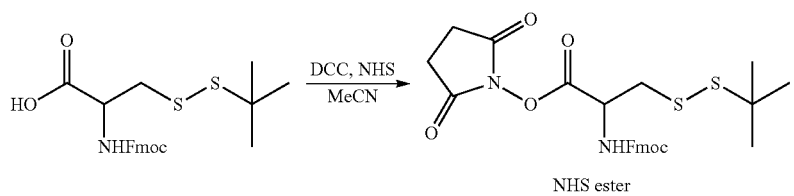

NHS ester

Fmoc-Cys(StBu)-OH (2.0 g, 4.63 mmol, 1 eqv.) was dissolved in CH$_3$CN (10 mL). DCC (1.2 g, 5.81 mmol, 1.26 eqv.) was added, followed by NHS (0.70 g, 6.08 mmol, 1.31 eqv.) and the reaction was stirred at RT for 1 hr. White precipitate (DCU) began forming within five min. The reaction mixture was transferred to Eppendorf tubes and centrifuged to remove the white precipitate. The supernatant was then used in subsequent reactions without further purification.

clear up the solution. The reaction was stirred at RT for two hours, then quenched with 20 mL 10% HCl (aq.). The aqueous phase was extracted with CH$_2$Cl$_2$ (2×50 mL). The organic phase was dried over Na$_2$SO$_4$, filtered, and concentrated under reduced pressure to yield a brown oil. Purification by flash column chromatography (100% CH$_2$Cl$_2$ to 5% CH$_3$OH/CH$_2$Cl$_2$) afforded the desired acid as a white foam (2.14 g, 86%).

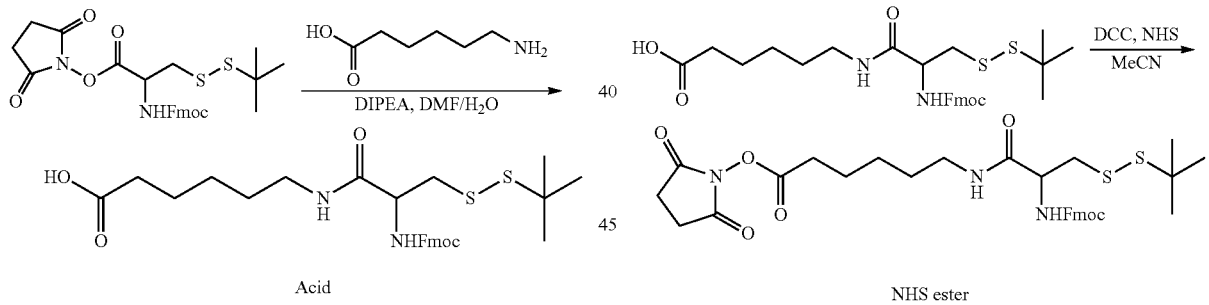

Acid

NHS ester

6-Aminohexanoic acid (0.60 g, 4.57 mmol, 1 eqv.) was dissolved in 1:1H$_2$O:DMF (6 mL total). DIPEA (0.016 mL) was added to keep the pH about 8. NHS ester (4.63 mmol in 10 mL CH$_3$CN, 1.01 eqv.) was added to the reaction mixture in 1 mL aliquots over about 10 min. DIPEA (0.02 mL) was added after each aliquot to keep the reaction basic. After the first aliquot of NHS ester was added, the reaction became cloudy, and addition of extra H$_2$O (0.2 mL) was needed to The starting acid (0.99 g, 1.82 mmol, 1 eqv.) was dissolved in CH$_3$CN (10 mL). DCC (0.46 g, 2.23 mmol, 1.23 eqv.) was added, followed by NHS (0.28 g, 2.43 mmol, 1.34 eqv.) and the reaction was stirred at RT for an hour. White precipitate (DCU) began forming within 5 min. The reaction mixture was transferred to Eppendorf tubes and centrifuged to remove the white precipitate. The supernatant was then used in subsequent reactions without further purification.

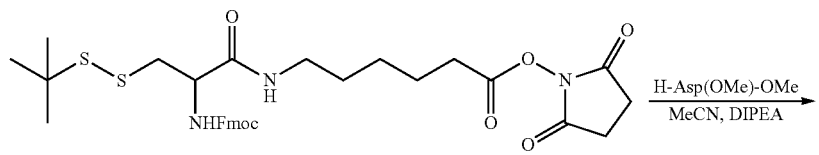

-continued

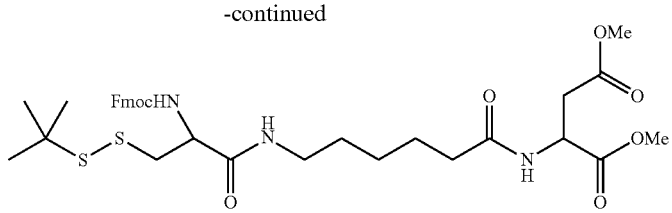

Dimethyl ester

L-Aspartic acid dimethyl ester hydrochloride (0.2 g, 1.01 mmol, 2 eqv.) was dissolved in CH₃CN (1 mL) and DIPEA (0.32 mL, 1.84 mmol, 4 eqv.). A solution of NHS ester (0.48 mmol, 1 eqv.) in CH₃CN (2 mL) was added, and the reaction was stirred at RT for 12 hr. The reaction was diluted with EtOAc (25 mL), then washed with brine (1×30 mL) and sat. NH₄Cl (aq.) (1×30 mL). The organic phase was dried over Na₂SO₄, filtered, and concentrated under reduced pressure. Purification by flash column chromatography (100% CH₂Cl₂ to 2% CH₃OH/CH₂Cl₂) afforded the desired ester as a white foam (0.12 g, 36%).

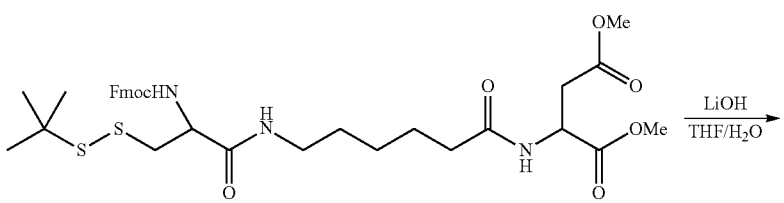

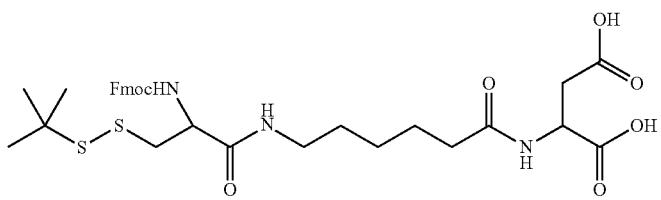

Diacid

1M LiOH(aq) (0.18 mL, ≠6 equiv) was added to a solution of dimethyl ester (0.02 g, 0.029 mmol, 1 eqv.) in THF (0.30 mL). The reaction was stirred at RT until the starting dimethyl ester was consumed based on LCMS analysis (about 15 min). The crude reaction was then HPLC purified (Waters Delta 600 pump and 2487 Dual λ Absorbance Detector, Phenomenex C18 preparative column, 250×21.2 mm 10 micron, gradient: 90% A for 3 min., then 5% B/min., buffer A 0.05M TEAB, buffer B CH₃CN, 10 mL/min. flow). Fractions containing the desired were pooled and concentrated to yield the desired diacid, which was used for subsequent reactions without quantifying.

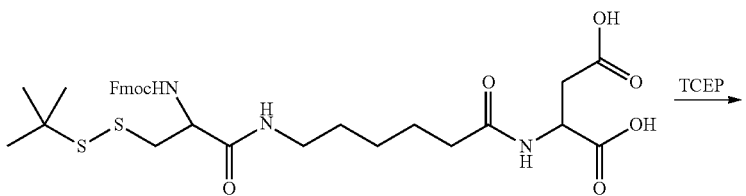

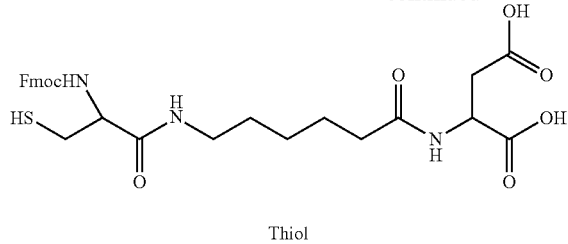

Thiol

Diacid (~29 μmol, 1 eqv.) was treated with TCEP (1.7 mL, 0.85 mmol, 0.5M in H₂O, 29 eqv.). The reaction was stirred at RT until the starting material was consumed based on LCMS analysis (about 30 min.). The crude reaction was then HPLC purified (Waters Delta 600 pump and 2487 Dual λ Absorbance Detector, Phenomenex C18 preparative column, 250× 21.2 mm 10 micron, gradient: 100% A for 3 min, then 5% B/min., buffer A 0.05M TEAB, buffer B CH₃CN, 10 mL/min. flow). Fractions containing the desired were pooled and used for subsequent reactions without concentrating or quantifying.

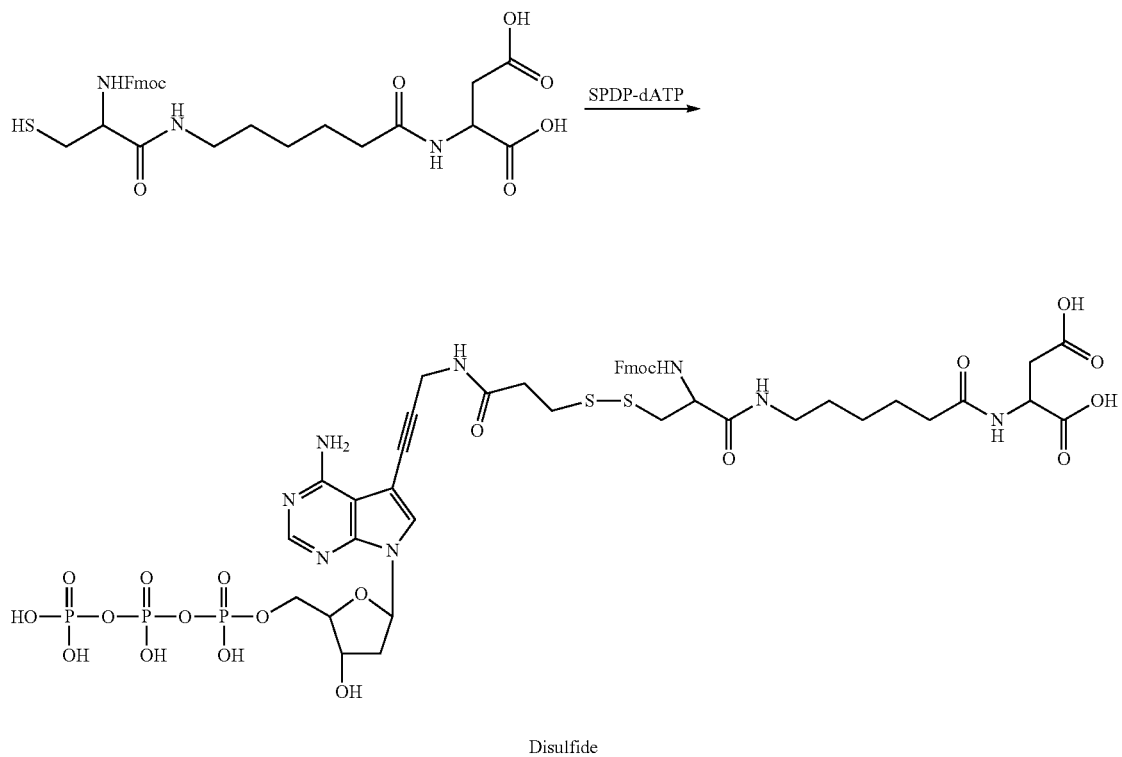

Disulfide

HPLC fractions containing the thiol (about 10 μmol, 2 eqv.) were mixed with HPLC fractions containing SPDP-dATP (5 μmol, 1 equiv). After the SPDP-dATP was consumed based on LCMS analysis (about 10 min), the reaction was partially concentrated under reduced pressure to remove CH₃CN and then HPLC purified (Waters Delta 600 pump and 2487 Dual λ Absorbance Detector, Phenomenex C18 preparative column, 250×15.0 mm 10 micron, gradient: 100% A for 3 min, then 1% B/min., buffer A 0.05M TEAB, buffer B CH₃CN, 10 mL/min. flow). Fractions containing the desired were pooled and lyophilized, then used for subsequent reactions without quantifying.

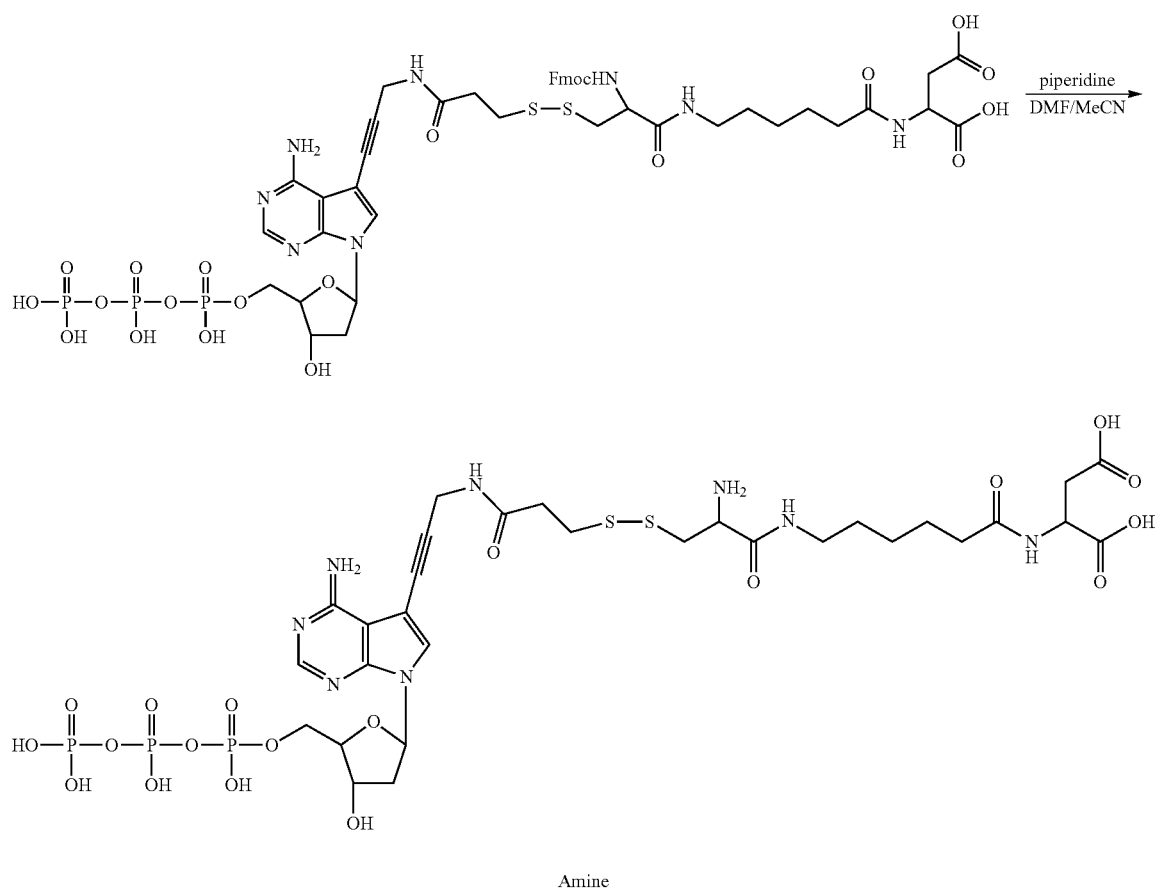

Amine

The starting carbamate (~5 µmol, 1 eqv.) was treated with 20% piperidine in 1:1 DMF:CH$_3$CN (2 mL), and stirred at RT until the starting material was consumed based on LCMS analysis (~15 min). After removing the solvent under reduced pressure, the reaction was HPLC purified (Waters Delta 600 pump and 2487 Dual λ Absorbance Detector, Phenomenex C18 preparative column, 250×21.2 mm 10 micron, gradient: 100% A for 3 min, then 1% B/min., buffer A 0.05M TEAB, buffer B CH$_3$OH, 10 mL/min. flow). Fractions containing the desired were pooled and lyophilized to yield the product as a white foam (1 µmol, 20%, $\epsilon_{280}$=12700).

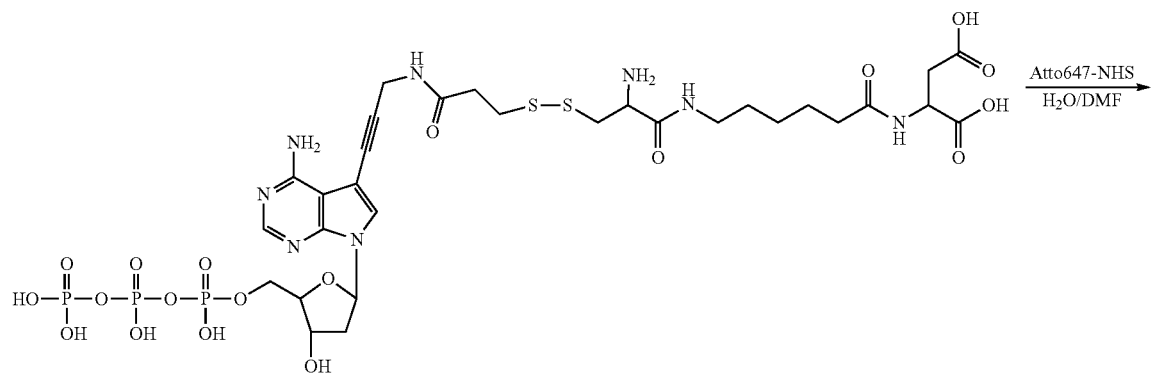

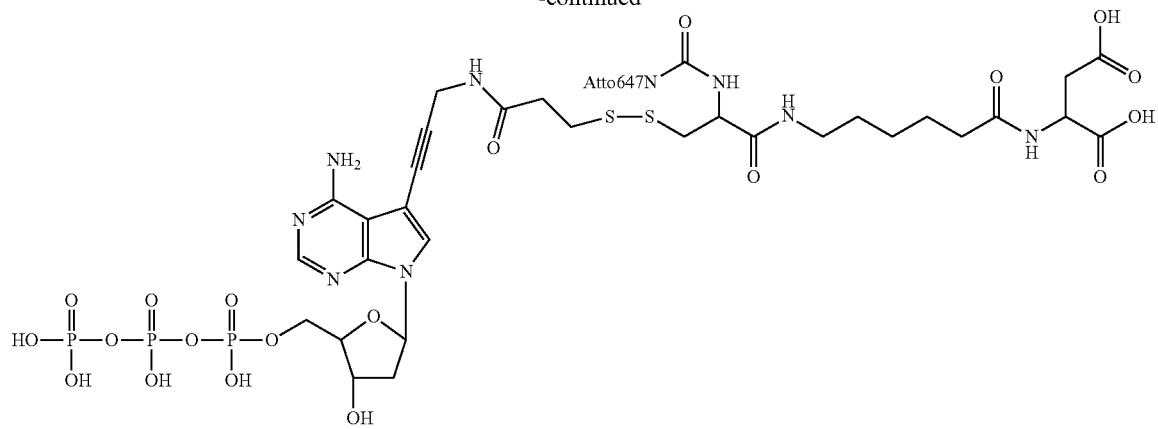

A* Caproic-Asp

Atto647N-NHS ester (0.030 mL, 1.8 μmol, 0.06M in anhydrous DMF, 3.6 eqv.) was added to a solution of amine (0.5 μmol, 1 eqv.) in $H_2O$ (0.25 mL) in 10 μl aliquots. The reaction was monitored by LCMS to determine how much dye was needed to consume the starting amine. After disappearance of amine, the crude reaction was HPLC purified (Waters Delta 600 pump and 2487 Dual λ Absorbance Detector, Phenomenex C18 preparative column, 250×10.0 mm 10 micron, gradient: 100% A for 3 min, then 2% B/min., buffer A 0.05M TEAB, buffer B $CH_3CN$, 5 mL/min. flow). Fractions containing the desired were pooled and concentrated, then HPLC purified a second time under the same conditions, using $CH_3OH$ instead of $CH_3CN$ for buffer B. Fractions containing the desired were pooled and stored at −80° C. without removing the solvent (0.086 μmol, 17%, $\epsilon_{645}$=150000).

HPLC fractions containing the thiol (~10 μmol, 6 eqv.) were mixed with HPLC fractions containing SPDP-dGTP (1.5 μmol, 1 eqv.). After the SPDP-dGTP was consumed based on LCMS analysis (about 10 min), the reaction was partially concentrated under reduced pressure to remove $CH_3CN$ and then HPLC purified (Waters Delta 600 pump and 2487 Dual λ Absorbance Detector, Phenomenex C18 preparative column, 250×10.0 mm 10 micron, gradient: 100% A for 3 min., then 1% B/min, buffer A 0.05M TEAB, buffer B $CH_3CN$, 5 mL/min. flow). Fractions containing the desired were pooled and lyophilized, then used for subsequent reactions without quantifying.

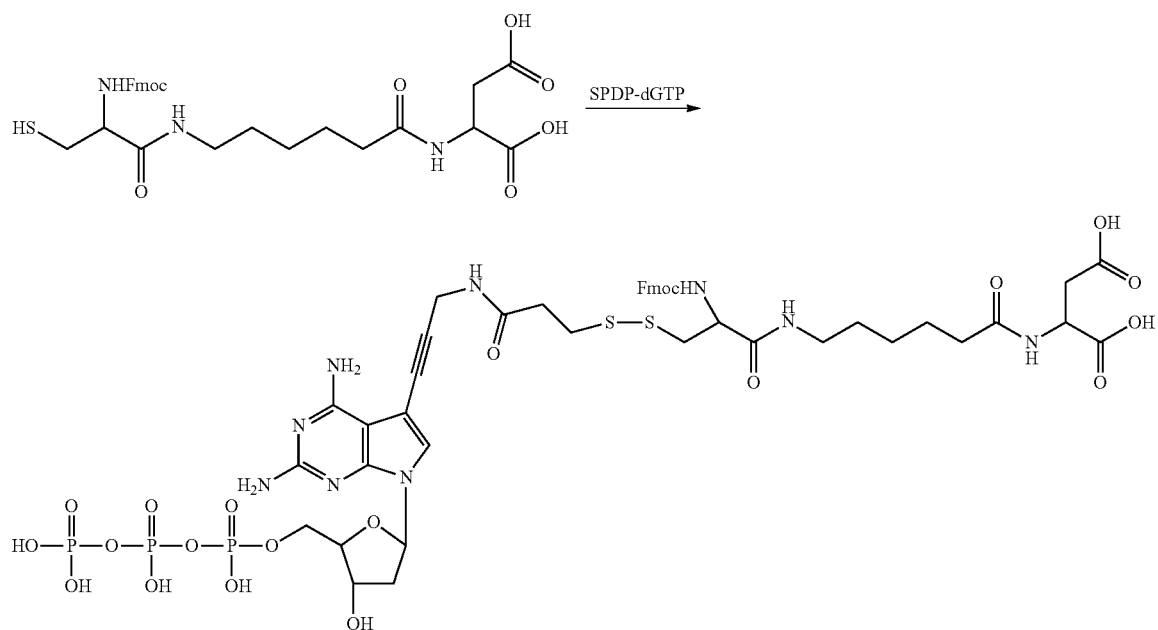

Disulfide

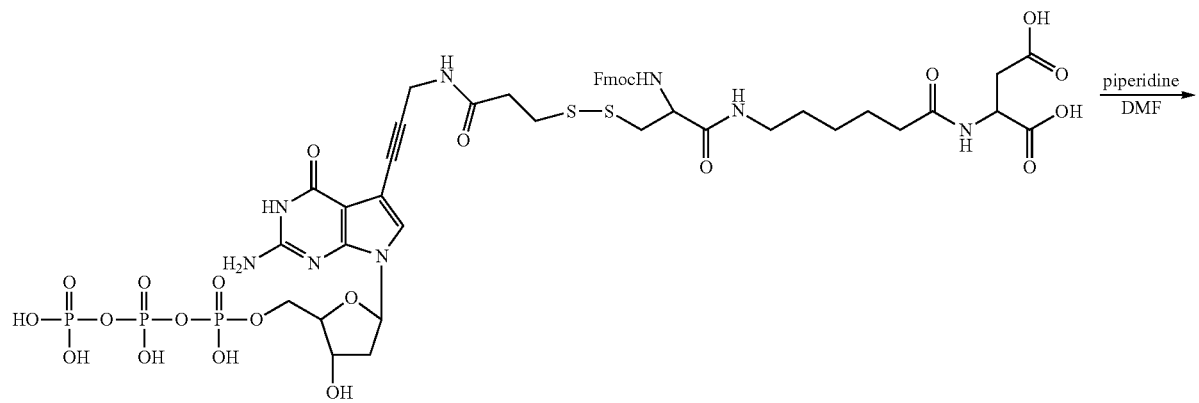

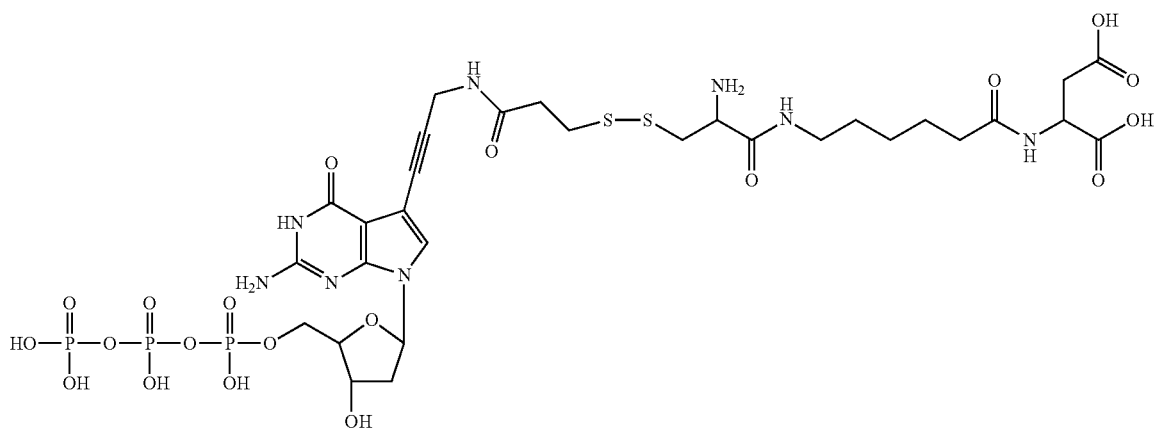

Amine

The starting carbamate (~1.5 μmol, 1 eqv.) was treated with 20% piperidine in DMF (0.5 mL), and stirred at RT until the starting material was consumed based on LCMS analysis (about 15 min). After removing the solvent under reduced pressure, the reaction was HPLC purified (Waters Delta 600 pump and 2487 Dual λ Absorbance Detector, Phenomenex C18 preparative column, 250×10.0 mm 10 micron, gradient: 100% A for 3 min, then 1% B/min., buffer A 0.05M TEAB, buffer B CH$_3$CN, 5 mL/min. flow). Fractions containing the desired were pooled and lyophilized to yield the product as a white foam (0.26 μmol, 17%, $\epsilon_{272}$=11900).

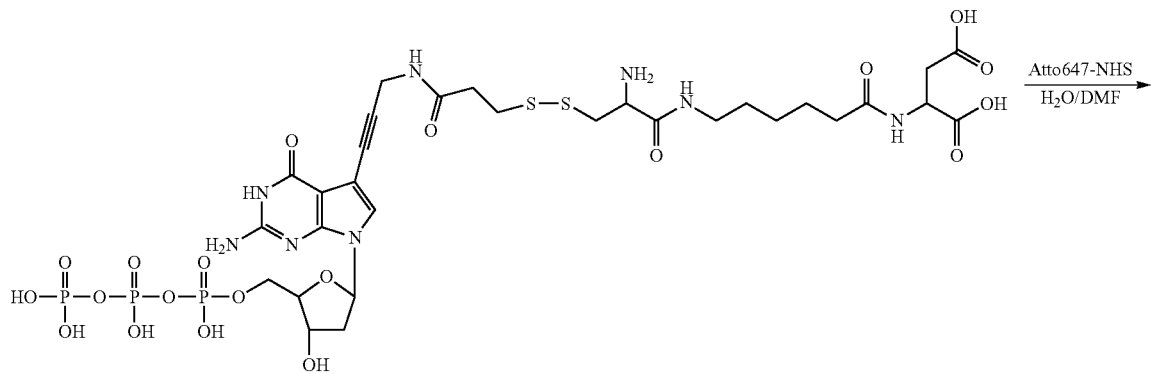

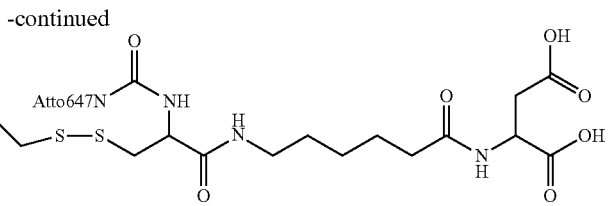
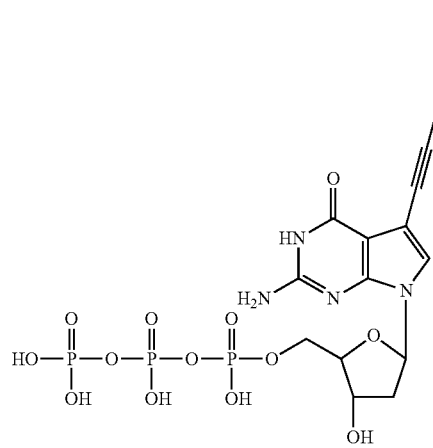

G* Caproic-Asp

Atto647N-NHS ester (0.011 mL, 0.66 μmol, 0.06 M in anhydrous DMF, 2.5 eqv.) was added to a solution of amine (0.26 μmol, 1 equiv) in H$_2$O (0.50 mL) in small aliquots. The reaction was monitored by LCMS to determine how much dye was needed to consume the starting amine. After disappearance of amine, the crude reaction was HPLC purified (Waters Delta 600 pump and 2487 Dual λ Absorbance Detector, Phenomenex C18 preparative column, 250×10.0 mm 10 micron, gradient: 100% A for 3 min, then 2% B/min., buffer A 0.05M TEAB, buffer B CH$_3$CN, 5 mL/min. flow). Fractions containing the desired were pooled and concentrated, then HPLC purified a second time under the same conditions, using CH$_3$OH instead of CH$_3$CN for buffer B. Fractions containing the desired were pooled and stored at −80° C. without removing the solvent (0.076 μmol, 29%, $\epsilon_{645}$=150000).

HPLC fractions containing the thiol (about 5 μmol, 5 eqv.) were mixed with SPDP-dCTP (1 μmol, 1 eqv.) in H$_2$O (0.20 mL). After the SPDP-dCTP was consumed based on LCMS analysis (about 10 min.), the reaction was partially concentrated under reduced pressure to remove CH$_3$CN and then HPLC purified (Waters Delta 600 pump and 2487 Dual λ Absorbance Detector, Phenomenex C18 preparative column, 250×21.2 mm 10 micron, gradient: 100% A for 3 min, then 3% B/min., buffer A 0.05M TEAB, buffer B CH$_3$CN, 5 mL/min. flow). Fractions containing the desired were pooled and lyophilized, then used for subsequent reactions without quantifying.

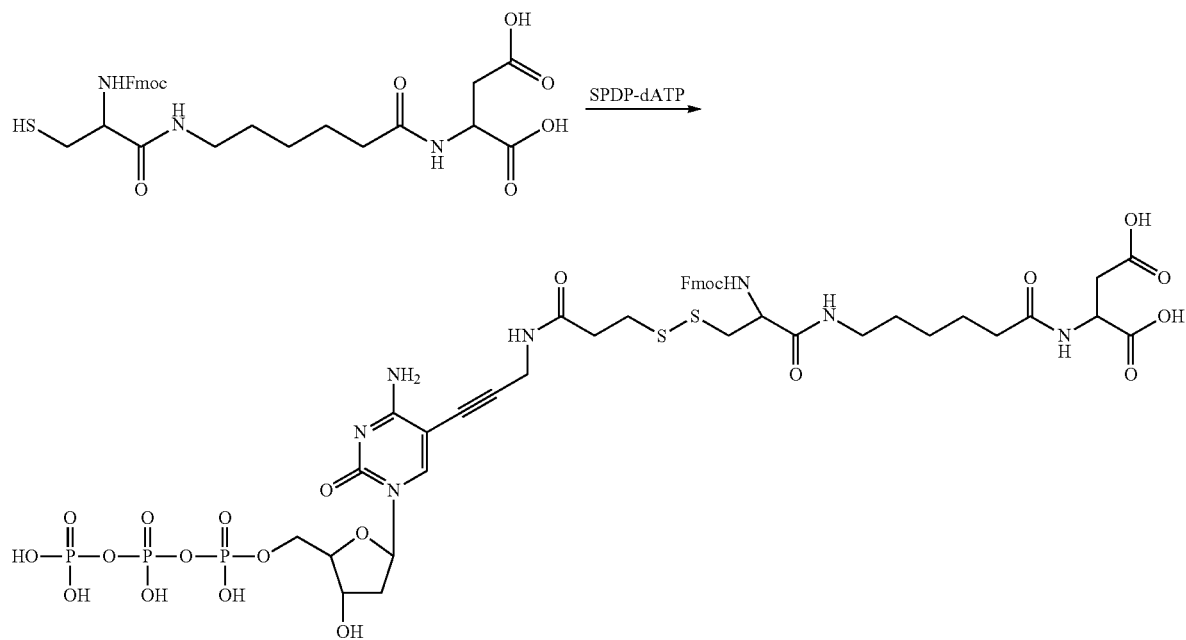

Disulfide

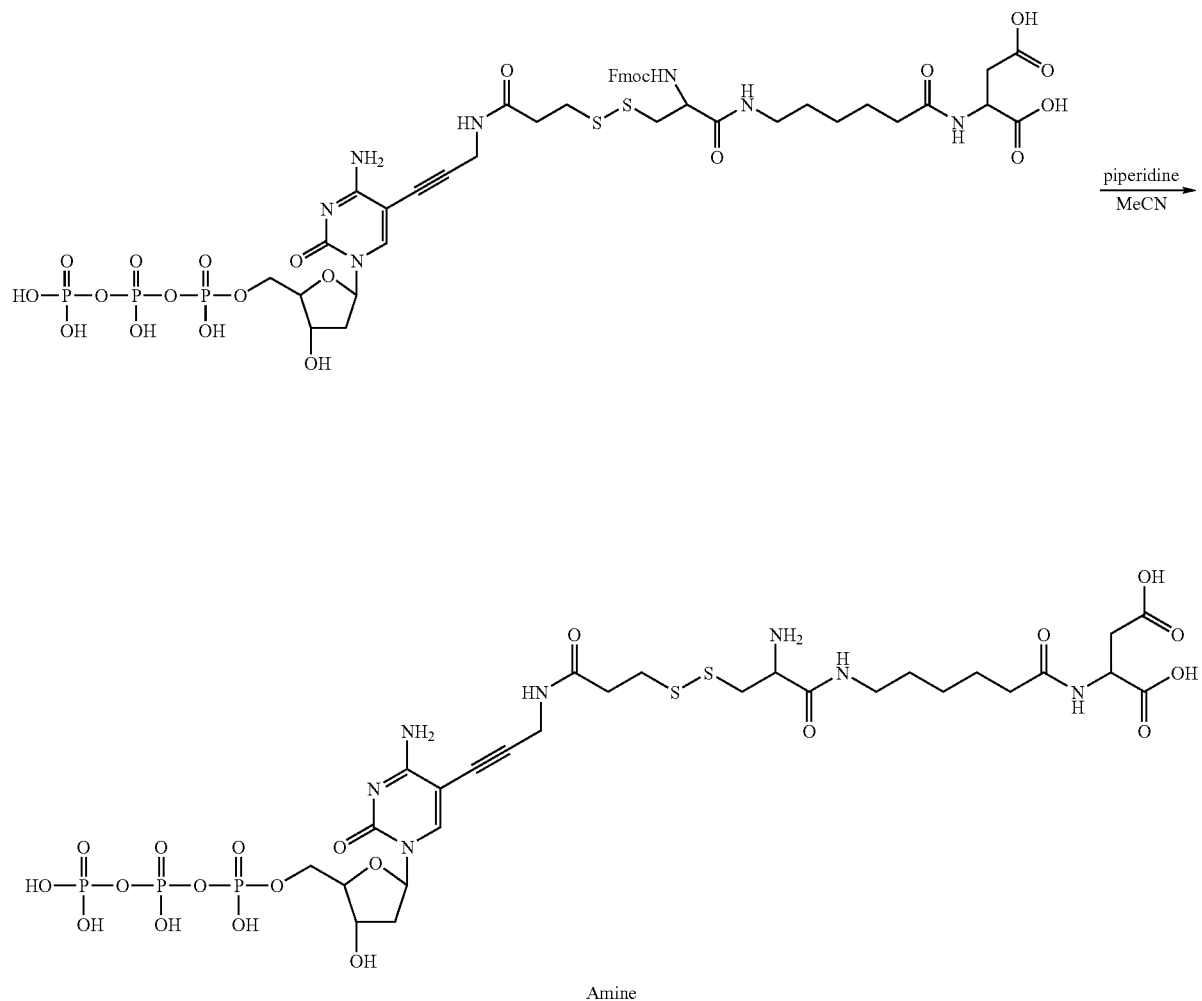

The starting carbamate (about 1 μmol, 1 eqv.) was treated with 20% piperidine in $CH_3CN$ (0.5 mL), and stirred at RT until the starting material was consumed based on LCMS analysis (~15 min). After removing the solvent under reduced pressure, the reaction was HPLC purified (Waters Delta 600 pump and 2487 Dual λ Absorbance Detector, Phenomenex C18 preparative column, 250×10.0 mm 10 micron, gradient: 100% A for 3 min., then 1% B/min, buffer A 0.05M TEAB, buffer B $CH_3CN$, 5 mL/min. flow). Fractions containing the desired were pooled and lyophilized to yield the product as a white foam (0.15 μmol, 15%, $\epsilon_{294}$=9300).

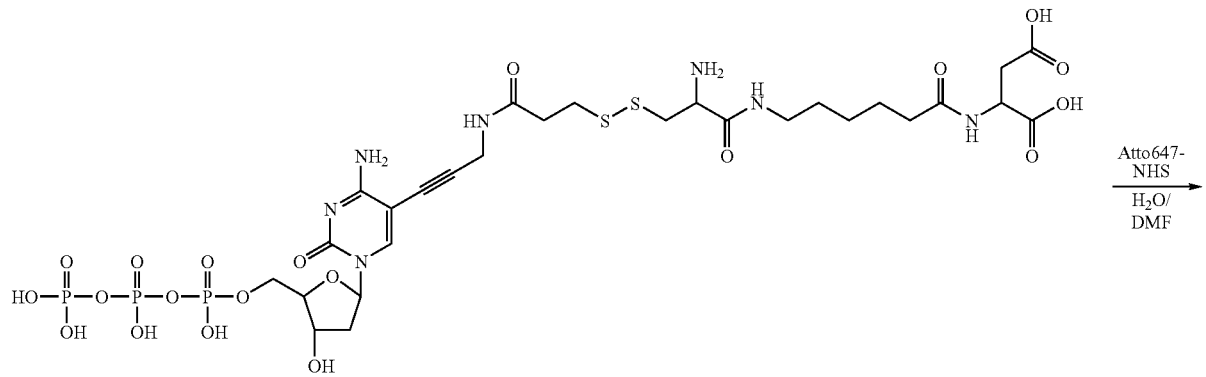

-continued

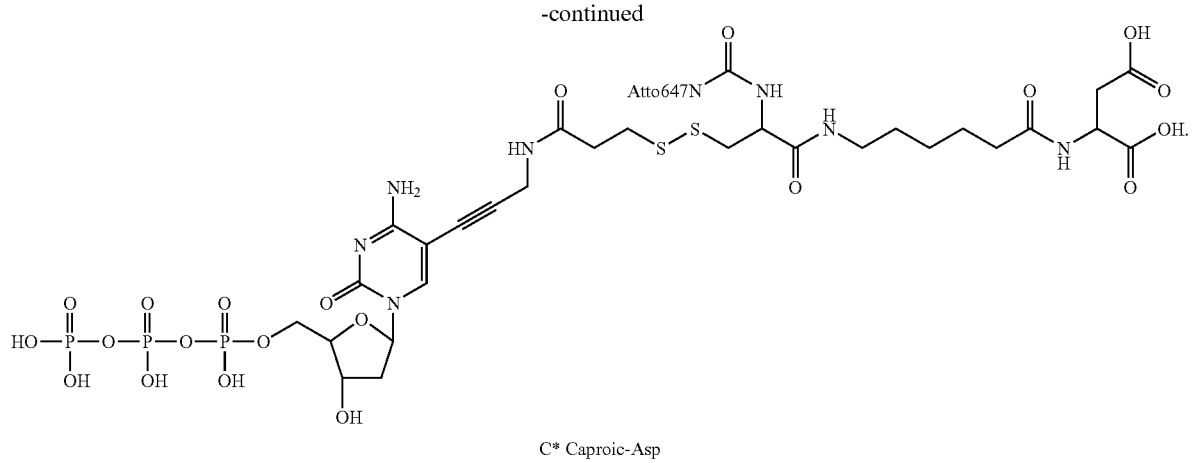

C* Caproic-Asp

Atto647N-NHS ester (0.012 mL, 0.72 µmol, 0.06M in anhydrous DMF, 3.6 eqv.) was added to a solution of amine (0.15 µmol, 1 eqv.) in H$_2$O (0.20 mL) in 5 µl aliquots. The reaction was monitored by LCMS to determine how much dye was needed to consume the starting amine. After disappearance of amine, the crude reaction was HPLC purified (Waters Delta 600 pump and 2487 Dual λ Absorbance Detector, Phenomenex C18 preparative column, 250×10.0 mm 10 micron, gradient: 100% A for 3 min., then 2% B/min., buffer A 0.05M TEAB, buffer B CH$_3$CN, 5 mL/min. flow). Fractions containing the desired were pooled and concentrated, then HPLC purified a second time under the same conditions, using CH$_3$OH instead of CH$_3$CN for buffer B. Fractions containing the desired were pooled and stored at −80° C. without removing the solvent (0.030 µmol, 20%, 645=150000).

HPLC fractions containing the thiol (~5 µmol, 2.5 equiv) were mixed with SPDP-dUTP (2 µmol, 1 eqv.) in H$_2$O (0.13 mL). After the SPDP-dUTP was consumed based on LCMS analysis (~10 min), the reaction was partially concentrated under reduced pressure to remove CH$_3$CN and then HPLC purified (Waters Delta 600 pump and 2487 Dual λ Absorbance Detector, Phenomenex C18 preparative column, 250× 10.0 mm 10 micron, gradient: 100% A for 3 min., then 1% B/min., buffer A 0.05M TEAB, buffer B CH$_3$CN, 5 mL/min. flow). Fractions containing the desired were pooled and lyophilized, then used for subsequent reactions without quantifying.

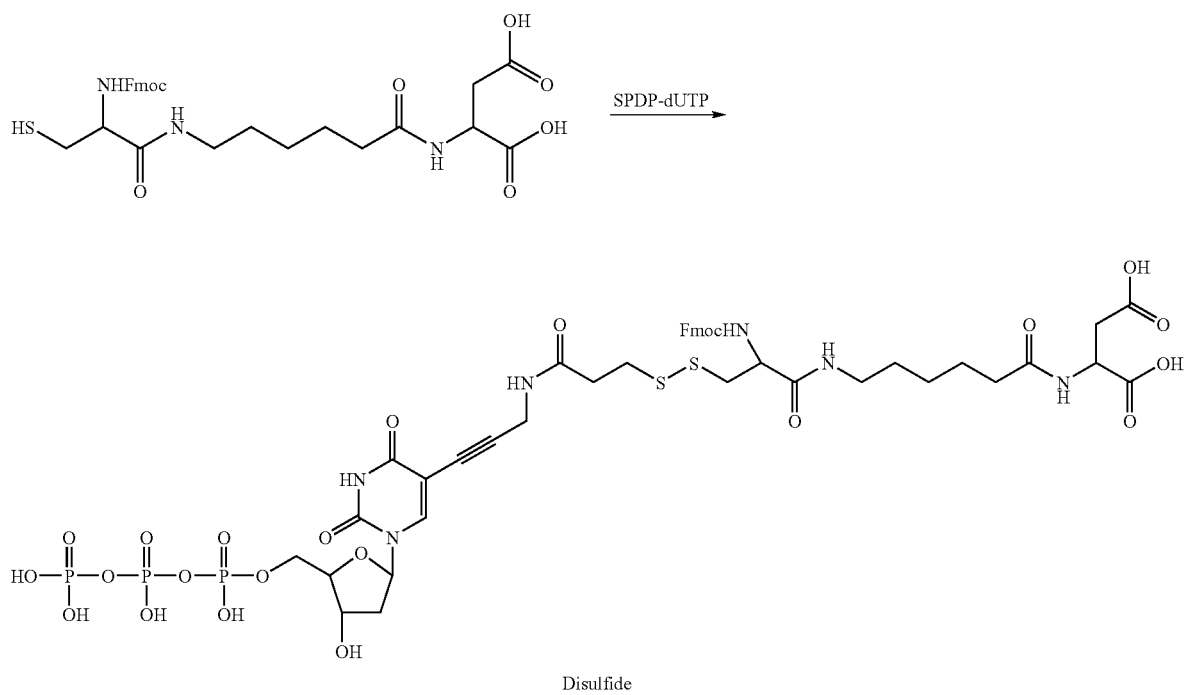

Disulfide

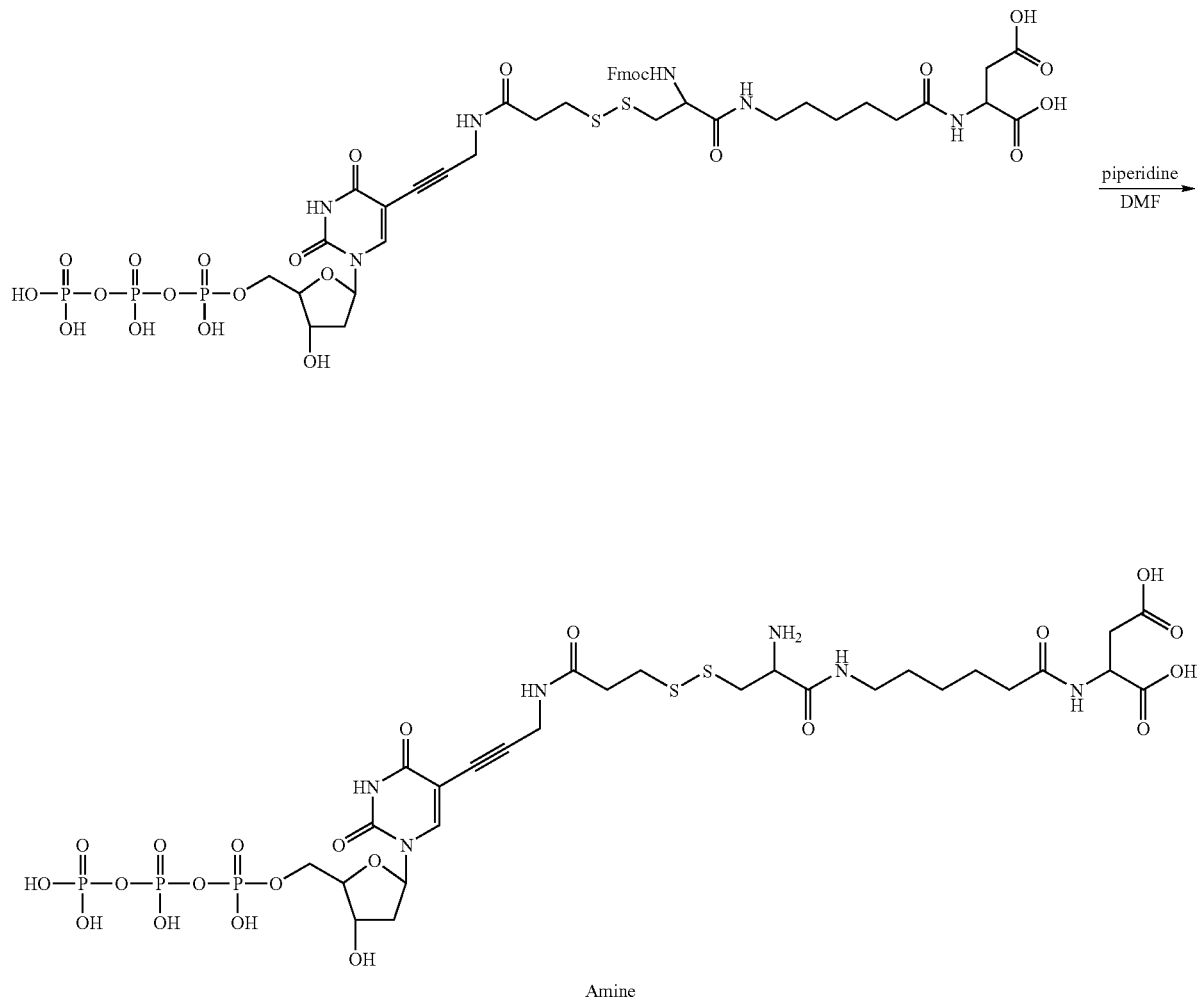

The starting carbamate (~1 µmol, 1 equiv) was treated with 20% piperidine in DMF (2 mL), and stirred at RT until the starting material was consumed based on LCMS analysis (about 15 min). After removing the solvent under reduced pressure, the reaction was HPLC purified (Waters Delta 600 pump and 2487 Dual λ Absorbance Detector, Phenomenex C18 preparative column, 250×10.0 mm 10 micron, gradient: 100% A for 3 min, then 1% B/min., buffer A 0.05M TEAB, buffer B $CH_3CN$, 5 mL/min. flow). Fractions containing the desired were pooled and lyophilized to yield the product as a white foam (0.19 µmol, 19%, $\epsilon_{289}$=13000).

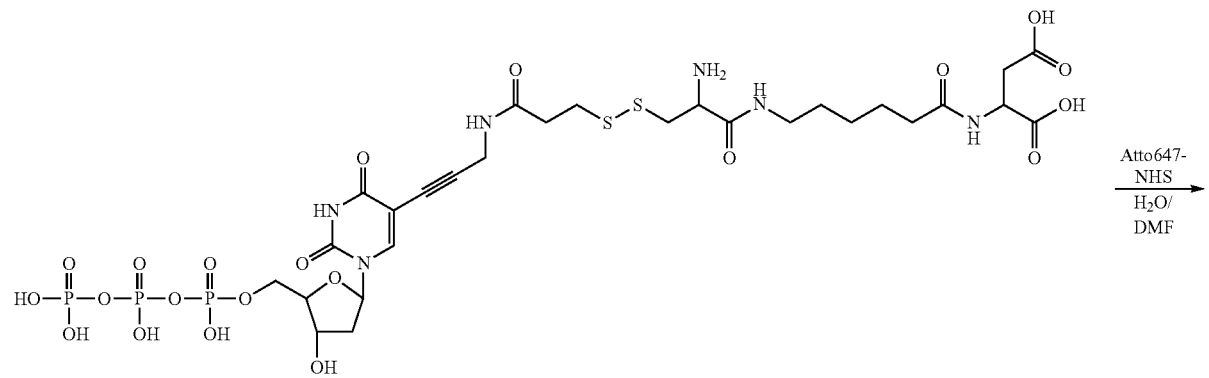

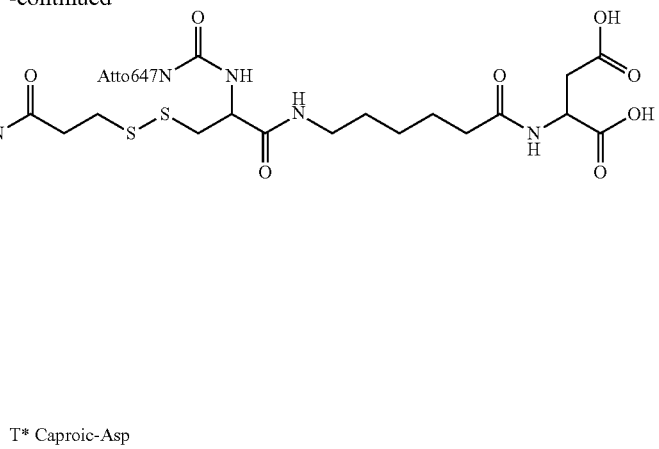

T* Caproic-Asp

Atto647N-NHS ester (0.010 mL, 0.68 μmol, 0.06M in anhydrous DMF, 3.6 eqv.) was added to a solution of amine (0.19 μmol, 1 eqv.) in H$_2$O (0.40 mL) in small aliquots. 1M K$_2$HPO$_4$ (0.40 mL) was also added to accelerate the reaction after there was little product formed within an hour. The reaction was monitored by LCMS to determine how much dye was needed to consume the starting amine. After disappearance of amine, the crude reaction was HPLC purified (Waters Delta 600 pump and 2487 Dual λ Absorbance Detector, Phenomenex C18 preparative column, 250×10.0 mm 10 micron, gradient: 100% A for 3 min., then 2% B/min., buffer A 0.05M TEAB, buffer B CH$_3$CN, 5 mL/min. flow). Fractions containing the desired were pooled and concentrated, then HPLC purified a second time under the same conditions, using CH$_3$OH instead of CH$_3$CN for buffer B. Fractions containing the desired were pooled and stored at −80° C. without removing the solvent (0.059 1μmol, 31%, $\epsilon_{645}$=150000).

Example 6

Caproic-Asp-Asp-Asp-Asp (Alternative Routes)

Synthetic Scheme V

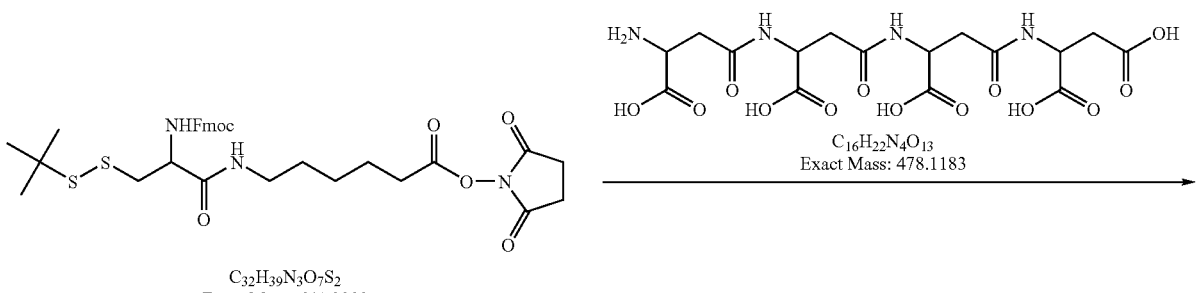

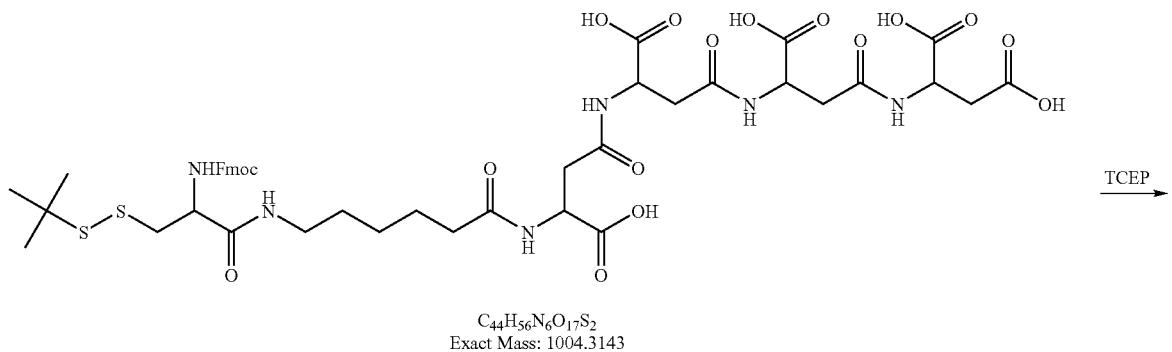

-continued
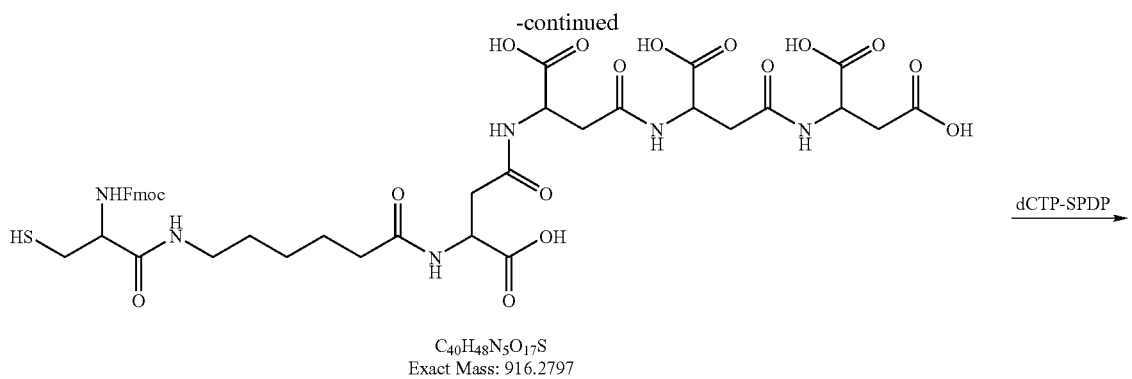
C₄₀H₄₈N₅O₁₇S
Exact Mass: 916.2797
→ dCTP-SPDP
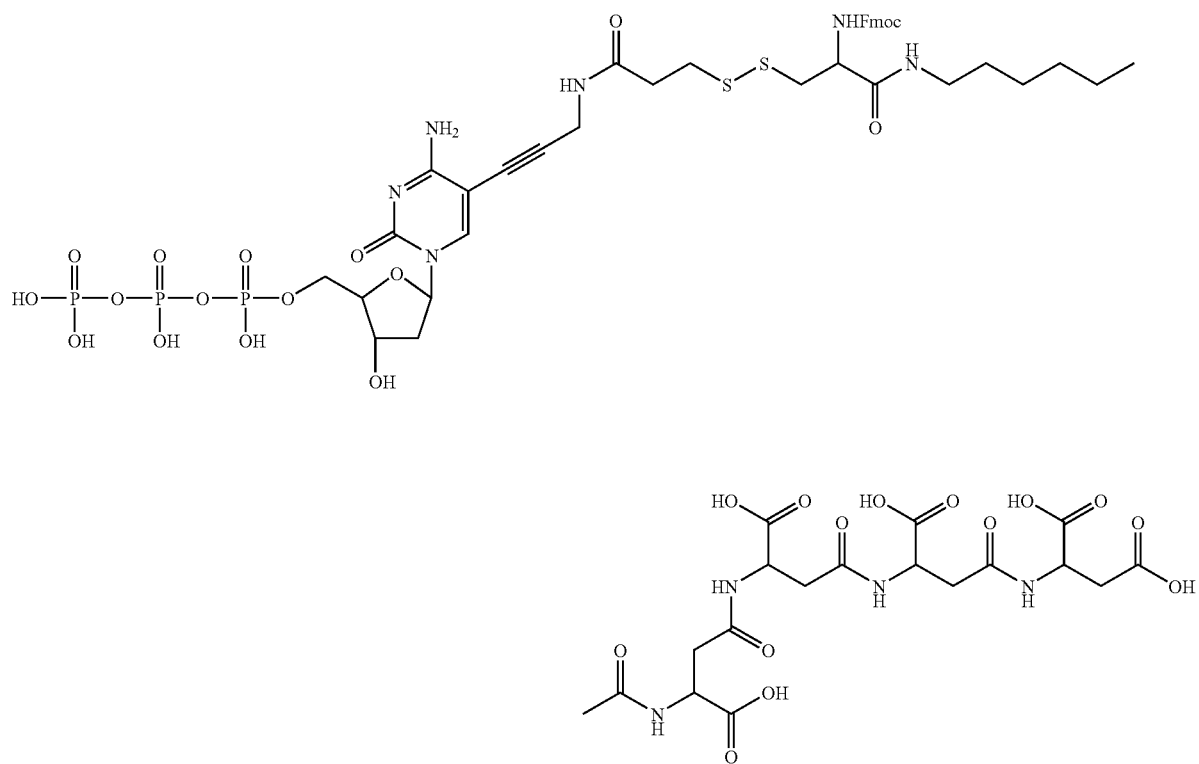
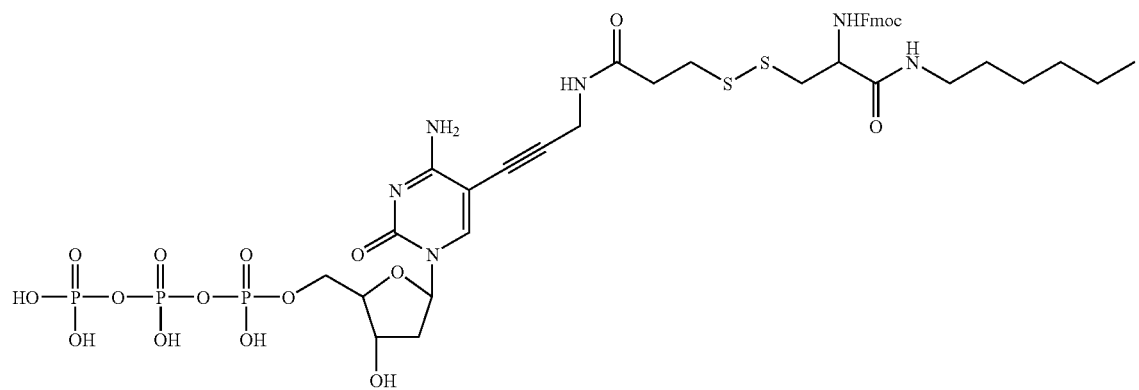

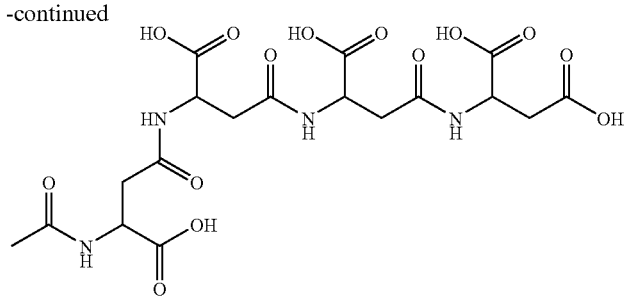
(i) Piperidine | (ii) Cy5-NHS or Atto-647N-NHS
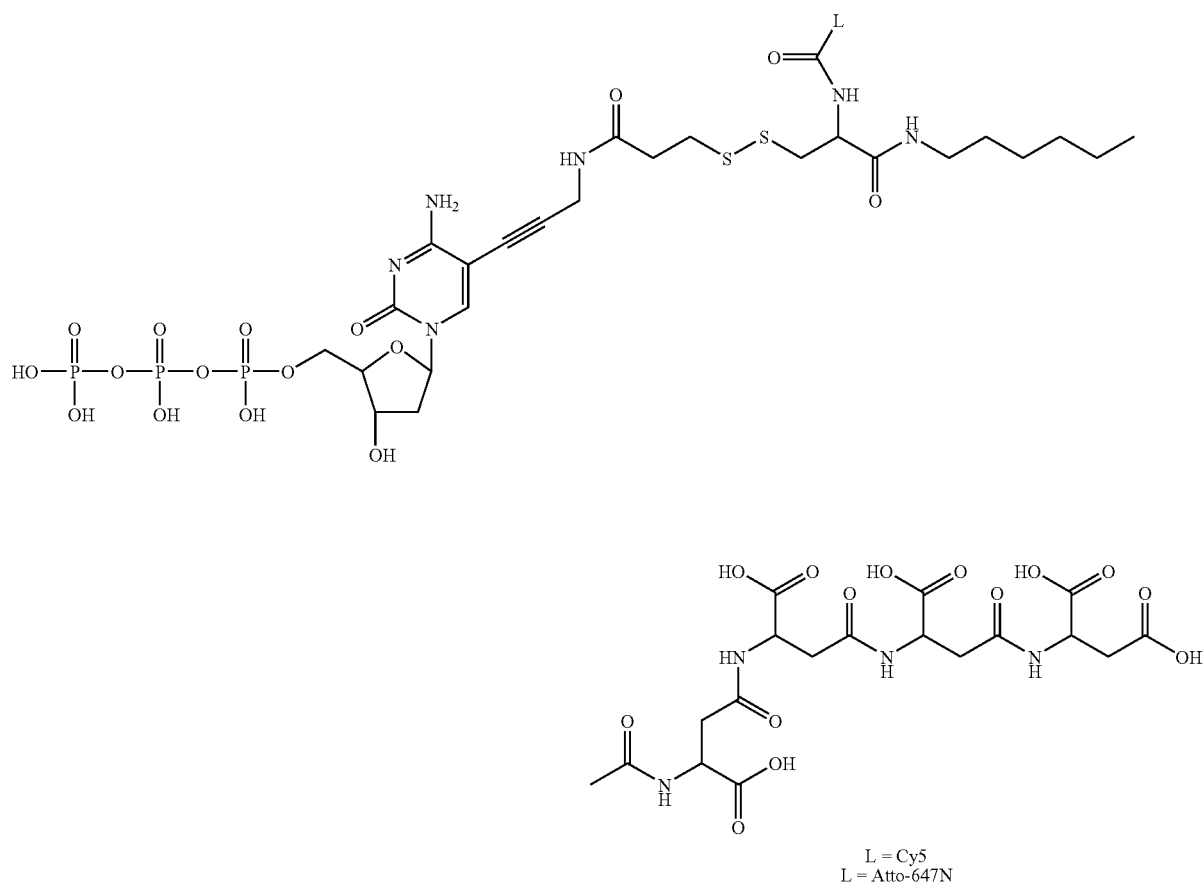
L = Cy5
L = Atto-647N
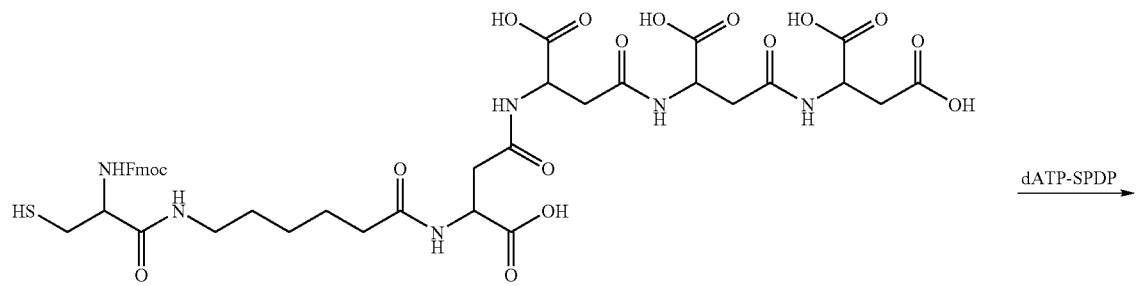
C$_{40}$H$_{48}$N$_6$O$_{17}$S
Exact Mass: 916.2797
dATP-SPDP 105 106
-continued
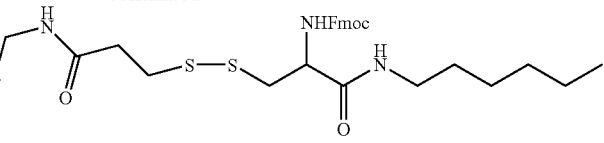
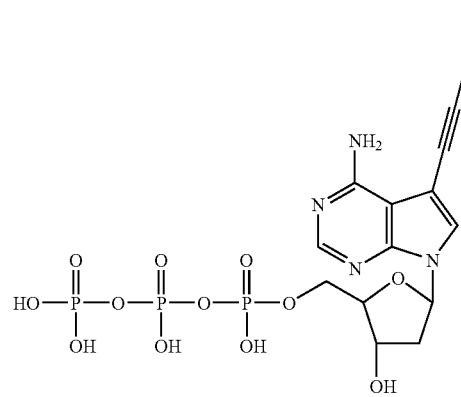
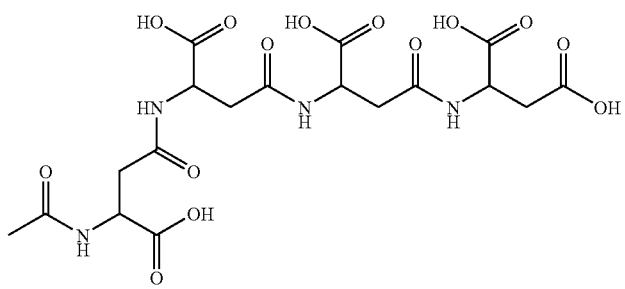
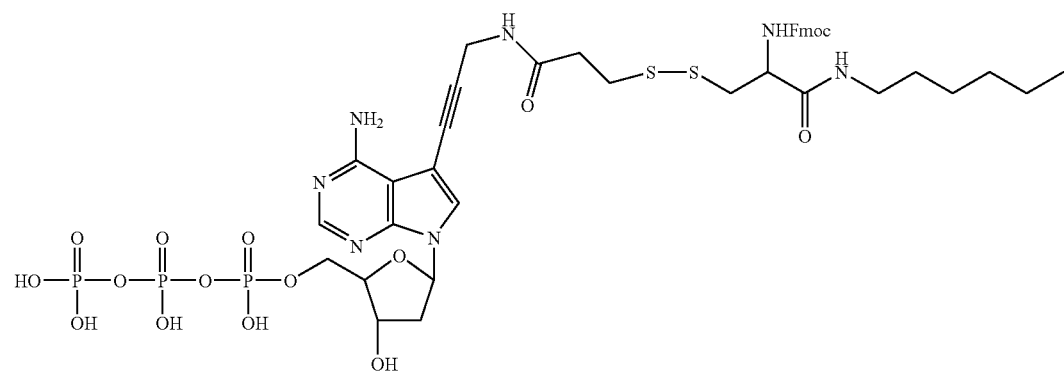
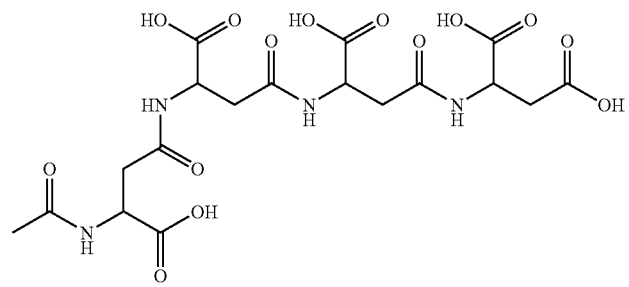
(i) Piperidine | (ii) Cy5-NHS or Atto-647N-NHS -continued
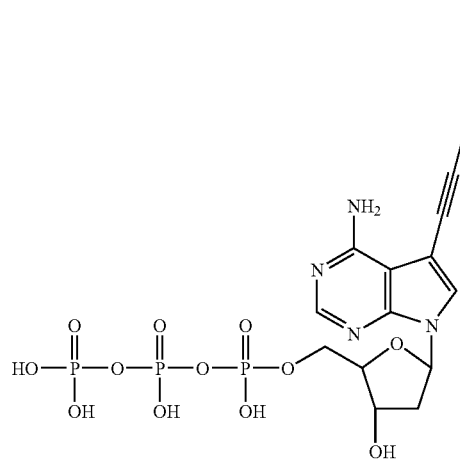
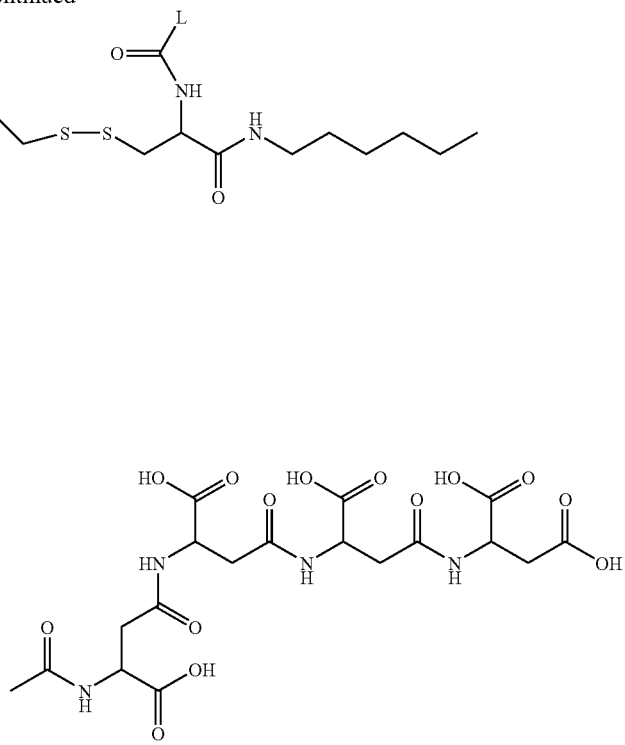
L = Cy5
L = Atto-647N
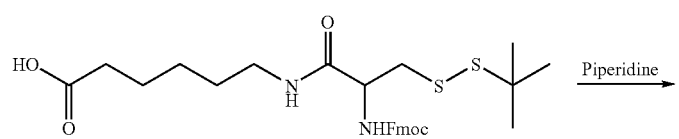
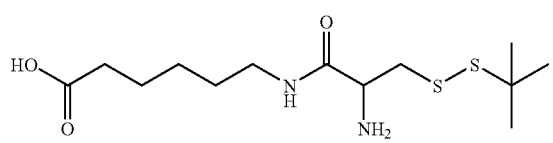
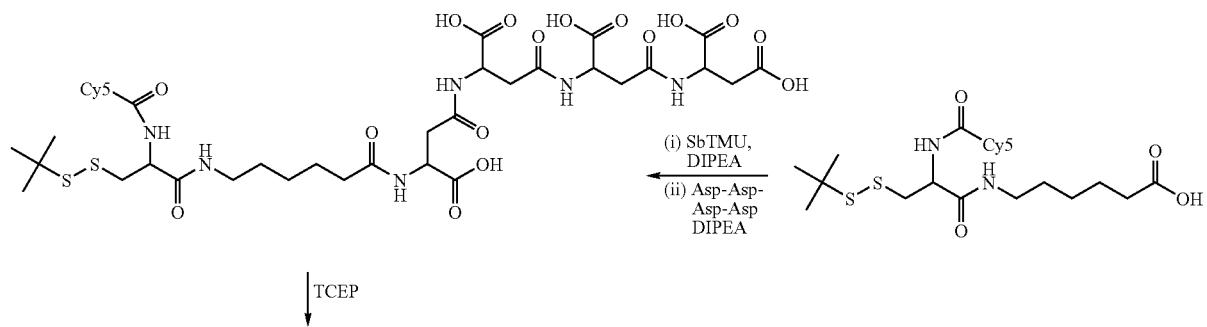

-continued
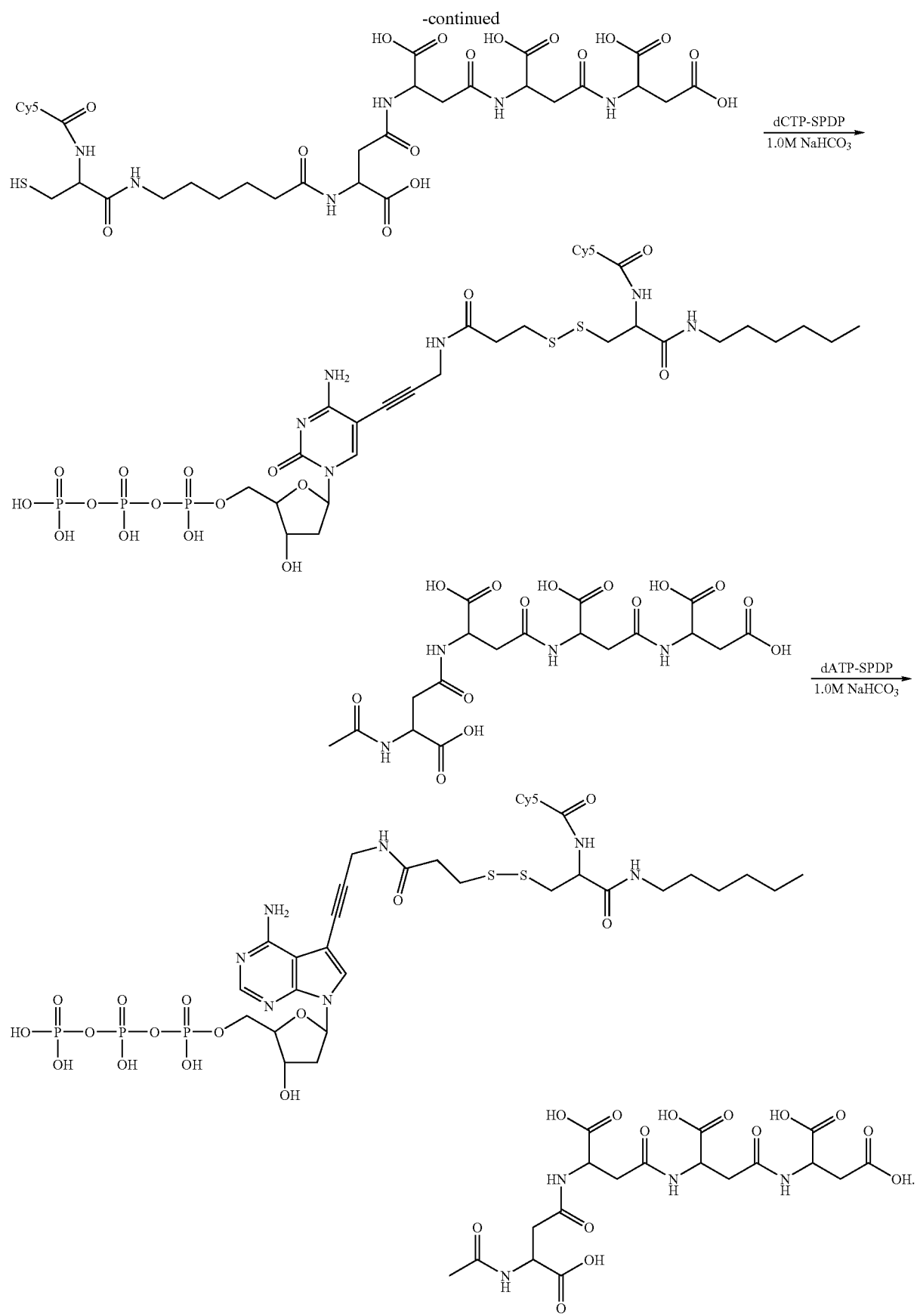

111 112
Example 7
G*Pro-Pro-Lys-Pro-Asp
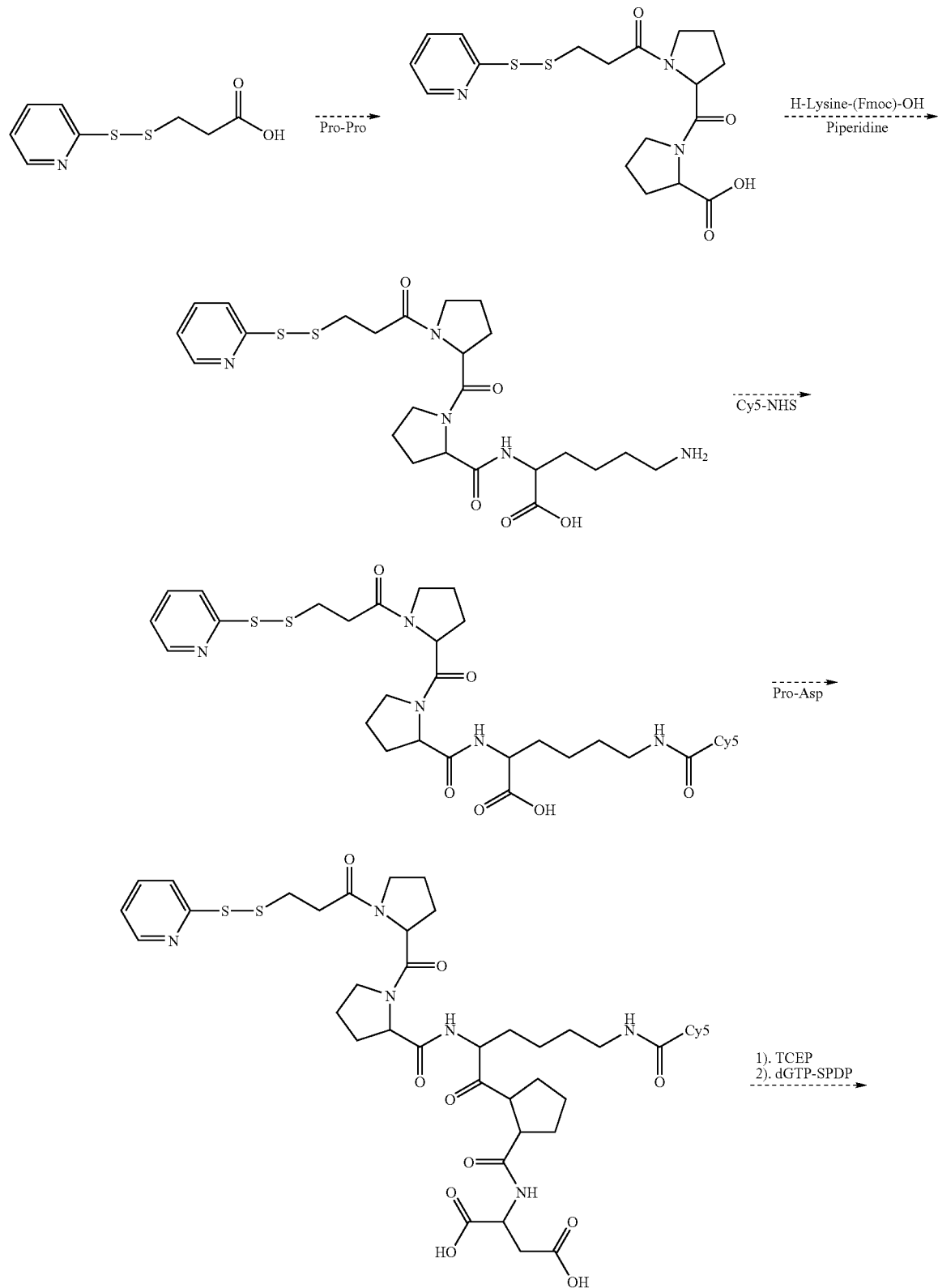
Synthetic Scheme VI

-continued

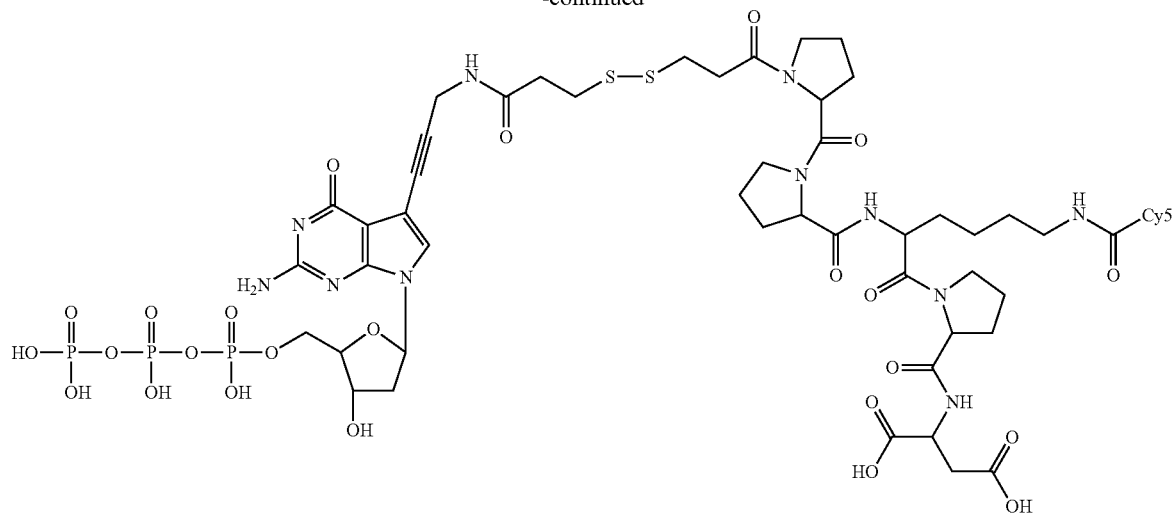

Example 8

Synthesis of Compounds in Table 1

Synthesis of dCTP and dATP Analogs:

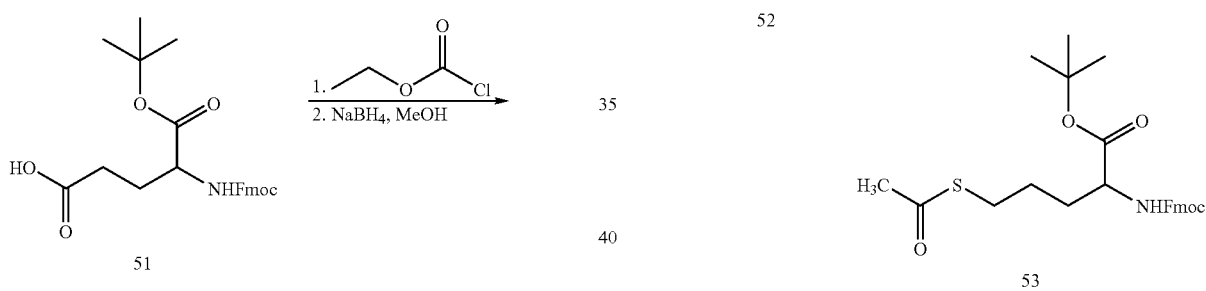

A solution of N-α-Fmoc-L-glutamic acid α-t-butyl ester (1.02 g, 2.35 mmol) in anhydrous THF (12 mL) was cooled to 0° C. Anhydrous NEt$_3$ (0.4 mL, 2.87 mmol) was added, followed by ethyl chloroformate (0.3 mL, 3.1 mmol). After stirring under Ar for ~10 min, sodium borohydride (0.27 g, 7.1 mmol) was added in one portion. Methanol (23 mL) was then added slowly over ~10 min, causing vigorous gas evolution. The reaction was warmed to RT, then acidified with 10% HCl (10 mL). The organics were removed in vacuo. The residue was diluted with EtOAc (40 mL), then washed with brine (2×50 mL). The organic phase was dried over Na$_2$SO$_4$, filtered, and concentrated under reduced pressure to yield alcohol 52 as a white foam (0.97 g, 99%).

A solution of alcohol 52 (0.97 g, 2.35 mmol) in anhydrous CH$_2$Cl$_2$ (9 mL) and anhydrous NEt$_3$ (0.7 mL, 5.0 mmol) was cooled to 0° C. Methanesulfonyl chloride (0.28 mL, 3.6 mmol) was added dropwise over ~15 min. After disappearance of starting material by TLC (~10 min), the reaction was washed with ice cold H$_2$O (2×25 mL), dried over Na$_2$SO$_4$, filtered, and concentrated under reduced pressure. Potassium thioacetate (0.54 g, 4.7 mmol) was added to a solution of the resultant white foam in acetone (6 mL), and the dark brown reaction was stirred at RT for 12 hrs. The crude reaction was then purified by flash column chromatography (5% to 20% EtOAc/hexanes) to afford thioacetate 53 as a brown oil (0.57 g, 52%).

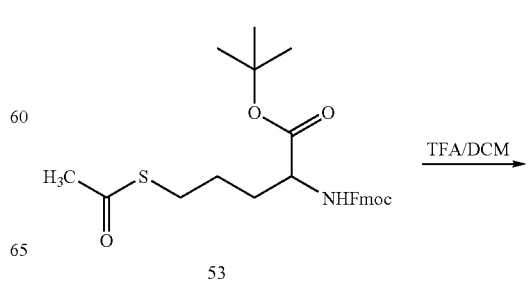

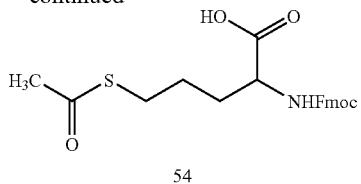

Trifluoroacetic acid (2 mL) was added to a solution of thioacetate 53 (0.29 g, 0.61 mmol) in CH$_2$Cl$_2$ (2 mL) and the reaction was stirred at RT for ~30 min. The reaction was diluted with CH$_2$Cl$_2$ (20 mL), then washed with brine (2×20 mL). The organic phase was dried over Na$_2$SO$_4$, filtered, and concentrated under reduced pressure to yield acid 54 as a brown oil (0.22 g, 88%).

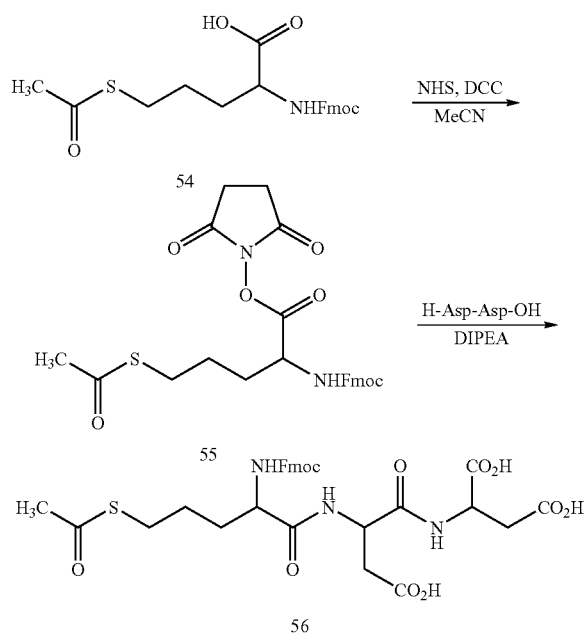

Acid 54 (0.22 g, 0.53 mmol) was dissolved in MeCN (3 mL). DCC (0.12 g, 0.58 mmol) was added, followed by NHS (0.07 g, 0.63 mmol) and the reaction was stirred at RT for an hour. White precipitate (DCU) began forming within five minutes. The reaction mixture was transferred to eppendorf tubes and centrifuged to remove the white precipitate. The dark brown supernatant containing NHS ester 55 was then added to a solution of H-Asp-Asp-OH (0.13 g, 0.52 mmol) in 0.25 M K$_2$HPO$_4$ (2.4 mL) and MeCN (1 mL). DIPEA (0.15 mL) was added to keep the pH ~8. The reaction was stirred at RT for two hours, then HPLC purified (Waters Delta 600 pump and 2487 Dual λ Absorbance Detector, Phenomenex C18 preparative column, 250×21.2 mm 10 micron, gradient: 100% A for 3 min, then 3% B/min, buffer A 0.1 M TEAB, buffer B MeCN, 10 mL/min flow). Fractions containing the desired thioacetate 56 were pooled and lyophilized to yield the product as a white foam (0.25 g, 75%).

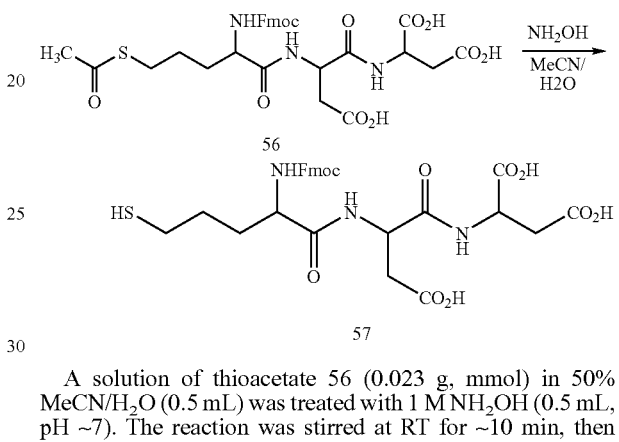

A solution of thioacetate 56 (0.023 g, mmol) in 50% MeCN/H$_2$O (0.5 mL) was treated with 1 M NH$_2$OH (0.5 mL, pH ~7). The reaction was stirred at RT for ~10 min, then immediately HPLC purified (Waters Delta 600 pump and 2487 Dual λ Absorbance Detector, Phenomenex C18 preparative column, 250×21.2 mm 10 micron, gradient: 100% A for 3 min, then 2% B/min, buffer A 0.1 M TEAB, buffer B MeCN, 10 mL/min flow). Fractions containing the desired thiol 57 were used immediately for subsequent reactions without quantifying.

Synthesis of dATP Analog:

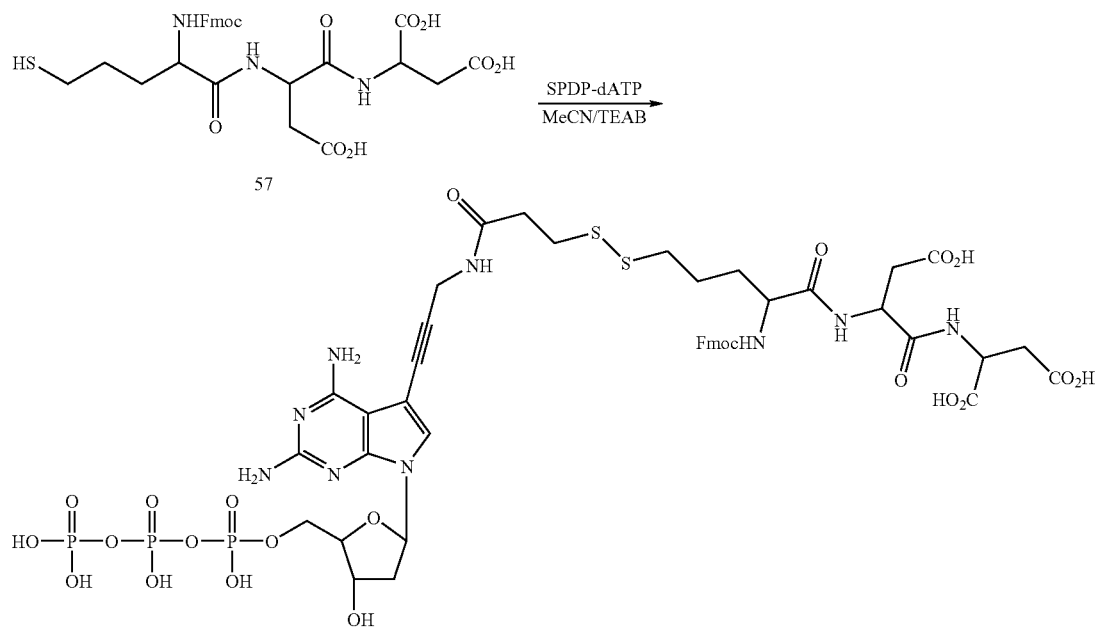

HPLC fractions containing thiol 57 (unquantified, 25 µmol) were mixed with HPLC fractions containing SPDP-dATP (20 mmol). After ~15 minutes the reaction was lyophilized, then HPLC purified (Waters Delta 600 pump and 2487 Dual λ Absorbance Detector, Phenomenex C18 preparative column, 250×21.2 mm 10 micron, gradient: 100% A for 3 min, then 1% B/min, buffer A 0.1 M TEAB, buffer B MeCN, 10 mL/min flow). Fractions containing the desired were pooled and lyophilized to yield 58, which was used for the subsequent reaction without quantifying.

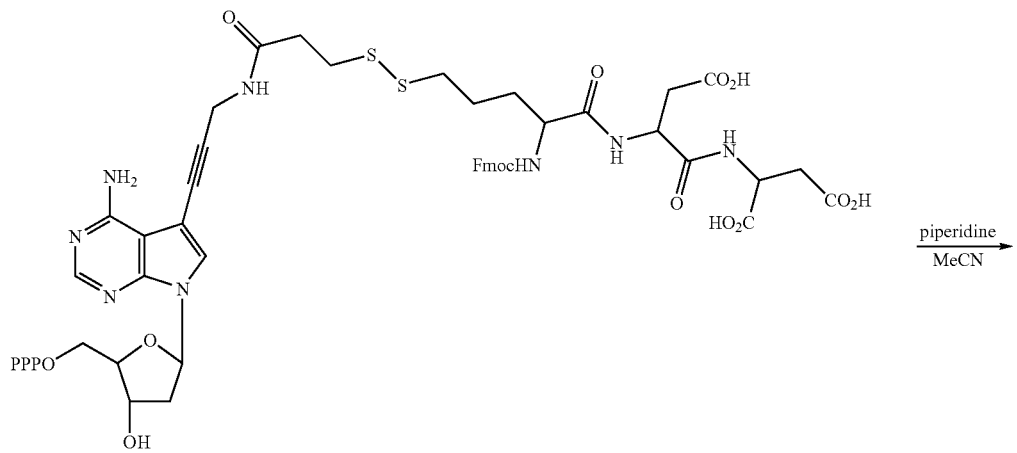

58

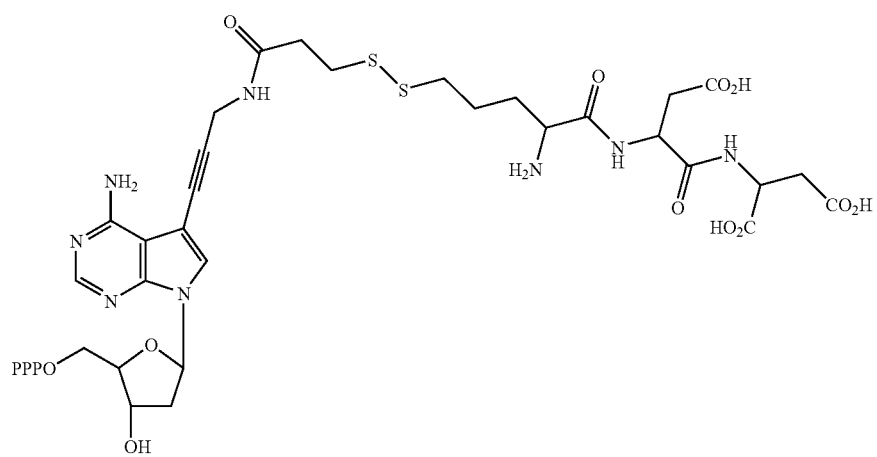

59

Carbamate 58 (unquantified, ~16 µmol) was treated with 20% piperidine/MeCN (2 mL) and 20% piperidine/DMF (1 mL) for 15 minutes to remove the Fmoc protecting group. The solvent was removed under reduced pressure, and the residue was then HPLC purified (Waters Delta 600 pump and 2487 Dual λ Absorbance Detector, Phenomenex C18 preparative column, 250×21.2 mm 10 micron, gradient: 100% A for 3 min, then 1% B/min, buffer A 0.1 M TEAB, buffer B MeCN, 10 mL/min flow). Fractions containing the desired were pooled and lyophilized to yield the product as a white foam (7.5 µmol, 47%, $\epsilon_{289}$=12700).

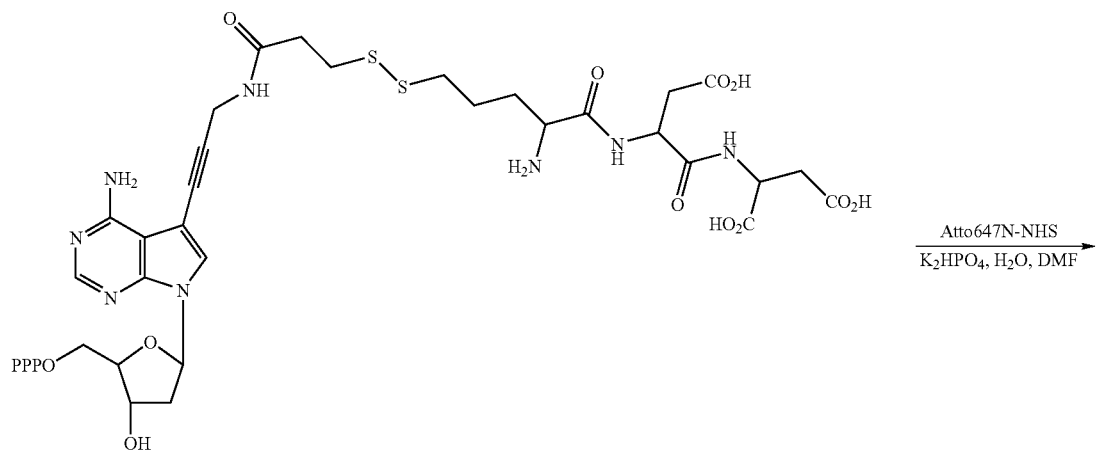

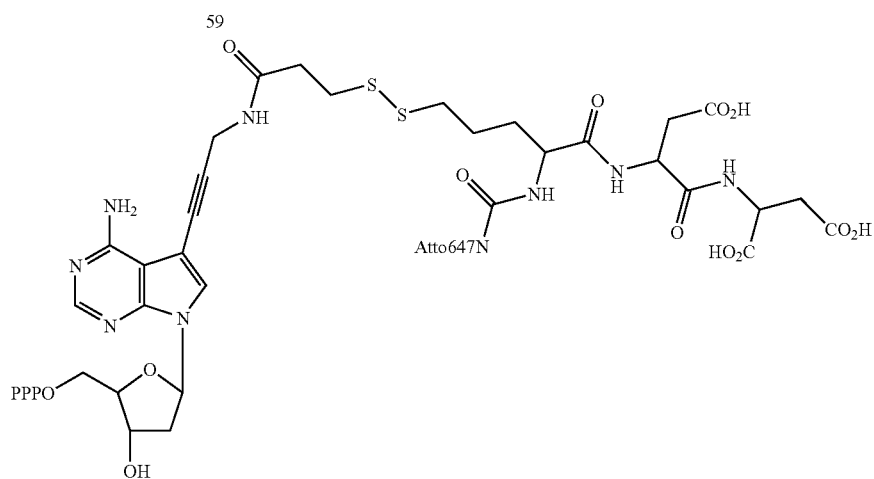

Atto647N NHS ester (0.36 mL, 36 μmol, 0.1 M in anhydrous DMF) was added to a solution of amine 59 (17.6 μmol) in H₂O (3 mL) and DMF (0.9 mL). After disappearance of amine by LCMS the crude reaction was HPLC purified (Waters Delta 600 pump and 2487 Dual λ Absorbance Detector, Phenomenex C18 preparative column, 250×15.00 mm 10 micron, gradient: 100% A for 3 min, then 1% B/min, buffer A 0.1 M TEAB, buffer B MeCN, 10 mL/min flow). Fractions containing the desired were pooled and lyophilized to yield amide 60 as a bright blue solid (13 μmol, 74%, $\epsilon_{649}$=150000).

Synthesis of dCTP Analog:

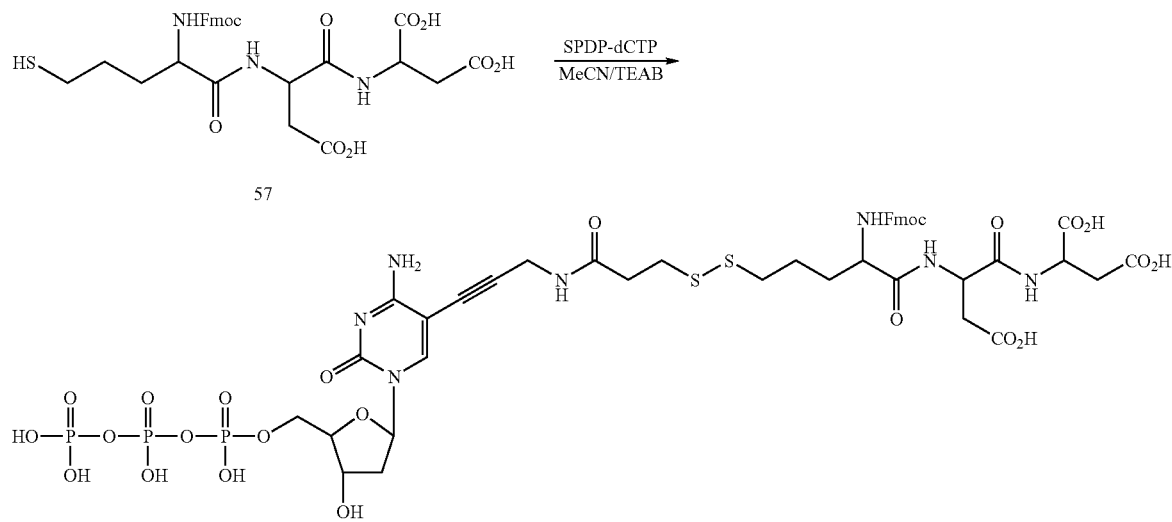

HPLC fractions containing thiol 57 (unquantified, ~55 µmol) were mixed with HPLC fractions containing SPDP-dCTP (45 µmol). After 30 minutes the reaction was lyophilized, then HPLC purified (Waters Delta 600 pump and 2487 Dual λ Absorbance Detector, Phenomenex C18 preparative column, 250×21.2 mm 10 micron, gradient: 100% A for 3 min, then 1% B/min, buffer A 0.1 M TEAB, buffer B MeCN, 10 mL/min flow). Fractions containing the desired were pooled and lyophilized to yield 61, which was used for the subsequent reaction without quantifying.

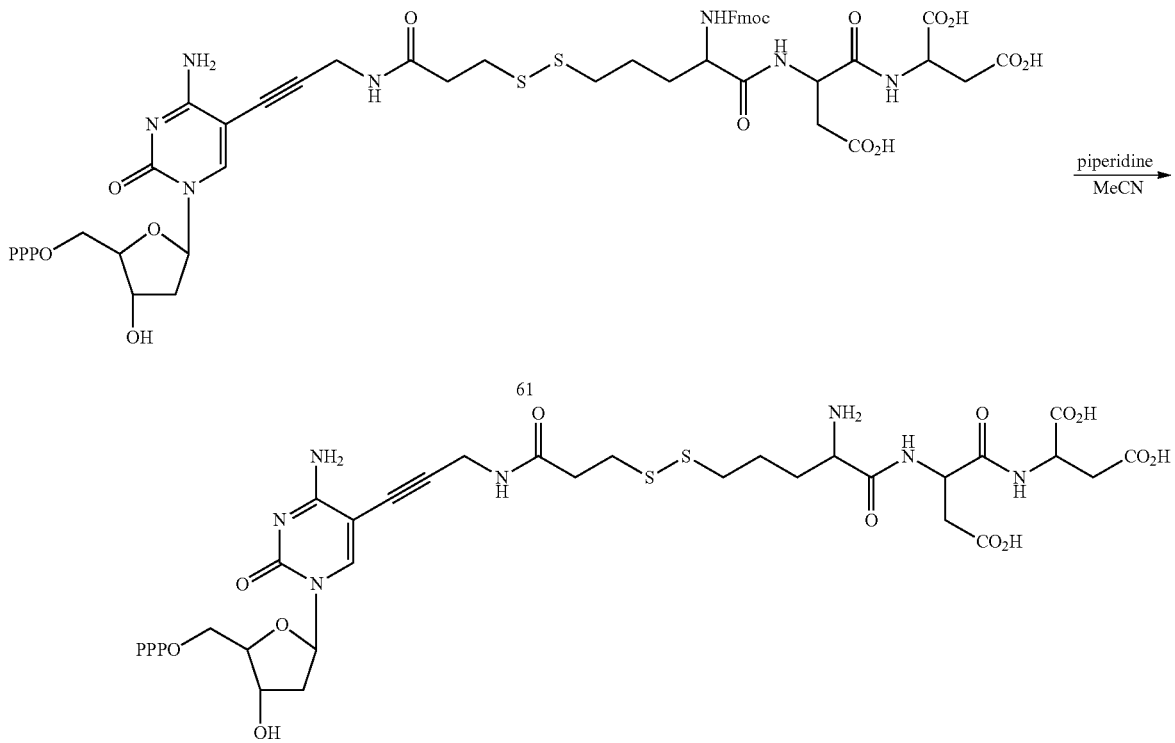

Carbamate 61 (unquantified, 36 µmol) was treated with 20% piperidine/MeCN (3 mL) for 15 minutes to remove the Fmoc protecting group. The solvent was removed under reduced pressure, and the residue was then HPLC purified (Waters Delta 600 pump and 2487 Dual λ Absorbance Detector, Phenomenex C18 preparative column, 250×21.2 mm 10 micron, gradient: 100% A for 3 min, then 1% B/min, buffer A 0.1 M TEAB, buffer B MeCN, 10 mL/min flow). Fractions containing the desired were pooled and lyophilized to yield amine 62 as a white foam (10.6 µmol, 29%, $\epsilon_{289}$=9300).

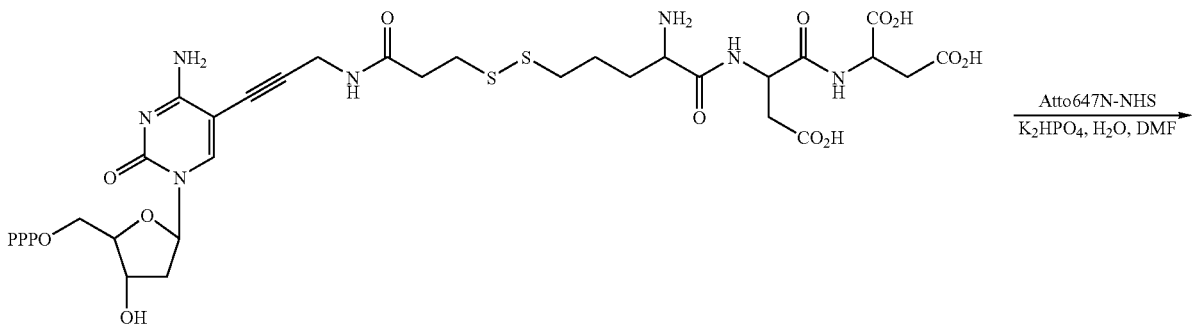

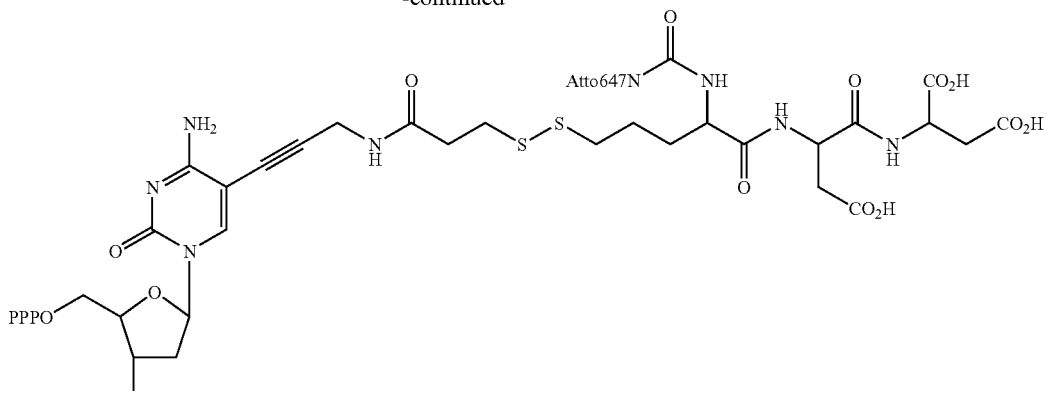

63

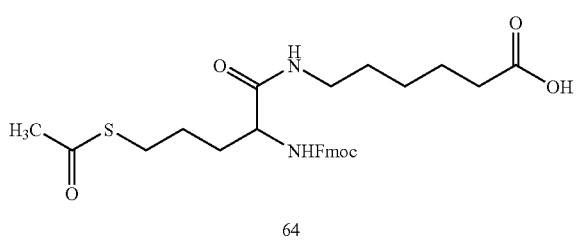

64

Atto647N NHS ester (0.475 mL, 47.5 μmol, 0.1 M in anhydrous DMF) was added to a solution of amine 62 (21 μmol) in H$_2$O (3 mL) and DMF (0.7 mL). After disappearance of amine by LCMS the crude reaction was HPLC purified (Waters Delta 600 pump and 2487 Dual λ Absorbance Detector, Phenomenex C18 preparative column, 250×15.00 mm 10 micron, gradient: 100% A for 3 min, then 1% B/min, buffer A 0.1 M TEAB, buffer B MeCN, 10 mL/min flow). Fractions containing the desired were pooled and lyophilized to yield amide 63 as a bright blue solid (17.7 μmol, 84%, ε$_{649}$=150000).

Synthesis of dUTP Analog:

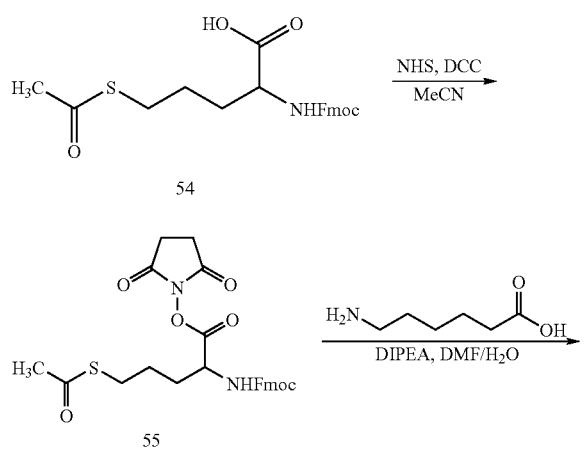

Acid 54 (0.14 g, 0.34 mmol) was dissolved in MeCN (0.6 mL). DCC (0.085 g, 0.41 mmol) was added, followed by NHS (0.051 g, 0.44 mmol) and the reaction was stirred at RT for an hour. White precipitate (DCU) began forming within five minutes. The reaction mixture was transferred to eppendorf tubes and centrifuged to remove the white precipitate. The supernatant containing NHS ester 55 was then added to a solution of 6-aminocaproic acid (0.049 g, 0.37 mmol) in H$_2$O (0.4 mL) and DMF (0.4 mL). DIPEA (0.05 mL) was added to keep the pH ~8. The reaction was stirred at RT for 12 hours, then adjusted to pH 4 with 0.1 M HCl and extracted with CH$_2$Cl$_2$ (2×25 mL). The organic phase was dried over Na$_2$SO$_4$, filtered, and concentrated under reduced pressure. Purification by flash column chromatography (100% CH$_2$Cl$_2$ to 5% MeOH/CH$_2$Cl$_2$) afforded acid 64 (0.12 g, 69%).

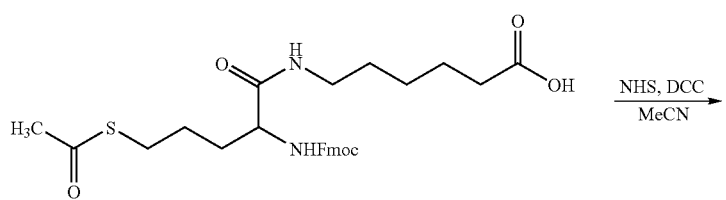

64

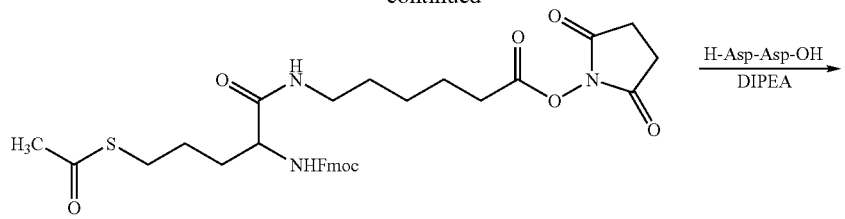

65

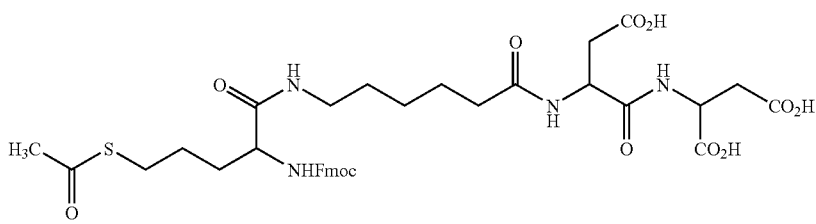

66

Acid 64 (0.12 g, 0.23 mmol) was dissolved in MeCN (0.6 mL). DCC (0.058 g, 0.28 mmol) was added, followed by NHS (0.035 g, 0.3 mmol) and the reaction was stirred at RT for an hour. White precipitate (DCU) began forming within twenty minutes. The reaction mixture was transferred to eppendorf tubes and centrifuged to remove the white precipitate. The supernatant containing NHS ester 65 was then added to a solution of H-Asp-Asp-OH (0.075 g, 0.30 mmol) in 0.1 M $K_2HPO_4$ (0.5 mL) and MeCN (0.5 mL). DIPEA (0.095 mL) was added to keep the pH ~8. The reaction was stirred at RT for 12 hours, then HPLC purified (Waters Delta 600 pump and 2487 Dual λ Absorbance Detector, Phenomenex C18 preparative column, 250×21.2 mm 10 micron, gradient: 100% A for 5 min, then 2% B/min, buffer A 0.1 M TEAB, buffer B MeCN, 10 mL/min flow). Fractions containing the desired thioacetate 66 were pooled and lyophilized to yield the product as a white foam (0.1 g, 55%).

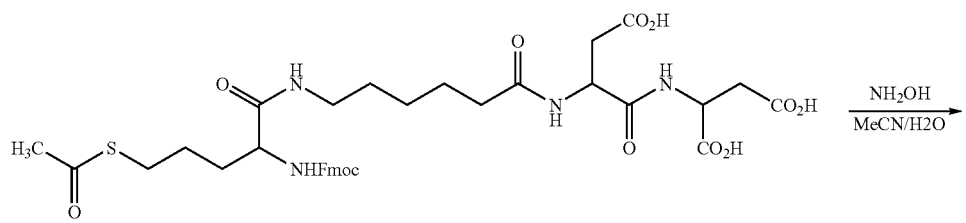

66

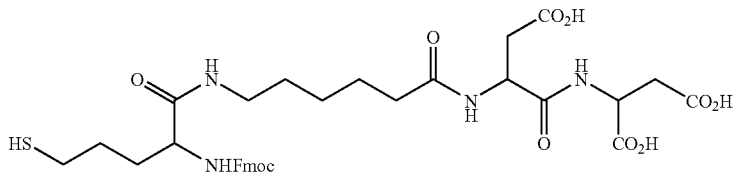

67

A solution of thioacetate 66 (0.1 g, 0.13 mmol) in 50% MeCN/$H_2O$ (2 mL) was treated with 1 M $NH_2OH$ (2 mL, pH ~7). The reaction was stirred at RT for ~10 min, then immediately HPLC purified (Waters Delta 600 pump and 2487 Dual λ Absorbance Detector, Phenomenex C18 preparative column, 250×21.2 mm 10 micron, gradient: 100% A for 5 min, then 2% B/min, buffer A 0.1 M TEAB, buffer B MeCN, 10 mL/min flow). Fractions containing the desired thiol 67 were used immediately for subsequent reactions without quantifying.

Synthesis of dUTP Analog:

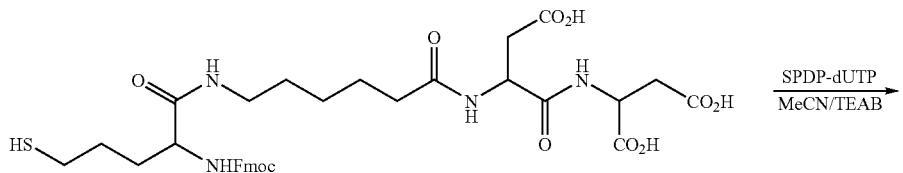

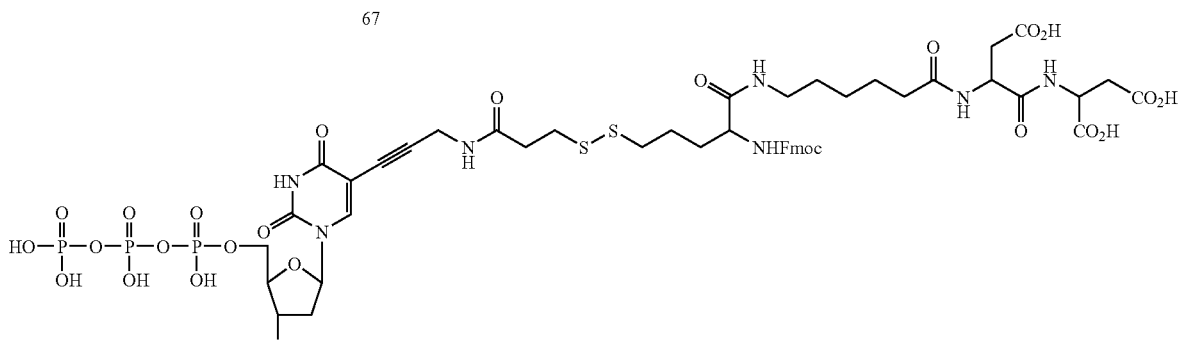

HPLC fractions containing thiol 67 (unquantified, 55 µmol) were mixed with HPLC fractions containing SPDP-dUTP (50 µmol). After ~1 hr the reaction was concentrated to remove MeCN, then HPLC purified (Waters Delta 600 pump and 2487 Dual λ Absorbance Detector, Phenomenex C18 preparative column, 250×21.2 mm 10 micron, gradient: 100% A for 5 min, then 2% B/min, buffer A 0.1 M TEAB, buffer B MeCN, 10 mL/min flow). Fractions containing the desired were pooled and lyophilized to yield 68, which was used for the subsequent reaction without quantifying.

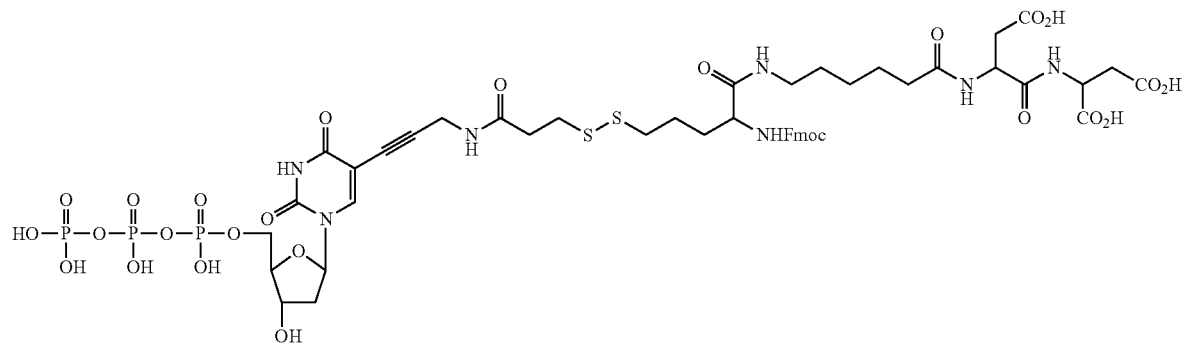

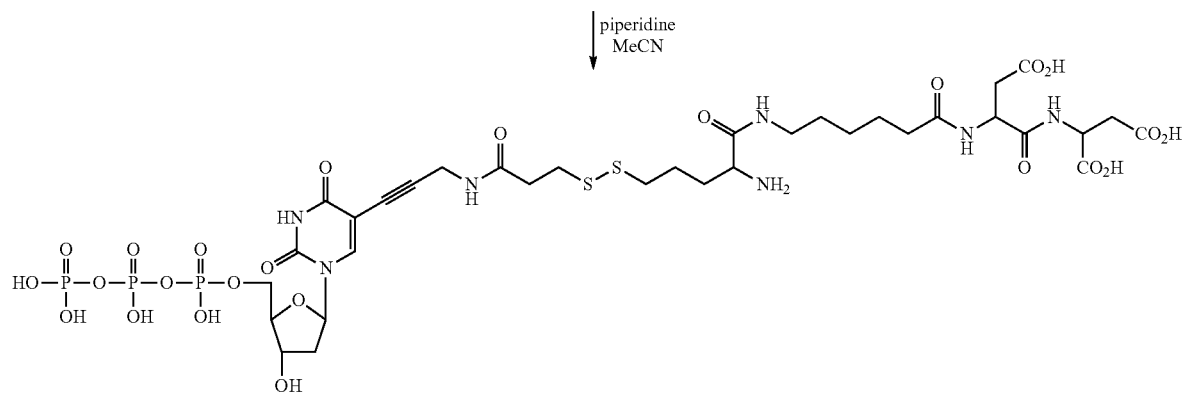

Carbamate 68 (unquantified, ~50 μmol) was treated with 20% piperidine/MeCN (2 mL) for 30 minutes to remove the Fmoc protecting group. The solvent was removed under reduced pressure, and the residue was dissolved in 50 mM TEAB buffer (~3 mL), causing formation of copious white precipitate (dibenzylfulvene). The mixture was transferred to eppendorf tubes and centrifuged to remove the precipitate. The supernatant was then HPLC purified (Waters Delta 600 pump and 2487 Dual λ Absorbance Detector, Phenomenex C18 preparative column, 250×21.2 mm 10 micron, gradient: 100% A for 5 min, then 2% B/min, buffer A 0.1 M TEAB, buffer B MeCN, 10 mL/min flow). Fractions containing the desired were pooled and lyophilized to yield amine 69 as a white foam (39 μmol, 78%, $\epsilon_{288}$=13000).

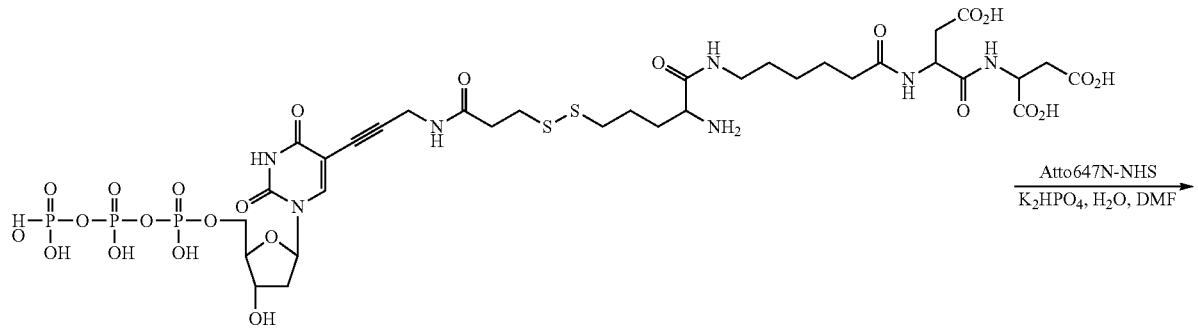

69

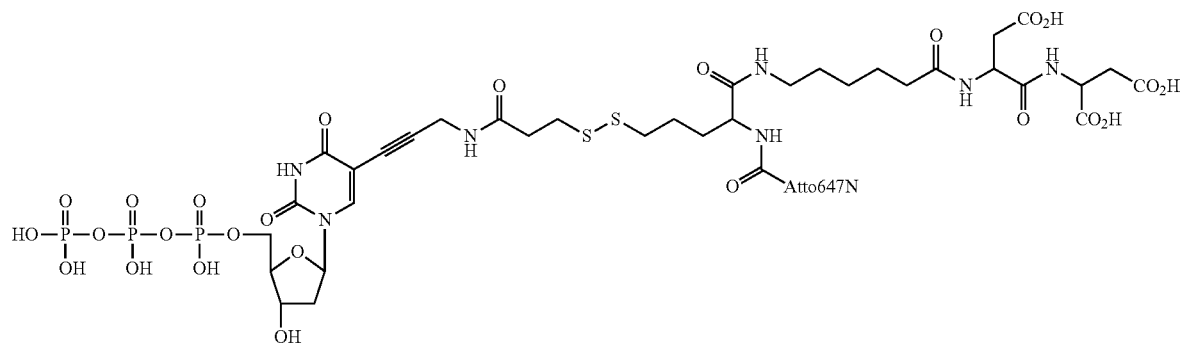

70

Atto647N NHS ester (0.24 mL, 24 μmol, 0.1 M in anhydrous DMF) was added to a solution of amine 69 (20 μmol) in $H_2O$ (0.5 mL) and DMF (0.1 mL). DIPEA (4 mL, 20 μmol) was added to basify the reaction. After disappearance of amine by LCMS the crude reaction was HPLC purified (Waters Delta 600 pump and 2487 Dual λ Absorbance Detector, Phenomenex C18 preparative column, 250×15.00 mm 10 micron, gradient: 100% A for 5 min, then 1% B/min, buffer A 0.1 M TEAB, buffer B MeCN, 10 mL/min flow). Fractions containing the desired were pooled and lyophilized to yield amide 70 as a bright blue solid (20 μmol, 99%, $\epsilon_{649}$=150000).

Syntheses of dGTP Analog

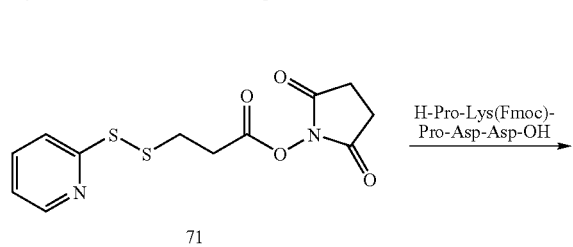

71

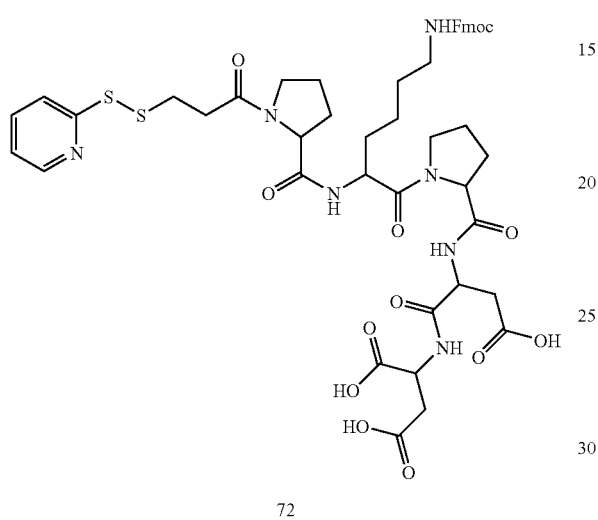

72

SPDP (2.1 mL, 0.10 mmol, 0.05 M in DMF) was added to a solution of H-Pro-Lys(Fmoc)-Pro-Asp-Asp-OH (0.054 g, 0.068 mmol) in 0.1 M $K_2HPO_4$ (3 mL) and the reaction was stirred at RT until disappearance of the peptide by LCMS. The crude reaction was HPLC purified (Waters Delta 600 pump and 2487 Dual λ Absorbance Detector, Phenomenex C18 preparative column, 250×21.2 mm 10 micron, gradient: 100% A for 3 min, then 2% B/min, buffer A 0.1 M TEAB, buffer B MeCN, 10 mL/min flow). Fractions containing the desired were pooled and lyophilized to yield peptide 72, which was used without quantifying.

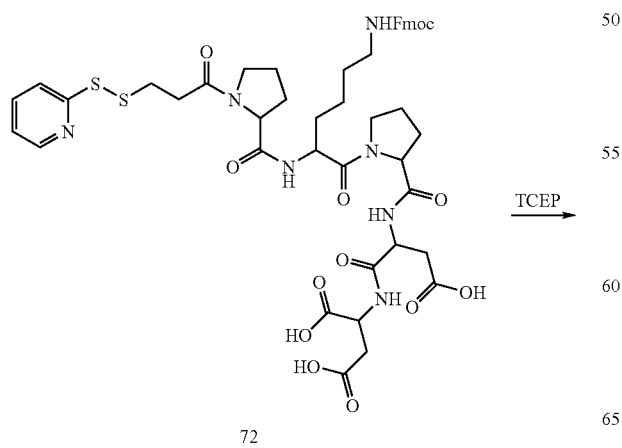

72

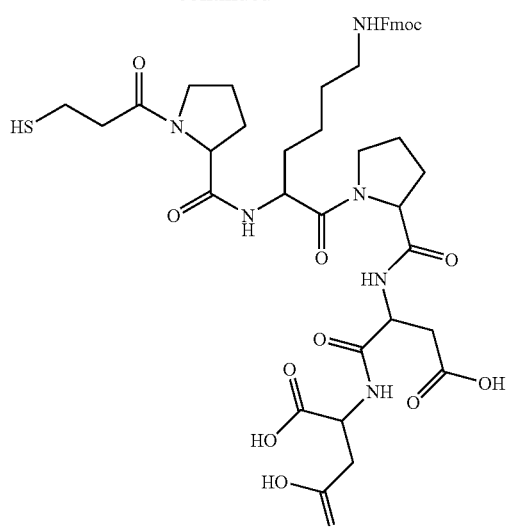

73

A solution of disulfide 72 (~60 μmol) in $H_2O$ (5 mL) was treated with TCEP (1.44 mL, 0.72 mmol, 0.5 M in $H_2O$). After ~15 minutes the crude reaction was HPLC purified (Waters Delta 600 pump and 2487 Dual λ Absorbance Detector, Phenomenex C18 preparative column, 250×21.2 mm 10 micron, gradient: 100% A for 3 min, then 2% B/min, buffer A 0.1 M TEAB, buffer B MeCN, 10 mL/min flow). Fractions containing the desired thiol 73 were used immediately for the subsequent reaction without concentrating or quantifying.

Synthesis of dGTP Analog:

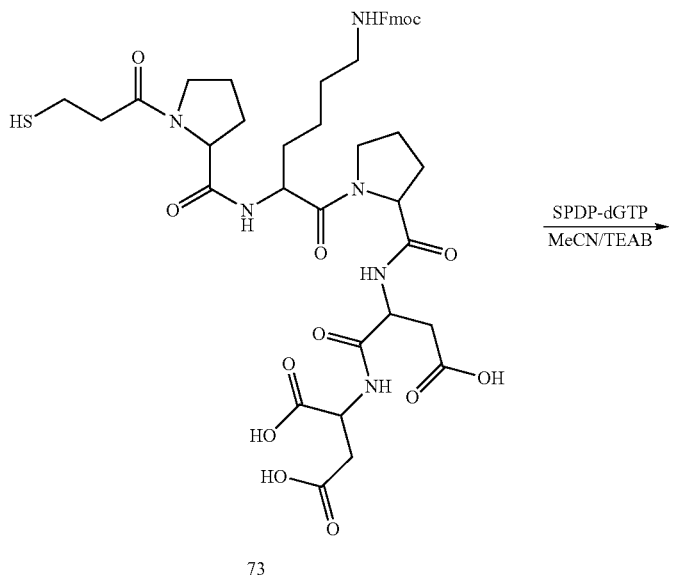

73

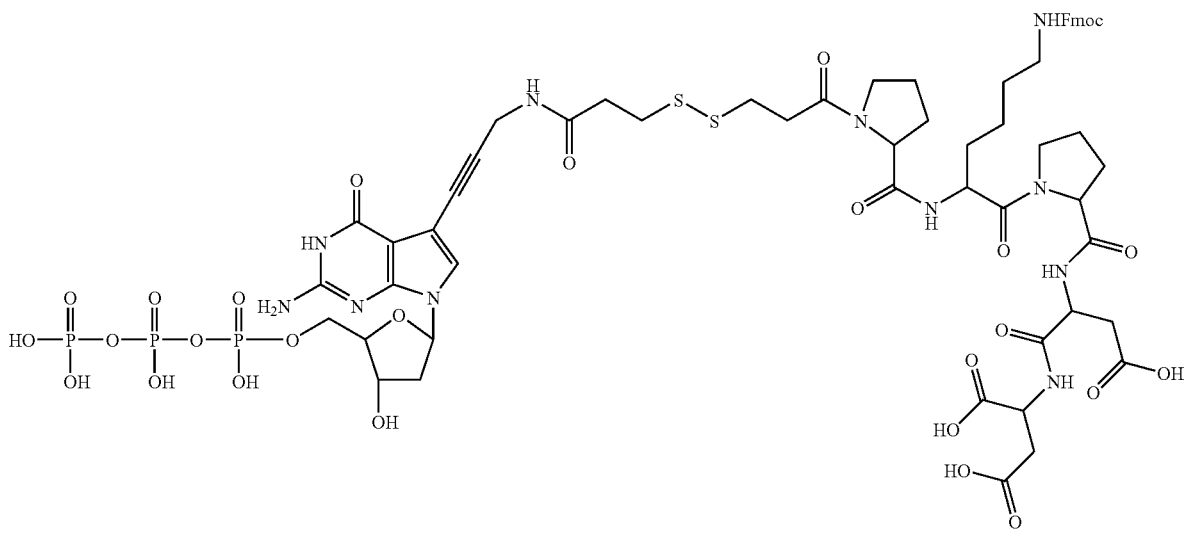

74

HPLC fractions containing thiol 73 (unquantified, 50 mmol) were mixed with HPLC fractions containing SPDP-dGTP (58 µmol). After ~30 minutes the reaction was concentrated to remove MeCN, then HPLC purified (Waters Delta 600 pump and 2487 Dual λ Absorbance Detector, Phenomenex C18 preparative column, 250×21.2 mm 10 micron, gradient: 100% A for 3 min, then 1% B/min, buffer A 0.1 M TEAB, buffer B MeCN, 10 mL/min flow). Fractions containing the desired were pooled and lyophilized to yield 74, which was used for the subsequent reaction without quantifying.

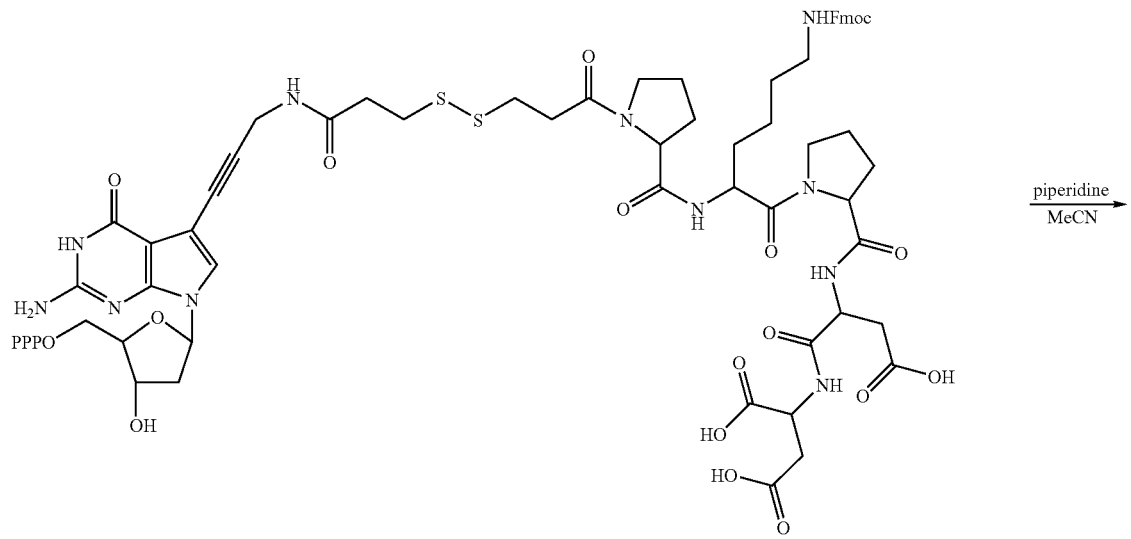

74

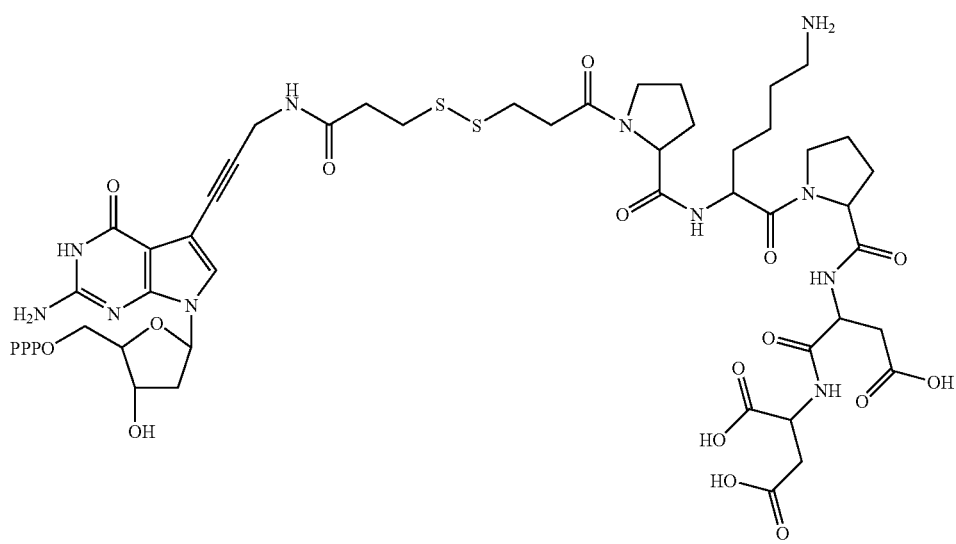

75

Carbamate 74 (unquantified, ~40 μmol) was treated with 20% piperidine/MeCN (4 mL) for 15 minutes to remove the Fmoc protecting group. The solvent was removed under reduced pressure, and the residue was then HPLC purified (Waters Delta 600 pump and 2487 Dual λ Absorbance Detector, Phenomenex C18 preparative column, 250×21.2 mm 10 micron, gradient: 100% A for 3 min, then 1% B/min, buffer A 0.1 M TEAB, buffer B MeCN, 10 mL/min flow). Fractions containing the desired were pooled and lyophilized to yield the product as a white foam (19.1 μmol, 48%, $\epsilon_{289}$=11900).

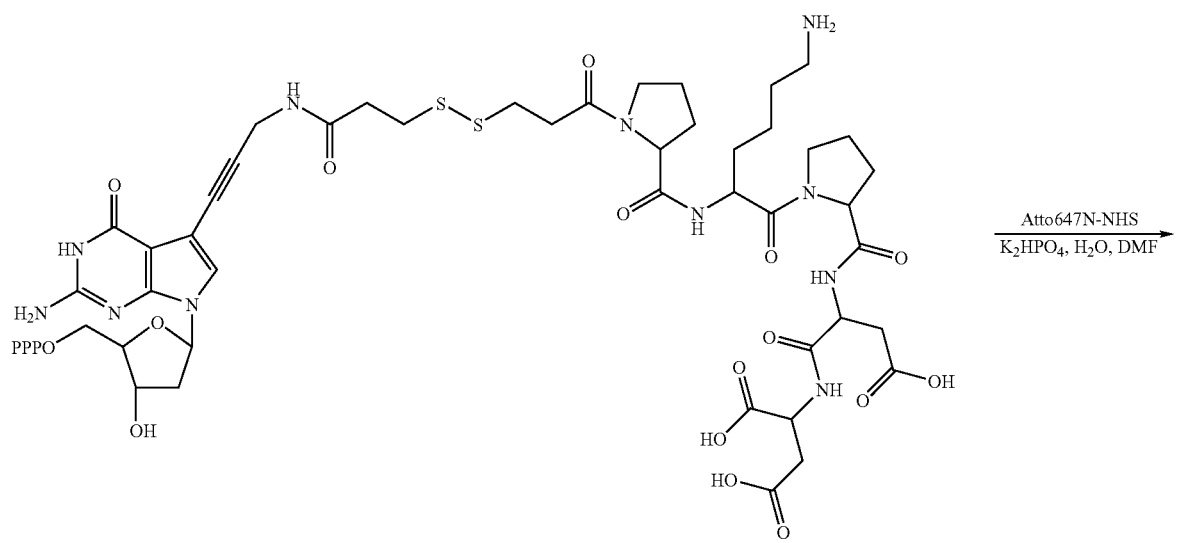

75

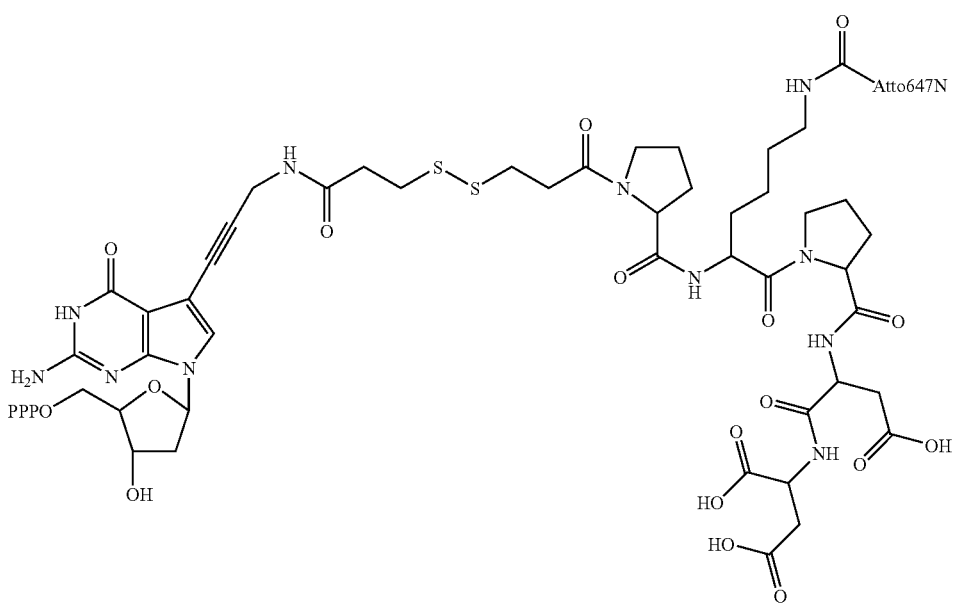

76

Atto647N NHS ester (0.30 mL, 30 μmol, 0.1 M in anhydrous DMF) was added to a solution of amine 75 (19.1 μmol) in H$_2$O (3 mL) and DMF (0.6 mL). After disappearance of amine by LCMS the crude reaction was HPLC purified (Waters Delta 600 pump and 2487 Dual λ Absorbance Detector, Phenomenex C18 preparative column, 250×15.00 mm 10 micron, gradient: 100% A for 3 min, then 1% B/min, buffer A 0.1 M TEAB, buffer B MeCN, 10 mL/min flow). Fractions containing the desired were pooled and lyophilized to yield amide 76 as a bright blue solid (19 μmol, 99%, $\epsilon_{649}$=150000).

The schemes above and variations thereof may be utilized for syntheses of derivatives and analogs of the exemplary nucleotide analogs shown above, for example, those having additional amino groups at the Inhibitor end and/or compounds of different linking groups.

While specific embodiments of the subject invention have been discussed, the above specification is illustrative and not restrictive. Many variations of the invention will become apparent to those skilled in the art upon review of this specification. Contemplated equivalents of the nucleotide analogs disclosed here include compounds which otherwise correspond thereto, and which have the same general properties thereof, wherein one or more simple variations of substituents or components are made which do not adversely affect the characteristics of the nucleotide analogs of interest. In general, the components of the nucleotide analogs disclosed herein may be prepared by the methods illustrated in the general reaction schema as described herein or by modifications thereof, using readily available starting materials, reagents, and conventional synthesis procedures.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

INCORPORATION BY REFERENCE

The entire disclosure of each of the publications and patent documents referred to herein is incorporated by reference in its entirety for all purposes to the same extent as if each individual publication or patent document were so individually denoted.

We claim:

1. A nucleotide analog of the following Formula II:

$$\text{NTP-}R_1 - R_2 - R_3\text{-Inhibitor}$$
$$\overset{|}{R_4}$$
$$\overset{|}{L}$$

wherein
- NTP is a nucleoside or nucleotide triphosphate, or an analog thereof, capable of incorporating onto the 3' end of a polynucleotide strand hybridized to a template presenting the complement of the NTP;
- L is a detectable label that facilitates the identification of the nucleotide analog;
- Inhibitor comprises (a) one or more multiply charged groups or groups capable of becoming multiply charged, or (b) two or more singly charged groups or two or more groups capable of becoming singly charged;
- $R_1$ comprises a cleavable bond, which upon cleavage results in de-association of NTP from both L and Inhibitor;
- $R_2$ is a tri-valent radical having the formula:

$$-(R_2''-R_2')-$$

wherein
- $R_2'$ is a tri-valent radical, and
- $R_2''$ is a bi-valent radical selected from:

—(CH$_2$)$_x$—, —(CH$_2$—O)$_x$—, —(CH$_2$—O)$_z$—(CH$_2$)$_y$—, —(CH$_2$)$_z$—(CH$_2$—O)$_y$—, and the same substituted with one or more groups selected from hydroxyl, halogen, amino, thiol, (C$_1$-C$_6$) alkyl, wherein x, y and z are each integers with x and y+z are each from 2 to 10;
- $R_3$ is a bond or group linking $R_2$ to the Inhibitor moiety; and
- $R_4$ is a bond or group linking $R_2$ to a L.

2. The nucleotide analog of claim 1, wherein the Inhibitor comprises a charged group selected from the group consisting of —COOH and —PO$_4$.

3. The nucleotide analog of claim 1, wherein the Inhibitor comprises at least two —COOH groups.

4. The nucleotide analog of claim 1, wherein the Inhibitor does not comprise an —PO$_4$ group.

5. The nucleotide analog of claim 1, wherein the Inhibitor does not comprise a n aryl group.

6. The nucleotide analog of claim 1, wherein the Inhibitor comprises a group selected from the group consisting of Glu, Asp, Arg, His, Thr, Trp, Gln, Tyr, Pro and Lys.

7. The nucleotide analog of claim 1, wherein $R_1$ comprises a C—C triple bond or a trans C—C double bond.

8. The nucleotide analog of claim 1, wherein $R_1$ comprises a S—S bond.

9. The nucleotide analog of claim 1, wherein $R_1$ comprises a C—C triple bond and a S—S bond.

10. The nucleotide analog of claim 1, wherein $R_1$ comprises $$-(\equiv)_q - R_6N\overset{O}{\underset{}{\|}}C - ()_r - S - S -$$

wherein $R_6$ is a H or an alkyl group; q and r independently is an integer from about 1 to about 10.

11. The nucleotide analog of claim 10, wherein q is 1 or 2 and r is 1, 2 or 3.

12. The nucleotide analog of claim 1, wherein NTP is selected from dATP, dGTP, dCTP, dTTP, dUTP, ATP, GTP, CTP, TTP, UTP or an analog thereof.

13. The nucleotide analog of claim 1, wherein the L is an optically-detectable moiety.

14. The nucleotide analog of claim 13, wherein the optically-detectable moiety comprises a fluorophore.

15. The nucleotide analog of claim 14, wherein the fluorophore is Cy5 or ATTO 647N.

16. The nucleotide analog of claim 1, wherein $R_3$ comprises $$\overset{R^1}{\underset{O}{\underset{\|}{\overset{|}{N}}}}$$

wherein $R^1$ is H or alkyl groups, and may together form 3, 4, 5, or 6-member rings.

17. The nucleotide analog of claim 16, wherein $R_3$ comprises $$\overset{R^1}{\underset{O}{\underset{\|}{\overset{|}{N}}}}R^4$$

wherein $R^4$ is Glu, Asp, Arg, His, Thr, Trp, Gln, Tyr, Pro or Lys, or a peptide of two or more amino acids comprising an amino acid selected from the group consisting of Glu, Asp, Arg, His, Thr, Trp, Gln, Tyr, Pro and Lys.

18. The nucleotide analog of claim 1, selected from:
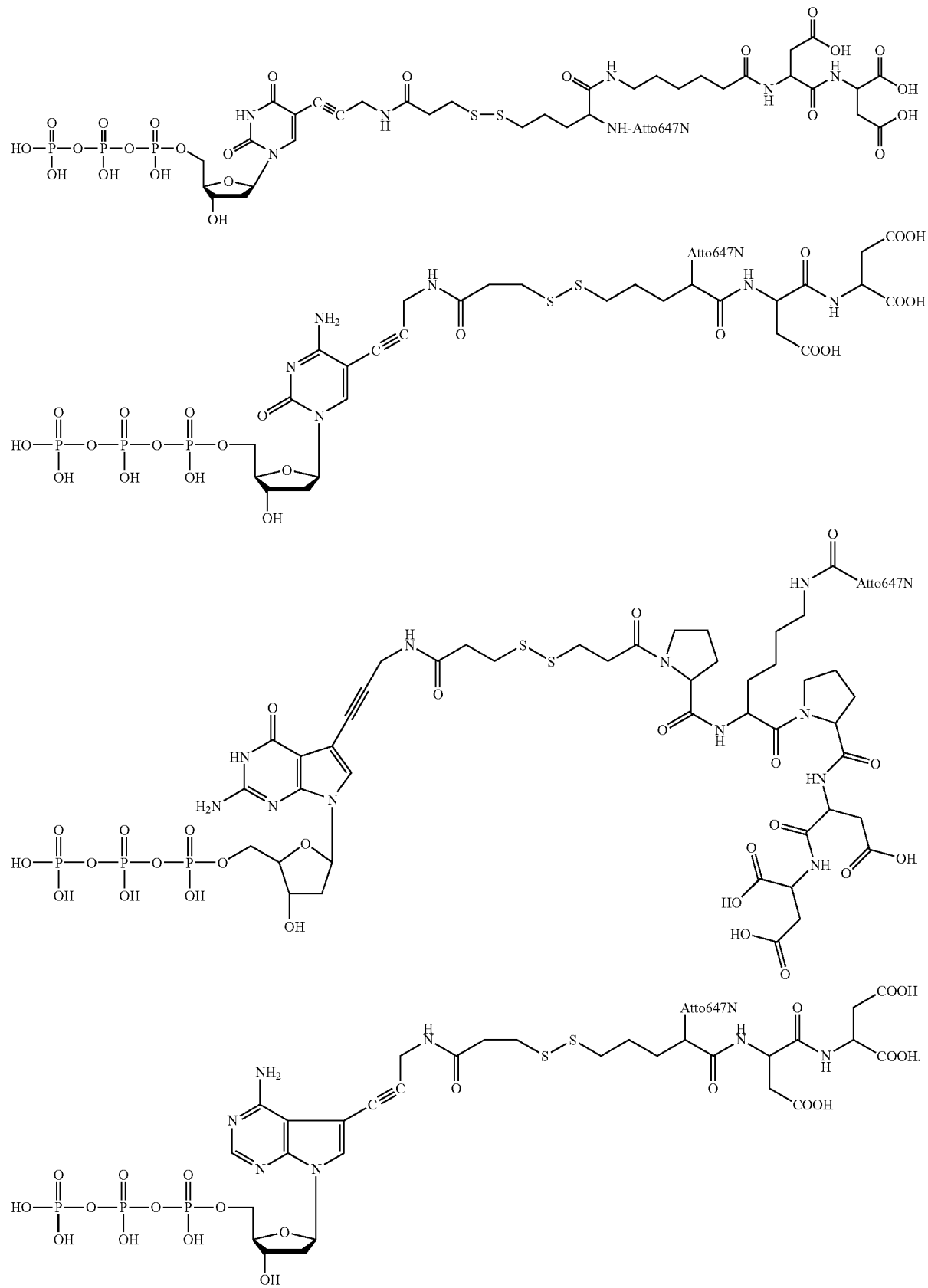

19. A method for sequencing a nucleic acid, the method comprising the steps of:

exposing a nucleic acid duplex comprising a template portion and a primer portion to a nucleotide analog of the following Formula II:

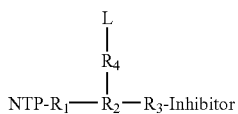   II detecting incorporation of the analog;
removing or neutralizing the inhibitor; and
repeating the exposing, detecting, and removing steps at least once, thereby to determine the sequence of the template, wherein NTP is a nucleoside or nucleotide triphosphate, or an analog thereof, capable of incorporating onto the 3' end of a polynucleotide strand hybridized to a template presenting the complement of the NTP;

L is a detectable label that facilitates the identification of the nucleotide analog;

Inhibitor comprises (a) one or more multiply charged groups or groups capable of becoming multiply charged, or (b) two or more singly charged groups or two or more groups capable of becoming singly charged;

$R_1$ comprises a cleavable bond, which upon cleavage results in de-association of NTP from both L and Inhibitor;

$R_2$ is a tri-valent radical having the formula:

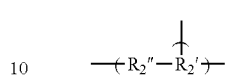

wherein $R_2'$ is a tri-valent radical, and
$R_2''$ is a bi-valent radical selected from:
$-(CH_2)_x-$, $-(CH_2-O)_x-$, $-(CH_2-O)_z-$,
$-(CH_2)_y-$, $-(CH_2)_z-(CH_2-O)_y-$, and the same substituted with one or more groups selected from hydroxyl, halogen, amino, thiol, ($C_1$-$C_6$) alkyl, wherein x, y and z are each integers with x and y+z are each from 2 to 10;

$R_3$ is a bond or group linking $R_2$ to the Inhibitor moiety; and $R_4$ is a bond or group linking $R_2$ to a L.

20. The method of claim 19, wherein the inhibitor is selected from the group consisting of one or more carboxylic acid, one or more phosphate, one or more amino acid, one or more peptide, one or more sulfate, one or more caproic acid, and any combination thereof.

* * * * *